(12) United States Patent
Brody et al.

(10) Patent No.: US 9,598,698 B2
(45) Date of Patent: Mar. 21, 2017

(54) METHODS FOR CO-SILENCING EXPRESSION OF GENES IN FILAMENTOUS FUNGAL STRAINS AND USES THEREOF

(71) Applicant: NOVOZYMES A/S, Bagsvaerd (DK)

(72) Inventors: Howard Brody, Davis, CA (US); Evee Ricacho, Sacramento, CA (US); Hiroshi Teramoto, Chiba (JP)

(73) Assignee: Novozymes A/S, Bagsvaerd (DK)

( * ) Notice: Subject to any disclaimer, the term of this patent is extended or adjusted under 35 U.S.C. 154(b) by 4 days.

(21) Appl. No.: 14/421,330

(22) PCT Filed: Aug. 16, 2013

(86) PCT No.: PCT/US2013/055326
§ 371 (c)(1),
(2) Date: Feb. 12, 2015

(87) PCT Pub. No.: WO2014/028833
PCT Pub. Date: Feb. 20, 2014

(65) Prior Publication Data
US 2016/0002646 A1  Jan. 7, 2016

Related U.S. Application Data

(60) Provisional application No. 61/684,504, filed on Aug. 17, 2012.

(51) Int. Cl.
*C12N 15/80* (2006.01)
*C12N 15/113* (2010.01)
*C12N 15/10* (2006.01)

(52) U.S. Cl.
CPC ......... *C12N 15/80* (2013.01); *C12N 15/1086* (2013.01); *C12N 15/113* (2013.01); *C12N 2310/14* (2013.01); *C12N 2310/53* (2013.01); *C12N 2320/12* (2013.01); *C12N 2330/51* (2013.01)

(58) Field of Classification Search
USPC ........ 435/6.1, 91.1, 91.31, 375, 455, 254.11, 435/320.1, 471; 536/23.1, 24.5, 24.32; 506/10
See application file for complete search history.

(56) References Cited

U.S. PATENT DOCUMENTS

2009/0048111 A1* 2/2009 Huang .................. C12N 15/111
  504/241
2010/0169996 A1* 7/2010 Navarro ............. C12N 15/8281
  800/21

FOREIGN PATENT DOCUMENTS

| WO | 9853083 A1 | 11/1998 |
| WO | 0149844 A1 | 7/2001 |
| WO | 03050288 A1 | 6/2003 |
| WO | 2005056772 A2 | 6/2005 |
| WO | 2008053019 A2 | 5/2008 |
| WO | 2008080017 A1 | 7/2008 |

OTHER PUBLICATIONS

Brummell et al, The Plant J., vol. 33, No. 4, pp. 793-800 (2003).*
Van Houdt et al, Plant Physiology, vol. 131, pp. 245-253 (2003).*
Alder et al, RNA, vol. 9, pp. 25-32 (2003).*
Bleys et al, RNA, vol. 12, pp. 1633-1639 (Sep. 2006).*
Janus et al, Applied and Environmental Microbiology, vol. 73, No. 3, pp. 962-970 (2007).*
Abbott et al, 2002, Plant Physiol 128,844-853.
Fernandez et al,2012, Fungal Genet Biol 49 (4), 294-301.
Fitzgerald et al, 2004, Fungal Genet Biol 41 (10), 963-971.
Janus et al, 2007, Appl Environ Microbiol 73(3), 962-970.
Lacroix et al,2009, Appl Environ Microbiol 75(2), 542-546.
Alder et al, 2003, RNA J 9, 25-32.
Bernstein et al, 2001, Nature 409, 363.
Bleys et al, 2006, RNA J 12, 1633-1639.
Brody et al, 2009, Industr Biotechnol 5, 53-60.
Cao et al, 2007, Chinese Journal of Applied and Environmental Biology 13(2), 284-288.
Chi et al, 2003, PNAS USA 100, 6343-6346.
Elbashir et al, 2001, Genes Dev 15, 188.
Elbashir et al, 2001, Nature 411. 494.
Forsburg et al, 2002, Genome Biol 3, Reviews 1035.
Garcia-Perez et al, 2004, The Plant J 38, 594-602.
Grewal et al, 2003, Science 301, 798-802.
Hammond et al, 1996, Plant Mol Biol 32, 79-88.
Hammond et al, 2001, Sci 293, 1146-1151.
Hannon et al, 2002, Nature 418, 244-251.
Hoa et al, 2003, Insec Biochem Mol Biol 33, 949-957.
Ke et al, 2003, Curr Opin in Chem Biol 7, 516-523.
Kennerdell et al, 2000, Nat. Biotechnol 18, 896-8.
Matzke et al, 1998, Cell Mol Life Sci 54, 94-103.
Morel et al, 2000, Curr Biol 10, 1591-1594.
McCaffrey et al, 2003, Nat Biotechnol. 21, 639-44.
Nykanen et al, 2001, Cell 107, 309-321.
Petersen et al, 2005, Plant Mol Biol 58, 575-583.
Roignant et al, 2003, RNA J 9, 299-308.
Selker, 1997, Trends Genet 13, 296-301.
Sijen et al,2001,Cell 107, 465-476.
Vaistij et al, 2002, The Plant Cell 14, 857-867.
Van Houdt et al, 2003, Plant Physiol 131, 245-253.
Voorhoeve et al, 2003, Trends Biotechnol. 21, 2-4.
Wang et al, 2011, Biotechnology Bulletin 10, 77-83.

* cited by examiner

*Primary Examiner* — Jane Zara
(74) *Attorney, Agent, or Firm* — Robert Starnes

(57) ABSTRACT

The present invention relates to methods for co-silencing expression of genes in a filamentous fungal strain by transitive RNA interference. The present invention also relates to methods for identifying a gene encoding a biological substance of interest.

17 Claims, 21 Drawing Sheets

METHODS FOR CO-SILENCING EXPRESSION OF GENES IN FILAMENTOUS FUNGAL STRAINS AND USES THEREOF

CROSS-REFERENCE TO RELATED APPLICATIONS

This application is a 35 U.S.C. §371 national application of PCT/US2013/055326 filed on Aug. 16, 2013, which claims priority or the benefit under 35 U.S.C. §119 of U.S. Provisional Application No. 61/684,504 filed on Aug. 17, 2012, the contents of which are fully incorporated herein by reference.

REFERENCE TO A SEQUENCE LISTING

This application contains a Sequence Listing in computer readable form. The computer readable form is incorporated herein by reference.

BACKGROUND OF THE INVENTION

Field of the Invention

The present invention relates to methods for co-silencing expression of genes in a filamentous fungal strain. The present invention also relates to methods for identifying genes encoding biological substances of interest in a filamentous fungal cell using such co-silencing methods.

Description of the Related Art

Filamentous fungal strains are widely used for the production of biological substances of commercial value. However, filamentous fungal strains with desirable traits of expression and secretion of a biological substance may not necessarily have the most desirable characteristics for successful fermentation. The production of a biological substance may be accompanied by the production of other substances, e.g., enzymes that degrade the biological substance or co-purify with the biological substance, which can complicate use of the biological substance.

One solution to these problems is to inactivate the gene(s) involved in the production of the undesirable substance. Inactivation can be accomplished by deleting or disrupting the gene(s) using methods well known in the art. However, in some cases, inactivation of the gene may be difficult because of poor targeting to homologous regions of the genome. Inactivation can also be accomplished by random mutagenesis, which is not always specific for the intended target gene and other mutations are often introduced into the host organism. In other situations, the gene and its product may be required for survival of the filamentous fungal strain. Where multiple genes are to be inactivated by deletion or disruption, the task can be very cumbersome and time-consuming. Furthermore, when highly homologous members of gene families exist, deletion or disruption of all members can be very tedious and difficult.

In recent years various forms of epigenetic gene regulation have been described (Selker, 1997, *Trends Genet.* 13: 296-301; Matzke and Matzke, 1998, *Cell. Mol. Life. Sci.* 54: 94-103). These processes influence gene expression by modulating the levels of messenger RNA (Hammond and Baulcombe, 1996, *Plant Mol. Biol.* 32: 79-88; Xi-song Ke et al., 2003, *Current Opinion in Chemical Biology* 7: 516-523) via micro RNAs (Morel et al., 2000, *Curr. Biol.* 10: 1591-1594; Bailis and Forsburg, 2002, *Genome Biol.* 3, Reviews 1035; Grewal and Moazed, 2003, *Science* 301: 798-802).

Based on genetic studies of *Drosophila melanogaster* and *Caenorhabditis elegans*, RNA interference (RNAi), also known as post-transcriptional gene silencing (in plants), is understood to involve silencing expression of a gene by assembly of a protein-RNA effector nuclease complex that targets homologous RNAs for degradation (Hannon, 2002, *Nature* 418: 244-251). The processing of double-stranded RNA (dsRNA) into small interfering RNAs (siRNAs) is accomplished by a family of enzymes known as Dicer (Bernstein et al., 2001, *Nature* 409: 363). Dicer, a member of the RNase III family of endonucleases that specifically cleaves dsRNA, is responsible for digestion of dsRNA into siRNAs ranging from 20-25 nucleotides (Elbashir et al., 2001, *Nature* 411: 494). These siRNAs then associate with the RNA Induced Silencing Complex (RISC) (Elbashir et al., 2001, *Genes and Dev.* 15: 188; NyKanen et al., 2001, *Cell* 197: 300; Hammond et al., 2001, *Science* 293: 1146). Although not well understood, RISC targets the mRNA from which the anti-sense fragment is derived followed by endo and exonuclease digestion of the mRNA effectively silencing expression of that gene. RNAi has been demonstrated in plants, nematodes, insects, mammals, and filamentous fungi (Matzke and Matzke, 1998, supra; Kennerdell et al., 2000, *Nat. Biotechnol.* 18: 896-8; Bosher et al., 1999, *Genetics* 153: 1245-56; Voorhoeve and Agami, 2003, *Trends Biotechnol.* 21: 2-4; McCaffrey et al., 2003, *Nat. Biotechnol.* 21: 639-44; WO 03/050288; WO 01/49844; WO 98/53083; and WO 05/056772).

Transitive RNAi refers to the movement of the silencing signal beyond a particular gene. In plants, transitive silencing has been found to occur both upstream and downstream of the mRNA targeted for gene silencing by double-stranded RNA (Fabian et al., 2002, *Plant Cell* 14: 857-867; Garcia-Perez et al., 2004, *The Plant Journal* 38: 594-602; Vaistij et al., 2002, *The Plant Cell* 14: 857-867; Van Houdt et al., 2003, *Plant Physiol.* 131: 245-253). In *Caenorhabditis elegans*, transitive RNAi has been described as silencing of the transcript upstream of the dsRNA inducer (Alder et al., 2003, *RNA J.* 9: 25-32; Hannon, 2002, *Nature* 418: 244-251; Sijen et al., 2001, *Cell* 107: 465-476). In *C. elegans*, descriptions of transitive RNAi indicate that in addition to siRNAs derived from the dsRNA inducer, secondary siRNAs sharing homology with 5' flanking sequences are generated, presumably the result of RNA-dependent RNA polymerase (RdRP) and Dicer activity (Bleys et al., 2006, *RNA J.* 12: 1633-1639; Petersen et al., 2005, *Plant Molecular Biology* 58: 575-583). Transitive RNAi is not ubiquitous among insects and mammals (Chi et al., 2003, *Proc. Natl. Acad. Sci. USA* 100: 6343-6346; Hoa et al., 2003, *Insect Biochemistry and Molecular Biology* 33: 949-957; Roignamt et al., 2003, *RNA J.* 9: 299-308).

Transitive RNAi differs from conventional RNAi. Although double-stranded RNA serves as the inducer of both RNAi and transitive RNAi, transitive RNAi appears to require an RdRP, whereas RNAi alone does not. Consequently, in organisms demonstrating transitive RNAi, gene silencing is not limited by the boundaries of double-stranded RNA, and gene silencing can extend into flanking sequences. However, in organisms lacking transitive RNAi, gene silencing is confined within the region of double strandedness. RNA interference by both conventional and transitive mechanisms can give rise to strains in which expression of the target gene is either partially or completely suppressed (Brody and Maiyuran, 2009, *Industr. Biotechnol.* 5: 53-60; Fernandez et al., 2012, *Fungal Genet. Biol.* 49: 294-301).

It would be an advantage in the art to have alternative methods for silencing expression of more than one gene for strain development and improvement, functional genomics, and pathway engineering of filamentous fungal strains. It would also be an advantage in the art to overcome one of the limitations of previous RNAi methods in filamentous fungi, i.e., how to identify strains/transformants in which gene silencing is most effective.

The present invention relates to methods for silencing expression of more than one gene in filamentous fungal strains and methods of using silencing of phenotypic markers to identify transformants in which silencing of a target gene is most efficient.

SUMMARY OF THE INVENTION

The present invention relates to methods for co-silencing expression of genes encoding biological substances in a filamentous fungal strain, comprising:

(a) inserting into the genome of the filamentous fungal strain a double-stranded transcribable nucleic acid construct comprising a promoter operably linked to a first polynucleotide comprising a first transcribable region with homology to a first target gene encoding a first biological substance, a second polynucleotide comprising a second transcribable region with homology to a second target gene encoding a second biological substance, and a third polynucleotide comprising a third transcribable region with no effective homology to the first and second target genes; wherein the third transcribable region comprises two segments complementary to each other in reverse orientation; and wherein the first, second, and third transcribable regions are transcribed as a single-stranded RNA molecule; and (b) producing short interfering RNAs (siRNAs) by cultivating the filamentous fungal strain under conditions to produce RNA transcripts of the double-stranded transcribable nucleic acid construct that are then converted to the siRNAs, which interact with RNA transcripts of the target genes to silence expression of the target genes encoding the first and second biological substances.

The present invention also relates to filamentous fungal strains comprising a double-stranded transcribable nucleic acid construct comprising a promoter operably linked to a first polynucleotide comprising a first transcribable region with homology to a first target gene encoding a first biological substance, a second polynucleotide comprising a second transcribable region with homology to a second target gene encoding a second biological substance, and a third polynucleotide comprising a third transcribable region with no effective homology to the first and second target genes wherein the third transcribable region comprises two segments complementary to each other in reverse orientation; wherein the first, second, and third transcribable regions are transcribed as a single-stranded RNA molecule; and wherein production of short interfering RNAs (siRNAs) is by cultivating the filamentous fungal strain under conditions to produce RNA transcripts of the double-stranded transcribable nucleic acid construct that are then converted to the siRNAs, which interact with RNA transcripts of the target genes to silence expression of the target genes encoding the first and second biological substances.

The present invention also relates to methods for producing a biological substance of interest, comprising:

(a) cultivating a filamentous fungal strain under conditions conducive for production of the biological substance of interest, wherein the filamentous fungal strain comprises a double-stranded transcribable nucleic acid construct comprising a promoter operably linked to a first polynucleotide comprising a first transcribable region with homology to a first target gene encoding a first biological substance, a second polynucleotide comprising a second transcribable region with homology to a second target gene encoding a second biological substance, and a third polynucleotide comprising a third transcribable region with no effective homology to the first and second target genes wherein the third transcribable region comprises two segments complementary to each other in reverse orientation; wherein the first, second, and third transcribable regions are transcribed as a single-stranded RNA molecule; wherein production of short interfering RNAs (siRNAs) is by cultivating the filamentous fungal strain under conditions to produce RNA transcripts of the double-stranded transcribable nucleic acid construct that are then converted to the siRNAs comprising sequences of the target genes to be silenced, which interact with RNA transcripts of the target genes to silence expression of the target genes encoding the first and second biological substances; and wherein the filamentous fungal strain comprises a fourth polynucleotide encoding the biological substance of interest; and optionally (b) recovering the biological substance of interest from the cultivation medium.

The present invention also relates to methods for identifying a gene encoding a biological substance of interest in a filamentous fungal cell, comprising:

(a) transforming a population of a filamentous fungal host cell with a double-stranded transcribable nucleic acid construct comprising a promoter operably linked to a first polynucleotide comprising a first transcribable region with homology to a first target gene encoding a phenotypic marker, a second polynucleotide comprising a second transcribable region with homology to a second target gene encoding the biological substance of interest, and a third polynucleotide comprising a third transcribable region with no effective homology to the first and second target genes; wherein the third transcribable region comprises two segments complementary to each other in reverse orientation; wherein the first, second, and third transcribable regions are transcribed as a single-stranded RNA molecule; and wherein the double-stranded transcribable nucleic acid construct inserts into the genome of the filamentous fungal host cell;

(b) producing short interfering RNAs (siRNAs) by cultivating the transformed population of the filamentous fungal host cell under conditions to produce RNA transcripts of the double-stranded transcribable nucleic acid construct that are then converted to the siRNAs, which interact with RNA transcripts of the first target gene resulting in a phenotypic change of the transformed filamentous fungal host cell and interact with RNA transcripts of the second target gene silencing expression of the biological substance of interest;

(c) selecting transformants from the transformed population of the filamentous fungal host cell which exhibit the phenotypic change;

(d) screening each of the selected transformants exhibiting the phenotypic change for silencing of the second target gene encoding the biological substance of interest by measuring the level of the biological substance produced by each of the transformants relative to the level of the biological substance produced by the filamentous fungal host cell; and optionally (e) isolating the second target gene encoding the biological substance of interest.

The present invention also relates to methods for identifying a gene encoding a biological substance of interest in a filamentous fungal cell, comprising:

(a) transforming a population of the filamentous fungal cell with a DNA library from the filamentous fungal cell wherein each member of the DNA library is cloned into a double-stranded transcribable nucleic acid construct comprising a promoter operably linked to a first polynucleotide comprising a first transcribable region with homology to a first target gene encoding a phenotypic marker, a second polynucleotide comprising a member of the DNA library as a second transcribable region with homology to a second target gene encoding the biological substance of interest, and a third polynucleotide comprising a third transcribable region with no effective homology to the first and second target genes; wherein the third transcribable region comprises two segments complementary to each other in reverse orientation; wherein the first, second, and third transcribable regions are transcribed as a single-stranded RNA molecule; and wherein the double-stranded transcribable nucleic acid construct inserts into the genome of the filamentous fungal cell;

(b) producing short interfering RNAs (siRNAs) by cultivating the transformed population of the filamentous fungal cell under conditions to produce RNA transcripts of the double-stranded transcribable nucleic acid construct that are then converted to the siRNAs, which interact with RNA transcripts of the first target gene resulting in a phenotypic change of the transformed filamentous fungal cell and interact with RNA transcripts of the second target gene silencing expression of the biological substance of interest;

(c) selecting transformants from the transformed population of the filamentous fungal cell which exhibit the phenotypic change;

(d) screening each of the selected transformants exhibiting the phenotypic change for silencing of the second target gene encoding the biological substance of interest by measuring the level of the biological substance produced by each of the transformants relative to the level of the biological substance produced by the filamentous fungal cell; and optionally (e) isolating the second target gene encoding the biological substance of interest.

The present invention also relates to double-stranded transcribable nucleic acid constructs comprising a promoter operably linked to a first polynucleotide comprising a first transcribable region with homology to a first target gene encoding a first biological substance, a second polynucleotide comprising a second transcribable region with homology to a second target gene encoding a second biological substance, and a third polynucleotide comprising a third transcribable region with no effective homology to the first and second target genes.

The present invention also relates to double-stranded transcribable nucleic acid constructs comprising a promoter operably linked to a first polynucleotide comprising a first transcribable region with homology to a first target gene encoding a phenotypic marker, a second polynucleotide comprising a second transcribable region with homology to a second target gene encoding the biological substance of interest, and a third polynucleotide comprising a third transcribable region with no effective homology to the first and second target genes.

Figure 1:
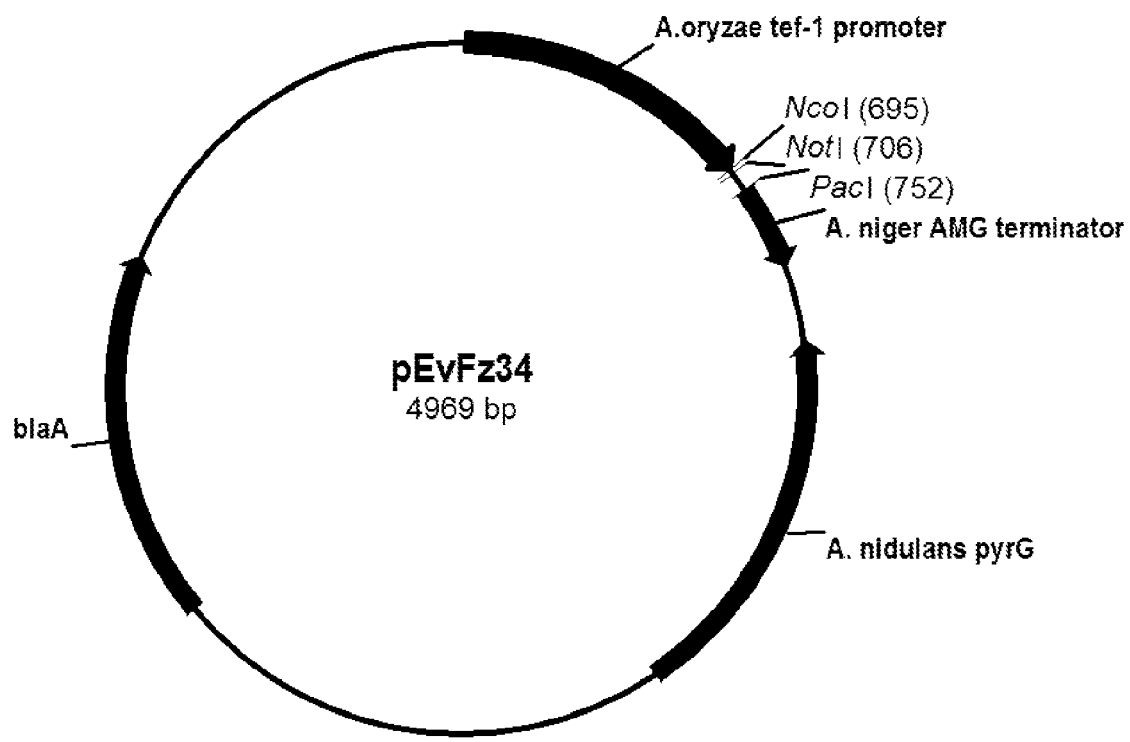
FIG. 1 shows a restriction map of pEvFz34.

DEFINITIONS cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Co-silencing of genes: The term "co-silencing of genes" means reducing (suppressing) or eliminating (inactivating) expression of two or more (e.g., several) genes. In one aspect, at least two genes are silenced. In another aspect, at least three genes are silenced. In another aspect, at least four genes are silenced. In another aspect, at least five genes are silenced. In another aspect, two genes are silenced. In another aspect, three genes are silenced. In another aspect, four genes are silenced, In another aspect, five genes are silenced.

DNA library: The term "DNA library" means a collection of DNA molecules. The DNA molecules may include all or part of the genetic material of an organism. Without limitation, the DNA molecules may be derived from genomic DNA, cDNA, synthetic DNA, PCR products, etc., which may be restriction enzyme digested or sheared. The DNA molecules are preferably cloned into a vector(s). A collection representing the entire genome is called a genomic library. A collection representing random mutants is called a random mutant library. An assortment of DNA copies of messenger RNA produced by a cell is known as a complimentary DNA (cDNA) library. The DNA library may also be random or specific. A random DNA library is a library with equivalent probabilities that the majority, if not all DNA fragments, can insert into a cloning vector such that there is complete representation of most, if not all, of the DNA sequences comprising the starting material. A specific DNA library comprises subsets of DNA molecules encoding related functions (e.g., transcription factors, protein kinases, membrane transport proteins, secondary metabolites, etc.).

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 65° C.

Homology: The term "homology" means more than the minimum number of corresponding nucleotides on a sense strand and the reverse complement strand, which can undergo Watson-Crick base pairing necessary for annealing of the strands.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Hybrid promoter: The term "hybrid promoter" means parts of two or more promoters that are fused together to generate a sequence that is a fusion of the parts of the two or more promoters, which when operably linked to a coding sequence mediates the transcription of the coding sequence into mRNA.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more (e.g., several) or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 60° C.

Mutant promoter: The term "mutant promoter" means a promoter having a nucleotide sequence comprising a substitution, deletion, and/or insertion of one or more (e.g., several) nucleotides of a parent promoter, wherein the mutant promoter has more or less promoter activity than the corresponding parent promoter. The term "mutant promoter" also encompasses natural mutants and in vitro generated mutants obtained using methods known in the art such as classical mutagenesis, site-directed mutagenesis, and DNA shuffling.

No effective homology: The term "no effective homology" means fewer than the minimum number of corresponding nucleotides on a sense strand and the reverse complement strand, which can undergo Watson-Crick base pairing necessary for annealing of the strands and which comprise preferably less than 20, more preferably less than 15, even more preferably less than 10, most preferably less than 5, and even most preferably no contiguous nucleotides of identical sequence to the target gene. In one aspect, the corresponding nucleotides on a sense strand and the reverse complement have no contiguous nucleotides of identical sequence to the target gene. In another aspect, the corresponding nucleotides on a sense strand and the reverse complement have less than 20 nucleotides of identical sequence to the target gene. In another aspect, the corresponding nucleotides on a sense strand and the reverse complement have less than 15 nucleotides of identical sequence to the target gene. In another aspect, the corresponding nucleotides on a sense strand and the reverse complement have less than 10 nucleotides of identical sequence to the target gene. In another aspect, the corresponding nucleotides on a sense strand and the reverse complement have less than 5 nucleotides of identical sequence to the target gene.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more (e.g., several) control sequences.

Operably linked: The term "operably linked" means a configuration in which a control sequence is placed at an appropriate position relative to the coding sequence of a polynucleotide such that the control sequence directs expression of the coding sequence.

Phenotypic marker: The term "phenotypic marker" means a gene upon being silenced confers an observable characteristic or trait on the host cell that can be readily identified, screened, or selected. In other words, phenotypic markers encompass both selectable markers and markers for screening. Non-limiting examples of selectable markers include resistance to drugs or toxic metabolites, or growth or lack of growth on specific nutrients, whereas non-limiting examples of screening markers include genes that alter colony or spore color, or colony morphology. Other markers are described herein.

Phenotype change: The term "phenotype change" means a change in an observable characteristic or trait of a strain that distinguishes it from a parental or reference strain. The phenotype change results from silencing of a phenotypic marker.

Promoter: The term "promoter" means a DNA sequence that binds RNA polymerase and directs the polymerase to the correct downstream transcriptional start site of a nucleic acid sequence encoding a biological substance to initiate transcription. RNA polymerase effectively catalyzes the assembly of messenger RNA complementary to the appropriate DNA strand of a coding region. The term "promoter" will also be understood to include the 5' non-coding region (between promoter and translation start) for translation after transcription into mRNA, cis-acting transcription control elements such as enhancers, and other nucleotide sequences capable of interacting with transcription factors.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Alignment–Total Number of Gaps in Alignment)

Short interfering RNAs: The term "short interfering RNAs" or "siRNAs" means 20-25 nucleotide long double-stranded RNA fragments, the products of Dicer and Dicer-like mediated digestion of double-stranded RNA.

Silencing: The term "silencing" means reducing (suppressing) or eliminating (inactivating) expression of a gene.

Tandem promoter: The term "tandem promoter" means two or more promoter sequences, arranged in tandem, operably linked to a coding sequence for mediating transcription of the coding sequence into mRNA.

Transitive RNA interference: The term "transitive RNA interference" or "transitive RNAi" means the movement of a silencing signal beyond a particular gene. In transitive RNAi, double-stranded RNA (dsRNA) can serve as template for the synthesis of new dsRNA from which siRNA sharing homology with a target sequence results in the extension or spread of silencing of new sequence along the mRNA.

Transitive silenced target sequences: The phrase "transitive silenced target sequences" means a dsRNA sequence earmarked for gene silencing, wherein the dsRNA sequence is the result of siRNA extension from adjoining sequences.

Two segments complementary to each other in reverse orientation: The phrase "two segments complementary to each other in reverse orientation" means one of several stretches or pieces of DNA that fit with others to constitute a whole and capable of undergoing Watson-Crick base pairing, having the potential to form a hairpin DNA structure.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 45° C.

DETAILED DESCRIPTION OF THE INVENTION

The present invention relates to methods for co-silencing expression of genes encoding biological substances in a filamentous fungal strain, comprising: (a) inserting into the genome of the filamentous fungal strain a double-stranded transcribable nucleic acid construct comprising a promoter operably linked to a first polynucleotide comprising a first transcribable region with homology to a first target gene encoding a first biological substance, a second polynucleotide comprising a second transcribable region with homology to a second target gene encoding a second biological substance, and a third polynucleotide comprising a third transcribable region with no effective homology to the first and second target genes; wherein the third transcribable region comprises two segments complementary to each other in reverse orientation; and wherein the first, second, and third transcribable regions are transcribed as a single-stranded RNA molecule; and (b) producing short interfering RNAs (siRNAs), comprising sequences of the target genes to be silenced, by cultivating the filamentous fungal strain under conditions to produce RNA transcripts of the double-stranded transcribable nucleic acid construct that are then converted to the siRNAs, which interact with RNA transcripts of the target genes to silence expression of the target genes encoding the first and second biological substances.

In one aspect, the double-stranded transcribable nucleic acid construct further comprises at least one additional polynucleotide comprising a transcribable region with homology to an additional target gene encoding an additional biological substance. The at least one additional polynucleotide is also operably linked to the promoter and is located anywhere 3' of the third polynucleotide. In another aspect, the at least one additional polynucleotide is one polynucleotide. In another aspect, the at least one additional polynucleotide is two polynucleotides. In another aspect, the at least one additional polynucleotide is three polynucleotides. In another aspect, the one additional polynucleotide is a first additional polynucleotide comprising a first additional transcribable region with homology to a first additional target gene encoding a first additional biological substance. In another aspect, the one additional polynucleotide is a second additional polynucleotide comprising a second additional transcribable region with homology to a second additional target gene encoding a second additional biological substance. In another aspect, the one additional polynucleotide is a third additional polynucleotide comprising a third additional transcribable region with homology to a third additional target gene encoding a third additional biological substance. In another aspect, one or more (e.g., several) of the additional polynucleotides are selected from the group consisting of a first additional polynucleotide comprising a first additional transcribable region with homology to a first additional target gene encoding a first additional biological substance; a second additional polynucleotide comprising a second additional transcribable region with homology to a second additional target gene encoding a second additional biological substance; and a third additional polynucleotide comprising a third additional transcribable region with homology to a third additional target gene encoding a third additional biological substance.

Transformants comprising a double-stranded transcribable nucleic acid construct of the present invention produce transcription products composed of target segments flanked 3' by an inverted repeat (IR) having no effective homology with the target genes. Utilizing an RNA-dependent RNA polymerase (RdRP), siRNAs are synthesized upstream from the 5' IR boundary. This infiltration of the target sequence is accomplished using mechanisms not fully understood. Evidence suggests that double-stranded RNAs (dsRNAs) produced by folding and annealing of the IR are processed by Dicer producing siRNAs with shared homology to the IR. The siRNAs serve as primers for RdRP for continued extension of adjoining target sequences (Moissiard et al., 2007, *RNA* 13: 1268-1278). Alternatively, RdRP is attracted or guided to dsRNA initiating de novo synthesis of siRNAs upstream from the IR (Moissiard et al., 2007, supra). It is recognized herein that one siRNA may be sufficient to silence both target genes if they are directly next to each other or within 10 kb, e.g., within 7.5 kb, within 5 kb, within 2.5 kb, within 1 kb, or within 0.5 kb of each other. On the other hand, if the target genes are not within 10 kb of each other, a separate siRNA may be required for silencing each target gene.

The methods of the present invention provide new opportunities for strain development and improvement, functional genomics, and pathway engineering in filamentous fungal strains. For example, the present methods can be used as a tool for filamentous fungal host strain development by means of gene manipulation and pathway engineering or as replacement for gene knockouts, a time-consuming approach with variable rates of success. A gene may be resistant to inactivation by standard methods known in the art such as gene knockout. The methods of the present invention provide a solution for silencing expression of multiple genes. Gene knockouts are dependent on site-specific gene replacements. In fungi efficacy of this process is affected by the chromosome locus, DNA sequences shared by the replacement construct and genome, and/or length of the shared homology. Attainment of transitive gene silencing of multiple genes as described herein is uniquely dependent on cloning of portions of the target sequences upstream of a sequence comprised of an inverted repeat. The methods are also particularly useful and efficient for silencing highly expressed genes in a particular filamentous fungal strain, which can be very important, for example, in developing the organism as a production host. This ability demonstrates the strength of the methods of the present invention.

The methods are also useful for silencing expression of a multiple of genes that are highly homologous to each other, especially genes of the same family or homologous genes in a biosynthetic or metabolic pathway. The term "highly homologous" means a degree of sequence identity between the homologous genes of at least 75%, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. For purposes of the present invention, the degree of sequence identity between two nucleic acid sequences is determined as defined herein.

The methods are further useful because they can be manipulated to cause a variable reduction in expression of multiple biological substances. This variability is especially important where complete knock-out of genes encoding biological substances would be lethal to a particular filamentous fungal strain, such as in a secondary pathway that feeds into a biosynthetic pathway of interest.

In the methods of the present invention, the first polynucleotide comprises a first transcribable region with homology to a first target gene. The second polynucleotide comprises a second transcribable region with homology to a second target gene. The third polynucleotide comprises a third transcribable region with no effective homology to the first and second target genes, wherein the third transcribable region comprises two segments complementary to each other in reverse orientation. The first additional polynucleotide comprises a first additional transcribable region with homology to a first additional target gene. The second additional polynucleotide comprises a second additional transcribable region with homology to a second additional target gene. The third additional polynucleotide comprises a third additional transcribable region with homology to a third additional target gene.

The first polynucleotide comprising a first transcribable region with homology to the first target gene, the second polynucleotide comprising a second transcribable region with homology to the second target gene, and the third polynucleotide comprising a third transcribable region with no effective homology to the first and second target genes, as well as the additional polynucleotides, may or may not be separated by a polynucleotide intervening sequence. The polynucleotide intervening sequence is a nucleotide sequence that has no effective homology to the first, second, and third polynucleotides in the double-stranded transcribable nucleic acid construct. The polynucleotide sequences of the double-stranded transcribable nucleic acid construct may be of genomic, cDNA, RNA, semisynthetic, synthetic origin, or any combinations thereof.

In one aspect, the first and second polynucleotides are separated by a polynucleotide intervening sequence. In another aspect, the second and third polynucleotides are separated by a polynucleotide intervening sequence. In another aspect, the first, second, and third polynucleotides are separated by polynucleotide intervening sequences. Each of the aspects above may further comprise any combination of one or more (e.g., several) additional polynucleotides, as described above. The polynucleotide intervening sequence preferably consists of less than 150 nucleotides, e.g., less than 100 nucleotides, less than 60 nucleotides, less than 40 nucleotides, less than 20 nucleotides, or less than 10 nucleotides.

In another aspect, the first and second polynucleotides are not separated by a polynucleotide intervening sequence. In another aspect, the second and third polynucleotides are not separated by a polynucleotide intervening sequence. In another aspect, the first, second, and third polynucleotides are not separated by a polynucleotide intervening sequence. Each of the aspects above may further comprise any combination of one or more (e.g., several) additional polynucleotides, as described above.

The polynucleotide intervening sequence can be any nucleotide sequence with no effective homology to the first polynucleotide, second polynucleotide, and/or third polynucleotide, as well as one or more of the additional polynucleotides, and preferably has no effective homology to sequences in the genome of the filamentous fungal strain.

The ability to co-silence multiple genes according to the present invention provides several uses as described below to identify a gene encoding a biological substance of interest in a filamentous fungal cell using a double-stranded transcribable nucleic acid construct as a selection system. The selection system may be used to screen a filamentous fungal cell for genes of interest. The selection system may also be used to screen a DNA library native to a filamentous fungal cell for genes of interest.

The present invention also relates to methods for identifying a gene encoding a biological substance of interest in a filamentous fungal cell, comprising: (a) transforming a population of a filamentous fungal host cell with a double-stranded transcribable nucleic acid construct comprising a promoter operably linked to a first polynucleotide comprising a first transcribable region with homology to a first target gene encoding a phenotypic marker, a second polynucleotide comprising a second transcribable region with homology to a second target gene encoding the biological substance of interest, and a third polynucleotide comprising a third transcribable region with no effective homology to the first and second target genes; wherein the third transcribable region comprises two segments complementary to each other in reverse orientation; wherein the first, second, and third transcribable regions are transcribed as a single-stranded RNA molecule; and wherein the double-stranded transcribable nucleic acid construct inserts into the genome of the filamentous fungal host cell; (b) producing short interfering RNAs (siRNAs), comprising sequences of the target genes to be silenced, by cultivating the transformed population of the filamentous fungal host cell under conditions to produce RNA transcripts of the double-stranded transcribable nucleic acid construct that are then converted to the siRNAs, which interact with RNA transcripts of the first target gene resulting in a phenotypic change of the transformed filamentous fungal host cell and interact with RNA transcripts of the second target gene silencing expression of the biological substance of interest; (c) selecting transformants from the transformed population of the filamentous fungal host cell which exhibit the phenotypic change; (d) screening each of the selected transformants exhibiting the phenotypic change for silencing of the second target gene encoding the biological substance of interest by measuring the level of the biological substance produced by the transformants relative to the level of the biological substance produced by the filamentous fungal host cell; and optionally (e) isolating the second target gene encoding the biological substance of interest.

In step (a), a population of a filamentous fungal host cell is transformed with a double-stranded transcribable nucleic acid construct comprising a promoter operably linked to a first polynucleotide comprising a first transcribable region with homology to a first target gene encoding a phenotypic marker, a second polynucleotide comprising a second transcribable region with homology to a second target gene encoding the biological substance of interest, and a third polynucleotide comprising a third transcribable region with no effective homology to the first and second target genes. The third transcribable region comprises two segments complementary to each other in reverse orientation. Upon transformation into the filamentous fungal host cell, the double-stranded transcribable nucleic acid construct inserts into the genome of the filamentous fungal host cell. Upon transcription, the first, second, and third transcribable regions are transcribed as a single-stranded RNA molecule.

In step (b), production of short interfering RNAs (siRNAs) comprising partial double-stranded RNA sequences corresponding to the target genes to be silenced is accomplished by cultivating the transformed population of the filamentous fungal host cell under conditions to produce RNA transcripts of the double-stranded transcribable nucleic acid construct that are then converted to the siRNAs. The siRNAs interact with RNA transcripts of the first target gene resulting in a phenotypic change of the transformed filamentous fungal host cell and interact with RNA transcripts of the second target gene silencing expression of the biological substance of interest. As mentioned above, it is recognized herein that one siRNA may be sufficient to silence both target genes if they are directly next to each other or within 10 kb, e.g., within 7.5 kb, within 5 kb, within 2.5 kb, within 1 kb, or within 0.5 kb of each other. On the other hand, if the target genes are not within 10 kb of each other, a separate siRNA may be required for silencing each target gene.

In step (c), transformants are selected from the transformed population of the filamentous fungal host cell based on the phenotypic change.

In step (d), the selected transformants exhibiting the phenotypic change are each screened for silencing of the second target gene encoding the biological substance of interest by measuring the level of the biological substance produced by each of the transformants relative to the level of the biological substance produced by the filamentous fungal host cell. Measuring the level of the biological substance produced can be performed using methods known in the art. Such methods include, without limitation, specific antibodies, high performance liquid chromatography, capillary chromatography, formation of an enzyme product, disappearance of an enzyme substrate, SDS-PAGE, fluorescence, Northern analysis, or RT-PCR. Alternative methods known in the art may be used where silencing of the second target gene results in changes in growth characteristics such as altered morphology, or increased/decreased susceptibility to drugs, antimetabolites, metals, and other toxic compounds.

In step (e), the second target gene encoding the biological substance of interest is optionally isolated. The target gene can be isolated from a transformant or the filamentous fungal host cell. The techniques used to isolate or clone the gene are known in the art and include isolation from genomic DNA, preparation from cDNA, or a combination thereof. The cloning of the gene from such genomic DNA can be effected, e.g., by using the well-known polymerase chain reaction (PCR). See, for example, Innis et al., 1990, *PCR Protocols: A Guide to Methods and Application*, Academic Press, New York. Oligonucleotides for performing PCR of the second target gene can be based on the nucleotide sequence of the second transcribable region.

The present invention also relates to methods for identifying a gene encoding a biological substance of interest in a filamentous fungal cell, comprising: (a) transforming a population of the filamentous fungal cell with a DNA library from the filamentous fungal cell wherein each member of the DNA library is cloned into a double-stranded transcribable nucleic acid construct comprising a promoter operably linked to a first polynucleotide comprising a first transcribable region with homology to a first target gene encoding a phenotypic marker, a second polynucleotide comprising a member of the DNA library as a second transcribable region with homology to a second target gene encoding the biological substance of interest, and a third polynucleotide comprising a third transcribable region with no effective homology to the first and second target genes; wherein the third transcribable region comprises two segments complementary to each other in reverse orientation; wherein the first, second, and third transcribable regions are transcribed as a single-stranded RNA molecule; and wherein the double-stranded transcribable nucleic acid construct inserts into the genome of the filamentous fungal cell; (b) producing short interfering RNAs (siRNAs), comprising partial double-stranded RNA sequences corresponding to the target genes to be silenced, by cultivating the transformed population of the filamentous fungal cell under conditions to produce RNA transcripts of the double-stranded transcribable nucleic acid construct that are then converted to the siRNAs, which interact with RNA transcripts of the first target gene resulting in a phenotypic change of the transformed filamentous fungal cell and interact with RNA transcripts of the second target gene silencing expression of the biological substance of interest; (c) selecting transformants from the transformed population of the filamentous fungal cell which exhibit the phenotypic change; (d) screening each of the selected transformants exhibiting the phenotypic change for silencing of the second target gene encoding the biological substance of interest by measuring the level of the biological substance produced by each of the transformants relative to the level of the biological substance produced by the filamentous fungal cell; and optionally (e) isolating the second target gene encoding the biological substance of interest.

In step (a), a population of a filamentous fungal host cell is transformed with a DNA library using methods known in the art. Each member of the DNA library is cloned into a double-stranded transcribable nucleic acid construct comprising a promoter operably linked to a first polynucleotide comprising a first transcribable region with homology to a first target gene encoding a phenotypic marker, a second polynucleotide comprising a member of the DNA library as a second transcribable region with homology to a second target gene encoding the biological substance of interest, and a third polynucleotide comprising a third transcribable region with no effective homology to the first and second target genes.

In step (b), production of short interfering RNAs (siRNAs) comprising partial double-stranded RNA sequences corresponding to the target genes to be silenced is accomplished by cultivating the transformed population of the filamentous fungal host cell under conditions to produce RNA transcripts of the double-stranded transcribable nucleic acid construct that are then converted to the siRNAs. The siRNAs interact with RNA transcripts of the first target gene resulting in a phenotypic change of the transformed filamentous fungal host cell and interact with RNA transcripts of the second target gene silencing expression of the biological substance of interest. As mentioned earlier, it is recognized herein that one siRNA may be sufficient to silence both target genes if they are directly next to each other or within 10 kb, e.g., within 7.5 kb, within 5 kb, within 2.5 kb, within 1 kb, or within 0.5 kb of each other. On the other hand, if the target genes are not within 10 kb of each other, a separate siRNA may be required for silencing each target gene.

In step (c), transformants are selected from the transformed population of the filamentous fungal host cell based on a phenotypic change.

In step (d), each of the selected transformants exhibiting the phenotypic change are screened for silencing of the second target gene encoding the biological substance of interest by measuring the level of the biological substance produced by each of the transformants relative to the level of the biological substance produced by the filamentous fungal cell. Measuring the level of the biological substance produced can be performed using methods known in the art as described herein.

In step (e), the second target gene encoding the biological substance of interest is optionally isolated. The target gene can be isolated from a transformant or the filamentous fungal cell. The target gene may be isolated as described herein.

The present invention also relates to double-stranded transcribable nucleic acid constructs comprising a promoter operably linked to a first polynucleotide comprising a first transcribable region with homology to a first target gene encoding a first biological substance, a second polynucleotide comprising a second transcribable region with homology to a second target gene encoding a second biological substance, and a third polynucleotide comprising a third transcribable region with no effective homology to the first and second target genes.

The present invention also relates to double-stranded transcribable nucleic acid constructs comprising a promoter operably linked to a first polynucleotide comprising a first transcribable region with homology to a first target gene encoding a phenotypic marker, a second polynucleotide comprising a second transcribable region with homology to a second target gene encoding the biological substance of interest, and a third polynucleotide comprising a third transcribable region with no effective homology to the first and second target genes.

In the aspects above, the double-stranded transcribable nucleic acid construct may be contained in a vector. A vector can be a double-stranded circular DNA molecule or a linear DNA molecule that is used to transfer the nucleic acid construct(s) from the cell in which it was created into a fungal host cell. Such vectors can integrate into the host cell genome or replicate autonomously. Examples include plasmid vectors, binary vectors, cloning vectors, shuttle vectors, viral vectors, and linear vectors. Alternatively, the double-stranded transcribable nucleic acid construct is introduced into a filamentous fungal cell as is, i.e., not as a component of a vector.

Promoter

The promoter may be native or foreign (heterologous) to the first homologous transcribable region, the second homologous transcribable region, or first and second homologous transcribable regions and native or foreign to the filamentous fungal strain. In the methods of the present invention, the promoter can be a native promoter, heterologous promoter, mutant promoter, hybrid promoter, or tandem promoter.

Examples of promoters useful in the methods of the present invention include the promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In one aspect, the promoter is the NA2-tpi promoter. In another aspect, the promoter is the TAKA/NA2-tpi leader hybrid promoter. In another aspect, the promoter is the TAKA promoter. In another aspect, the promoter is the *Aspergillus oryzae* tef-1 promoter. In another aspect, the promoter is the *Aspergillus niger* or *Aspergillus awamori* glaA promoter. In another aspect, the promoter is the *Aspergillus niger* or *Aspergillus oryzae* niaD promoter. In another aspect, the promoter is the *Saccharomyces cerevisiae* fcy1 promoter.

Homologous Transcribable Regions

The term "transcribable region with homology to a target gene" means a nucleotide sequence that is homologous to the open reading frame of a target gene, or a portion thereof, and is transcribed into an RNA, e.g., ncRNA (non-coding RNA), tRNA (transfer RNA), rRNA (ribosomal RNA), miRNA (micro RNA), or mRNA (messenger RNA), which may or may not be translated into a biological substance, e.g., polypeptide, when placed under the control of the appropriate regulatory sequences. The boundaries of the transcribable region are generally determined by the transcription start site located just upstream of the open reading frame at the 5' end of the mRNA and a transcription terminator sequence located just downstream of the open reading frame at the 3' end of the mRNA. A homologous transcribable region can include, but is not limited to, genomic DNA, cDNA, semisynthetic, synthetic, and recombinant nucleic acid sequences.

In the methods of the present invention, the transcribable region with homology to the target gene may be identical in sequence to the corresponding region of the target gene (i.e., 100% sequence identity) or may be a homologue to the corresponding region of the target gene.

The degree of sequence identity between the transcribable region and the corresponding region of the target gene required to achieve silencing of expression of the target gene will likely depend on the target gene. The smaller the transcribable region's nucleotide sequence is relative to the entire target gene, the degree of sequence identity between the sequences should preferably be very high or identical. The larger the transcribable region's nucleotide sequence is relative to the entire target gene, the degree of sequence identity between the sequences can likely be lower.

In the methods of the present invention, the degree of sequence identity of the transcribable region's nucleotide sequence to the corresponding region of the target gene is at least 65%, e.g., at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. For purposes of the present invention, the degree of sequence identity between two nucleic acid sequences is determined as defined herein.

Alternatively, the ability of the transcribable region and the corresponding region of the target gene to hybridize to each other under various stringency conditions can also provide an indication of the degree of relatedness required for silencing expression of a target gene. However, it should be recognized that the lower the stringency conditions required, e.g., low stringency, to achieve hybridization between the homologue and the corresponding region of the target gene, silencing expression of the target gene will likely be less efficient.

In one aspect, the transcribable region and the corresponding region of the target gene hybridize under low stringency conditions. In another aspect, the transcribable region and the corresponding region of the target gene hybridize under medium stringency conditions. In another aspect, the transcribable region and the corresponding region of the target gene hybridize under medium-high stringency conditions. In another aspect, the transcribable region and the corresponding region of the target gene hybridize under high stringency conditions. In another aspect, the transcribable region and the corresponding region of the target gene hybridize under very high stringency conditions.

For probes of about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390)

in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For probes of about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

The first transcribable region preferably consists of at least 19 nucleotides, e.g., at least 40 nucleotides, at least 60 nucleotides, at least 80 nucleotides, at least 100 nucleotides, or at least 200 nucleotides. The first transcribable region can also consist of the entire open reading frame of the first target gene or a homologue thereof.

The second transcribable region preferably consists of at least 19 nucleotides, e.g., at least 40 nucleotides, at least 60 nucleotides, at least 80 nucleotides, at least 100 nucleotides, or at least 200 nucleotides. The second transcribable region can also consist of the entire open reading frame of the second target gene or a homologue thereof.

The third transcribable region having no effective homology to the first and second target genes, may have no homology to the host genome, as described below, or may have homology to a third target gene. The third transcribable region preferably consists of at least 19 nucleotides, e.g., at least 40 nucleotides, at least 60 nucleotides, at least 80 nucleotides, at least 100 nucleotides, at least 250 nucleotides, at least 500 nucleotides, at least 750 nucleotides, or at least 1000 nucleotides. The third transcribable region can also consist of the entire open reading frame of the third target gene or a homologue thereof.

Non-Homologous Transcribable Region

The double-stranded transcribable nucleic acid construct also comprises a third transcribable region with no effective homology to the first and second target genes, wherein the third transcribable region comprises two segments complementary to each other in reverse orientation. In this aspect of the invention, the third transcribable region has no effective homology to the host genome.

In one aspect, the third transcribable region is any transcribable part of any gene, such as the 5'-untranslated region, the coding sequence, or the 3'-untranslated region of a gene, which has no effective homology to the target genes or the host genome.

In another aspect, the third transcribable region corresponds to the coding sequence of a gene with no effective homology to the target genes or the host genome.

In another aspect, the third transcribable region corresponds to the 5'-untranslated region of a gene with no effective homology to the target genes or the host genome.

In another aspect, the third transcribable region corresponds to the 3'-untranslated region of a gene with no effective homology to the target genes or the host genome.

In another aspect, the third transcribable region is a portion of a non-endogenous gene, which has no effective homology to the target genes or the host genome, e.g., the hygromycin resistance gene of E. coli.

The third transcribable region preferably consists of at least 19 nucleotides, e.g., at least 40 nucleotides, at least 60 nucleotides, at least 80 nucleotides, at least 100 nucleotides, at least 250 nucleotides, at least 500 nucleotides, at least 750 nucleotides, or at least 1000 nucleotides.

The two segments complementary to each other in reverse orientation can be separated by a polynucleotide linker. The linker preferably consists of at least 4 nucleotides, e.g., at least 20 nucleotides, at least 40 nucleotides, at least 60 nucleotides, at least 80 nucleotides, at least 100 nucleotides, at least 250 nucleotides, or at least 500 nucleotides.

Target Genes

The target gene encoding a biological substance can be any gene encoding a substance having a biological activity or any gene encoding a polypeptide having biological activity involved in the biosynthesis of a metabolite. The biological substance may be RNA (e.g., ncRNA, rRNA, tRNA, miRNA, or mRNA). The biological substance may also be a polypeptide having a biological activity. The biological substance may also be a metabolite. The biological substance may be native or foreign to the filamentous fungal strain. A native substance is a substance that is from the same filamentous fungal strain. A foreign substance is a substance that is not native to the cell; or a native substance to which structural modifications have been made to alter the native substance.

In one aspect, the biological substance is a polypeptide having biological activity. The polypeptide may be any polypeptide having a biological activity. The term "polypeptide" is not meant herein to refer to a specific length of the encoded product and, therefore, encompasses peptides, oligopeptides, polypeptides, and proteins. The term "polypeptide" also encompasses two or more polypeptides combined to form the encoded product. Polypeptides also include hybrid polypeptides, which comprise a combination of partial or complete polypeptide sequences obtained from at least two different polypeptides wherein one or more (e.g., several) may be heterologous to the filamentous fungal cell. Polypeptides further include naturally occurring allelic and engineered variations of the above-mentioned polypeptides and hybrid polypeptides.

In another aspect, the polypeptide is an antibody, antigen, antimicrobial peptide, enzyme, growth factor, hormone, immunodilator, neurotransmitter, receptor, reporter protein, structural protein, and transcription factor.

In another aspect, the polypeptide is an enzyme. In another aspect, the enzyme is an oxidoreductase, transferase, hydrolase, lyase, isomerase, or ligase. In another aspect, the enzyme is an acetylxylan esterase, aminopeptidase, amylase, carbohydrase, carboxypeptidase, catalase, cellulase, chitinase, cutinase, cyclodextrin glycosyltransferase, deoxyribonuclease, esterase, ferulic acid esterase, alpha-galactosidase, beta-galactosidase, glucoamylase, glucocerebrosidase, alpha-glucosidase, beta-glucosidase, invertase, laccase, lipase, mannosidase, mutanase, oxidase, pectinolytic enzyme, peroxidase, phospholipase, phytase, polyphenoloxidase, proteolytic enzyme, ribonuclease, transglutaminase, urokinase, or xylanase.

In another aspect, the polypeptide is an albumin, collagen, tropoelastin, elastin, or gelatin; or a variant or hybrid thereof.

The biological substance may also be the product of a selectable marker. A selectable marker is a gene the product of which provides for biocide or viral resistance, resistance to heavy metals, prototrophy to auxotrophs, and the like. Selectable markers include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), beta-tubulin variant (Seip et al., 1990, Appl. Environ. Microbiol. 56(12): 3686-3692; Yan and Dickman, 1996, Appl. Environ. Microbiol. 62(8): 3053-3056), fcy1 (cytosine deaminase), hemA (5-aminolevulinate synthase), hph (hygromycin phosphotransferase), niaD (nitrate reductase), pyrG (orotidine-5'-phosphate decarboxylase), sC (sulfate adenyltransferase), trpC (anthranilate synthase), and tk (thymidine kinase), as well as equivalents thereof. It is understood herein that some of the selectable markers above, e.g., pyrG, are used for counter-selection. Counter-selection is defined as growth dependent on targeted inactivation of such a selectable marker.

In practicing the methods of the present invention, the target gene may be isolated as described herein.

In one aspect, expression of a target gene is reduced by at least 20%, e.g., at least 30%, at least 40%, at least 50%, at least 60%, at least 70%, at least 80%, at least 90%, or 100%.

Where it is desired to use a target sequence within the 5' untranslated region, the coding sequence, or the 3' untranslated region, gene silencing nucleic acid constructs or vectors constructed with inverted repeats within any one of these regions may additionally enable the silencing of genes that are homologous to the coding sequence present in the silencing vector. When it is, therefore, desired to silence homologues of a gene within an organism, the construction of a silencing vector containing a transitive expressed target sequence having homology within the 5' untranslated region, the coding sequence, or the 3' untranslated region may allow the elimination or reduction of expression of one or more (e.g., several) genes exhibiting sequence homology to the coding sequence within the construct. The term "homology" or "homologous" usually denotes those sequences that are of some common ancestral structure and exhibit a high degree of sequence similarity or identity of the active regions.

In one aspect, the interfering RNA interacts with RNA transcripts of one or more (e.g., several) homologues of the target gene to silence expression of the one or more homologues of the target gene.

In another aspect, expression of one or more (e.g., several) homologues of the target gene is reduced by at least 20%, e.g., at least 30%, at least 40%, at least 50%, at least 60%, at least 70%, at least 80%, at least 90%, or 100%.

Phenotypic Markers

In practicing the methods of the present invention, RNA transcripts of the double-stranded transcribable nucleic acid construct are converted to the siRNAs, which can interact with RNA transcripts of the first target gene resulting in a phenotypic change of the transformed filamentous fungal host cell. When the first target gene is silenced, the silencing confers a characteristic or trait on the host cell that can be readily identified, screened, or selected. The first target gene, i.e., phenotypic marker, may confer an observable trait including, but not limited to, apoptosis, cell death, cell cycle, colony morphology, colony color, development, down-regulation of a gene, growth/lack of growth on specific nutrients, up-regulation of a gene, pathogenicity, resistance to drugs or toxic metabolites, spore formation, or spore color.

The phenotypic change can be any change in an observable characteristic of a strain that distinguishes it from a parental or reference strain, such as a change in one of the traits described above.

In one aspect, the first target gene is a wA (polyketide synthase; accession number XP_001393884) gene. In another aspect, the first target gene is a brlA (transcriptional regulator of conidiophores development; accession number XP_001389479) gene. In another aspect, the first target gene is a pepC (subtilisin-like serine protease; accession number XP_001391470) gene. In another aspect, the first target gene is an amyR (transcriptional regulator of genes for starch/maltose utilization; accession number XP_001402052) gene. In another aspect, the first target gene is a xlnR (transcriptional activator of cellulolytic and xylanolytic enzymes; accession number XP_001397110) gene. In another aspect, the first target gene is a pyrG (orotidine-5'-phosphate decarboxylase; accession number X06626.1) gene. In another aspect, the first target gene is a bipA (endoplasmic reticulum chaperone; accession number Y08868.1) gene. In another aspect, the first target gene is a tpa (Apoptosis inducing factor) gene. In another aspect, the first target gene is a rad1 (cell cycle checkpoint protein) gene. In another aspect, the first target gene is a lae1 (methyltransferase associated with regulation of secondary metabolites; accession number XP_001402055) gene. In another aspect, the first target gene is an amdS (acetamidase) gene. In another aspect, the first target gene is an argB (ornithine carbamoyltransferase) gene. In another aspect, the first target gene is a bar (phosphinothricin acetyltransferase) gene. In another aspect, the first target gene is a hph (hygromycin phosphotransferase) gene. In another aspect, the first target gene is a niaD (nitrate reductase) gene. In another aspect, the first target gene is a sC (sulfate adenyltransferase) gene. In another aspect, the first target gene is a trpC (anthranilate synthase) gene. In another aspect, the first target gene is a fcy1 (cytosine deaminase) gene.

The first target gene may also be adeA (phosphoribosyl-aminoimidazole-succinocarboxamide synthase), adeB (phosphoribosyl-aminoimidazole synthase), hemA (5-aminolevulinate synthase), tk (thymidine kinase), or trp5 (tryptophan synthase), as well as equivalents thereof.

The accession numbers mentioned above are incorporated herein in their entirety.

Filamentous Fungal Strains

The present invention also relates to filamentous fungal strains comprising a double-stranded transcribable nucleic acid construct comprising a promoter operably linked to a first polynucleotide comprising a first transcribable region with homology to a first target gene encoding a first biological substance, a second polynucleotide comprising a second transcribable region with homology to a second target gene encoding a second biological substance, and a third polynucleotide comprising a third transcribable region with no effective homology to the first and second target genes wherein the third transcribable region comprises two segments complementary to each other in reverse orientation; wherein the first, second, and third transcribable regions are transcribed as a single-stranded RNA molecule; and wherein production of short interfering RNAs (siRNAs), comprising sequences of the target genes to be silenced, is by cultivating the filamentous fungal strain under conditions to produce RNA transcripts of the double-stranded transcribable nucleic acid construct that are then converted to the siRNAs, which interact with RNA transcripts of the target genes to silence expression of the target genes encoding the first and second biological substances. The double-stranded transcribable nucleic acid construct may further comprise at least one additional polynucleotide comprising a transcribable region with homology to an additional target gene encoding an additional biological substance, as described herein.

The filamentous fungal strain may be any filamentous fungal strain useful in the methods of the present invention. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevi-*

*siae* is by budding of a unicellular thallus and carbon catabolism may be fermentative.

In one aspect, the filamentous fungal strain is an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* strain.

In another aspect, the filamentous fungal strain is an *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Bjerkandera adusta*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Coprinus cinereus*, *Coriolus hirsutus*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* strain.

In another aspect, the filamentous fungal strain is an *Aspergillus oryzae* strain. In another aspect, the *Aspergillus oryzae* strain is *Aspergillus oryzae* strain deposit no. IFO 4177.

In another aspect, the filamentous fungal strain is a *Fusarium venenatum* strain. In another aspect, the *Fusarium venenatum* strain is *Fusarium venenatum* A3/5, which was originally deposited as *Fusarium graminearum* ATCC 20334 and recently reclassified as *Fusarium venenatum* by Yoder and Christianson, 1998, *Fungal Genetics and Biology* 23: 62-80 and O'Donnell et al., 1998, *Fungal Genetics and Biology* 23: 57-67; as well as taxonomic equivalents of *Fusarium venenatum* regardless of the species name by which they are currently known. In another aspect, the *Fusarium venenatum* strain is a morphological mutant of *Fusarium venenatum* A3/5 or *Fusarium venenatum* ATCC 20334, as disclosed in WO 97/26330.

In another aspect, the filamentous fungal strain is a *Trichoderma reesei* strain. In another aspect, the *Trichoderma reesei* strain is *Trichoderma reesei* ATCC 56765. In another aspect, the *Trichoderma reesei* strain is *Trichoderma reesei* RutC30. In another aspect, the *Trichoderma reesei* strain is *Trichoderma reesei* TV10. In another aspect, the *Trichoderma reesei* strain is a mutant of *Trichoderma reesei* RutC30. In another aspect, the *Trichoderma reesei* strain is a mutant of *Trichoderma reesei* TV10. In another aspect, the *Trichoderma reesei* strain is a morphological mutant of *Trichoderma reesei*. See, for example, WO 97/26330, which is incorporated herein by reference in its entirety.

In another aspect, the filamentous fungal strain is an *Aspergillus niger* strain. In another aspect, the *Aspergillus niger* strain is *Aspergillus niger* Bo-1 (DSM 12665). In another aspect, the *Aspergillus niger* strain is a mutant of *Aspergillus niger* Bo-1 (DSM 12665), as disclosed in WO 2004/090155.

Filamentous fungal strains may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787.

Silencing expression of a target gene encoding an undesirable biological substance may be detected using methods known in the art that are specific for the targeted biological substance. These detection methods may include use of specific antibodies, high performance liquid chromatography, capillary electrophoresis, formation of an enzyme product, disappearance of an enzyme substrate, SDS-PAGE, or loss or appearance of a phenotype, e.g., spore color. For example, an enzyme assay may be used to determine the activity of the enzyme. Procedures for determining enzyme activity are known in the art for many enzymes (see, for example, D. Schomburg and M. Salzmann (eds.), *Enzyme Handbook*, Springer-Verlag, New York, 1990).

Methods of Production

The present invention also relates to methods of producing a biological substance of interest, comprising: (a) cultivating a filamentous fungal strain under conditions conducive for production of the biological substance of interest, wherein the filamentous fungal strain comprises a double-stranded transcribable nucleic acid construct comprising a promoter operably linked to a first polynucleotide comprising a first transcribable region with homology to a first target gene encoding a first biological substance, a second polynucleotide comprising a second transcribable region with homology to a second target gene encoding a second biological substance, and a third polynucleotide comprising a third transcribable region with no effective homology to the first and second target genes, wherein the third transcribable region comprises two segments complementary to each other in reverse orientation and the first, second, and third transcribable regions are transcribed as a single-stranded RNA molecule, wherein production of short interfering RNAs (siRNAs), comprising sequences of the target genes to be silenced, is by cultivating the filamentous fungal strain under conditions to produce RNA transcripts of the double-stranded transcribable nucleic acid construct that are then converted to the siRNAs comprising sequences of the target genes to be silenced, which interact with RNA transcripts of the target genes to silence expression of the target genes encoding the first and second biological substances; and wherein the filamentous fungal strain comprises a fourth polynucleotide encoding the biological substance of interest; and optionally (b) recovering the biological substance of interest from the cultivation medium. The double-stranded transcribable nucleic acid construct may further comprise at least one additional polynucleotide comprising a transcribable region with homology to an additional target gene encoding an additional biological substance, as described herein.

The biological substance of interest may be any biological substance. In one aspect, the biological substance of interest is RNA (e.g., ncRNA, rRNA, tRNA, miRNA, or mRNA). In another aspect, the biological substance of interest is an antibody, antigen, antimicrobial peptide, enzyme, growth factor, hormone, immunodilator, neurotransmitter, receptor, reporter protein, structural protein, and transcription factor. In another aspect, the biological substance of interest is an enzyme. In another aspect, the enzyme is an oxidoreductase, transferase, hydrolase, lyase, isomerase, or ligase. In another aspect, the enzyme is an acetylxylan esterase, aminopeptidase, amylase, carbohydrase, carboxypeptidase, catalase, cellulase, chitinase, cutinase, cyclodextrin glycosyltransferase, deoxyribonuclease, esterase, ferulic acid esterase, alpha-galactosidase, beta-galactosidase, glucoamylase, glucocerebrosidase, alpha-glucosidase, beta-glucosidase, invertase, laccase, lipase, mannosidase, mutanase, oxidase, pectinolytic enzyme, peroxidase, phospholipase, phytase, polyphenoloxidase, proteolytic enzyme, ribonuclease, transglutaminase, urokinase, or xylanase.

The biological substance of interest may be native or foreign to the filamentous fungal strain. The silencing of expression of the target genes encoding the first and second biological substances can lead to increased expression of another biological substance of interest. Consequently, the silencing of expression of the first and second biological substances could directly affect production or expression of a biological substance of interest. For example, the first and second biological substances may be proteases that degrade the biological substance of interest thereby lowering the amount of the biological substance of interest produced. By silencing expression of the proteases, more of the biological substance of interest will be expressed and produced. Or, the first and second biological substances may share a cellular process or processes, e.g., transcription factor or secretory pathway, with the biological substance of interest thereby lowering the amount of the biological substance of interest produced. By silencing expression of the first and second biological substances, more of the cellular process or processes will be available to the biological substance of interest, e.g., expression-limiting transcription elements, thereby increasing the amount of the biological substance of interest expressed and produced. Moreover, the first and second biological substances may be toxins that contaminate the biological substance of interest preventing use of the biological substance of interest in a particular application, e.g., an enzyme in a food process.

In the production methods of the present invention, the filamentous fungal strains are cultivated in a nutrient medium suitable for production of the biological substance of interest using methods known in the art. For example, the strains may be cultivated by shake flask cultivation, and small-scale or large-scale fermentation (including continuous, batch, fed-batch, or solid state fermentations) in laboratory or industrial fermentors performed in a suitable medium and under conditions allowing the biological substance to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the biological substance is secreted into the nutrient medium, it can be recovered directly from the medium. If the biological substance is not secreted, it can be recovered from cell lysates.

The biological substance of interest may be detected using methods known in the art that are specific for the biological substances. These detection methods may include use of specific antibodies, high performance liquid chromatography, capillary chromatography, formation of an enzyme product, disappearance of an enzyme substrate, or SDS-PAGE. For example, an enzyme assay may be used to determine the activity of the enzyme. Procedures for determining enzyme activity are known in the art for many enzymes (see, for example, D. Schomburg and M. Salzmann (eds.), *Enzyme Handbook*, Springer-Verlag, New York, 1990).

The resulting biological substance of interest may be isolated using methods known in the art. For example, a polypeptide of interest may be isolated from the cultivation medium by conventional procedures including, but not limited to, centrifugation, filtration, extraction, spray-drying, evaporation, or precipitation. The isolated polypeptide may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., *Protein Purification*, J.-C. Janson and Lars Ryden, editors, VCH Publishers, New York, 1989). A metabolite of interest may be isolated from a cultivation medium by, for example, extraction, precipitation, or differential solubility, or any method known in the art. The isolated metabolite may then be further purified using methods suitable for metabolites.

Polynucleotides Encoding a Biological Substance

An isolated polynucleotide sequence encoding a biological substance of interest may be obtained from any prokaryotic, eukaryotic, or other source. For purposes of the present invention, the term "obtained from" as used herein in connection with a given source shall mean that the biological substance is produced by the source or by a cell in which a gene from the source has been inserted.

The techniques used to isolate or clone a polynucleotide encoding a biological substance of interest are known in the art and include isolation from genomic DNA, preparation from cDNA, or a combination thereof. The cloning of the polynucleotide from such genomic DNA can be effected, e.g., by using the well-known polymerase chain reaction (PCR). See, for example, Innis et al., 1990, *PCR Protocols: A Guide to Methods and Application*, Academic Press, New York. The cloning procedures may involve excision and isolation of a desired nucleic acid fragment comprising the polynucleotide encoding the biological substance, insertion of the fragment into a vector molecule, and incorporation of the recombinant vector into the mutant filamentous fungal cell where multiple copies or clones of the nucleic acid sequence will be replicated. The polynucleotide may be of genomic, cDNA, RNA, semisynthetic, synthetic origin, or any combinations thereof.

Nucleic Acid Constructs

An isolated polynucleotide encoding a biological substance of interest may be contained in a nucleic acid construct in the filamentous fungal strain. A nucleic acid construct comprises a nucleotide sequence encoding the biological substance of interest operably linked to at least one promoter and one or more control sequences that direct expression of the nucleotide sequence in a filamentous fungal strain under conditions compatible with the control sequences. Expression will be understood to include any step involved in the production of the biological substance of interest including, but not limited to, transcription, post-transcriptional modification, translation, post-translational modification, and secretion.

The isolated polynucleotide encoding the biological substance of interest may be further manipulated in a variety of ways to provide for expression of the biological substance. Manipulation of the nucleotide sequence prior to its insertion into a vector may be desirable or necessary depending on the expression vector. The techniques for modifying nucleotide sequences utilizing recombinant DNA methods are well known in the art.

The polynucleotide may comprise one or more native control sequences or one or more of the native control sequences may be replaced with one or more control sequences foreign to the nucleotide sequence for improving expression of the coding sequence in a host cell. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a biological substance of interest.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dana (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal strains are obtained from the genes for *Aspergillus oryzae* TAKA amylase, *Aspergillus nidulans* triose phosphate isomerase, *Fusarium venenatum* trypsin, and *Fusarium venenatum* glucoamylase.

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

A polynucleotide encoding a biological substance of interest may be contained in a recombinant expression vector comprising a promoter, the nucleotide sequence encoding the biological substance, and transcriptional and translational stop signals. The various nucleic acids and control sequences described herein may be joined together to produce a recombinant expression vector that may include one or more (e.g., several) convenient restriction sites to allow for insertion or substitution of the nucleotide sequence encoding the polypeptide at such sites. Alternatively, a polynucleotide sequence may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (e.g., several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), beta-tubulin variant (Seip et al., 1990, supra; Yan and Dickman, 1996, supra, fcy1 (cytosine deaminase), hemA (5-aminolevulinate synthase), hph (hygromycin phosphotransferase), niaD (nitrate reductase), pyrG (orotidine-5'-phosphate decarboxylase), sC (sulfate adenyltransferase), trpC (anthranilate synthase), and tk (thymidine kinase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. In addition, the host cell may be modified in a locus selected from the group consisting of ku70, ku80, rad50, mre11, xrs2, lig4, and sir4, and functional equivalents thereof, where the frequency of non-homologous recombination has been decreased. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors are well known to one skilled in the art (see, e.g., Sambrook et al., 1989, *Molecular Cloning, A Laboratory Manual*, 2d edition, Cold Spring Harbor, N.Y.).

The present invention is further described by the following examples that should not be construed as limiting the scope of the invention.

EXAMPLES

Strains

*Aspergillus niger* strain C2111 contains three copies of the *Trametes cingulata* amyloglucosidase (glucoamylase) gene (WO 2006/069289) introduced at three loci (SP288, NA1, and NA2), and is derived from *Aspergillus niger* strain C40 which was isolated from soil in the 1960's, of which amyloglucosidase activity has been enhanced by mutagenesis.

*Aspergillus niger* strain M1137 is a uridine-requiring (pyrG−) isolate derived from *Aspergillus niger* strain C2111.

*Aspergillus niger* strain JoanTc3 contains three copies of the *Trametes cingulata* amyloglucosidase gene introduced at three distinct loci (SP288, NA1, and NA2), and is derived from *Aspergillus niger* strain Bo-1 (DSM 12665). *Aspergillus niger* strain Bo-1 is derived from *Aspergillus niger* strain C40.

*Aspergillus niger* strain JoanTc3ΔpyrG is a uridine-requiring (pyrG−) isolate derived from *Aspergillus niger* strain JoanTc3.

*Aspergillus niger* strain EvFz5 is a uridine-requiring (pyrG−) isolate expressing RNA dependent RNA polymerase (RdRP) and is derived from *Aspergillus niger* strain JoanTc3ΔpyrG.

*Aspergillus oryzae* HowB104 (U.S. Pat. No. 5,770,418) is a strain in which the native TAKA amylase gene has been replaced with the pyrG gene resulting in a pyrimidine prototroph.

*Aspergillus niger* C1650 is a parent strain of *Aspergillus niger* NN059095 which is described in WO 2012/160093. *Aspergillus niger* NN059095 is a uridine-requiring (pyrG−) isolate derived from *Aspergillus niger* strain C1650 and was genetically modified to disrupt expression of amyloglucosidase activities.

*Aspergillus oryzae* strain DSY10 (U.S. Pat. No. 5,770,418) contains multiple copies of the *Trametes villosa* (synonym: *Polyporus pinsitus*) laccase gene and is derived from *Aspergillus oryzae* HowB104.

*Aspergillus oryzae* strain DSY10ΔpyrG is a uridine-requiring (pyrG−) isolate derived from *Aspergillus oryzae* strain DSY10.

Media and Solutions

AMG trace metals solution was composed of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.H_2O$, 3.0 g of citric acid, and deionized water to 1 liter.

COVE salt solution was composed of 26 g of KCl, 26 g of $MgSO_4.7H_2O$, 76 g of $KH_2PO_4$, 50 ml of COVE trace metals solution, and deionized water to 1 liter.

COVE trace metals solution was composed of 0.04 g of $NaB_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, 10 g of $ZnSO_4.7H_2O$, and deionized water to 1 liter.

COVE-N-gly agar plates were composed of 50 ml of COVE salt solution, 218 g of sorbitol, 10 g of glycerol, 2.02 g of $KNO_3$, 25 g of Agar Noble, and deionized water to 1 liter.

COVE-N-JP top agarose was composed of 342.3 g of sucrose, 3 g of $NaNO_3$, 20 ml of COVE salt solution, 15 g of Low Melt Agarose (Sigma-Aldrich, St. Louis, Mo., USA), and deionized water to 1 liter.

COVE-N-JP transformation agar plates were composed of 342.3 g of sucrose, 3 g of $NaNO_3$, 20 ml of COVE salt solution, 30 g of Agar Noble, and deionized water to 1 liter.

LB agar was composed of 10 g of tryptone, 5 g of yeast extract, 5 g of NaCl, 15 g of BACTO™ agar, and deionized water to 1 liter.

Minimal medium transformation plates were composed of 342.3 g of sucrose, 50 ml of 20× Minimal medium salt solution, 1 ml of COVE trace metals solution, 20 ml of 50% glucose, 20 ml of a 0.02% biotin solution, 2.5 ml of 20% $MgSO_4.7H_2O$, 20 g of Agar Noble, and deionized water to 1 liter.

Minimal medium agar plates were composed of 6 g of $NaNO_3$, 0.52 g of KCl, 1.52 g of $KH_2PO_4$, 1 ml of COVE trace metals solution, 20 ml of 50% glucose, 20 ml of a 0.02% biotin solution, 2.5 ml of 20% $MgSO_4.7H_2O$, 20 g of Agar Noble, and deionized water to 1 liter.

20× Minimal medium salt solution was composed of 120 g of $NaNO_3$, 10.4 g of KCl, 30.4 g of $KH_2PO_4$, and deionized water to 1 liter.

MLC medium was composed of 40 g of glucose, 50 g of soy bean powder, 4 g of citric acid, 2 drops of antifoam, and deionized water to 1 liter; pH 6.0.

MU-1 medium was composed of 260 g of maltodextrin, 3 g of $MgSO_4.7H_2O$, 6 g of $K_2SO_4$, 5 g of $KH_2PO_4$, 0.5 ml of AMG trace metals solution, 2 drops of antifoam, and deionized water to 1 liter; pH 4.5.

MY25 medium was composed of 25 g of maltodextrin, 2 g of $MgSO_4.7H_2O$, 10 g of $KH_2PO_4$, 2 g of anhydrous citric acid, 2 g of $K_2SO_4$, 2 g of urea, 10 g of yeast extract, 0.5 ml of AMG trace metals solution, and deionized water to 1 liter.

PDA plates were composed of 39 g of DIFCO™ Potato Dextrose Agar (Becton Dickinson and Co., Sparks, Md., USA) and deionized water to 1 liter.

SPTC solution was composed of 40% polyethylene glycol 4000 (PEG 4000; Sigma-Aldrich Chemical Co., Inc., St. Louis, Mo., USA), 0.8 M sorbitol, 50 mM $CaCl_2$, and 50 mM Tris-HCl; pH 8.0, filter sterilized.

STC solution was composed of 0.8 M sorbitol, 50 mM $CaCl_2$, and 50 mM Tris-HCl; pH 8.0, filter sterilized.

TAE buffer was composed of 4.84 g of Tris Base, 1.14 ml of glacial acetic acid, 2 ml of 0.5 M EDTA, and deionized water to 1 liter; pH 8.0.

2XYT agar was composed of 16 g of tryptone, 10 g of yeast extract, 5 g of NaCl, 15 g of BACTO™ agar, and deionized water to 1 liter.

YP medium was composed of 10 g of BACTO™ yeast extract (Becton Dickinson and Co., Sparks, Md., USA), 20 g of BACTO™ peptone (Becton Dickinson and Co., Sparks, Md., USA), and deionized water to 1 liter.

Example 1

Construction of pEvFz34

A 730 bp fragment comprising the *Aspergillus oryzae* tef-1 promoter region (Kitamoto et al., 1998, *Applied Microbiology and Biotechnology* 50: 85-92) was amplified by PCR using the primers shown below where the 5' ends of both primers were engineered to contain 20 bp of homologous sequence to the ends of the linearized vector pAILo2 (WO 2004/099228).

```
Primer 067500 (sense):
                                            (SEQ ID NO: 1)
5'-GAGTCAGTGAGCGAGGAAGCACTGTGGACCAGACAGGCGCCA-3'

Primer 067501 (antisense):
                                            (SEQ ID NO: 2)
5'-CTGCGGCCGCGGGCCCATGGTGCTCAGATACTACGGCTGATC-3'
```

*Aspergillus oryzae* tef-1 promoter is denoted by underlined letters.

The amplification reaction was composed of 1× THERMOPOL™ Reaction Buffer (New England Biolabs, Beverly, Mass., USA), 1 mM dNTPs, 20 ng of pSaMF2049004 (SEQ ID NO: 3), 50 pmoles of sense primer 067500, 50 pmoles of antisense primer 067501, and 2.5 units of Taq DNA polymerase (New England Biolabs, Beverly, Mass., USA) in a total volume of 50 μl. The reaction was incubated in an EPPENDORF® MASTERCYCLER® 5333 (Eppendorf AG, Hamburg, Germany) programmed for 1 cycle at 94° C. for 3 minutes; 30 cycles each at 94° C. for 30 seconds, 56° C. for 30 seconds, and 72° C. for 45 seconds; a final extension at 72° C. for 7 minutes; and a hold at 10° C. The PCR product was purified by 1% agarose gel electrophoresis using TAE buffer where a band of 730 bp was excised from the gel and further purified using a MINELUTE® Gel Extraction Kit (QIAGEN Inc., Valencia, Calif., USA) according to the manufacturer's protocol.

Plasmid pAILo2 was digested with Sap I and Nco I and purified by 1% agarose gel electrophoresis using TAE buffer, excised from the gel, and further purified using a QIAQUICK® Gel Extraction Kit (QIAGEN Inc., Valencia, Calif., USA) according to the manufacturer's protocol.

The 730 bp PCR product was cloned into the Sap I/Nco I digested pAILo2 using an IN-FUSION™ Advantage PCR Cloning Kit (Clontech, Mountain View, Calif., USA). The cloning reaction was composed of 1× IN-FUSION™ Reaction Buffer (Clontech, Mountain View, Calif., USA), 1×BSA (Clontech, Mountain View, Calif., USA), 88 ng of Sap I/Nco I digested pAILo2 vector, 100 ng of the 730 bp PCR product, and 20 units of IN-FUSION™ Enzyme (Clontech, Mountain View, Calif., USA) in a total volume of 20 μl. The mixture was incubated at 37° C. for 15 minutes, 50° C. for 15 minutes, and then placed on ice.

One microliter of the cloning reaction was transformed into ONE SHOT® TOP10 chemically competent *Escherichia coli* cells (Invitrogen Corp., Carlsbad, Calif., USA) according to the manufacturer's protocol. Transformants were selected on 2XYT agar plates containing 100 μg of ampicillin per ml. Plasmid DNA samples from several transformants were purified using a BIOROBOT® 9600 (QIAGEN Inc., Valencia, Calif., USA) and analyzed by DNA sequencing using a 3130xl Genetic Analyzer (Applied Biosystems, Foster City, Calif., USA) to identify plasmids containing the desired tef-1 promoter insert. One plasmid with the correct DNA sequence was designated pEvFz34 (FIG. 1).

Example 2

Construction of Plasmid pEvFz35

Plasmid pEvFz35 was constructed to contain the *Aspergillus oryzae* tef-1 promoter, an inverted repeat (hph-IR) derived from a portion of the *Escherichia coli* hygromycin phosphotransferase gene (hph) (Kaster et al., 1983, *Nucleic Acids Res.* 11: 6895-6911; WO 2008/080017), the *Aspergillus niger* amyloglucosidase (AMG) terminator (Hata et al., 1991, *Agric. Biol. Chem.* 55: 941-949), and the *Aspergillus nidulans* orotidine-5'-phosphate decarboxylase (pyrG) gene as a selectable marker (Oakley et al., 1987, *Gene* 61: 385-399).

Plasmid pEvFz35 was generated by cloning the hph inverted repeat (hph-IR) from pDM266 (WO 2008/080017). Plasmids pEvFz34, described in Example 1, and pDM266 were digested with Not I and Pac I overnight at 37° C. The resulting 4923 bp linearized pEvFz34 vector fragment and the 505 bp hph-IR insert from pDM266 were purified by 0.7% agarose gel electrophoresis using TAE buffer, excised from the gel, and further purified using a QIAQUICK® Gel Extraction Kit.

The 505 bp hph-IR insert was ligated to the Not I/Pac I digested pEvFz34 fragment using a QUICK LIGATION™ Kit (New England Biolabs, Beverly, Mass., USA). The ligation reaction was composed of 1× QUICK LIGATION™ Reaction Buffer (New England Biolabs, Beverly, Mass., USA), 50 ng of Not I/Pac I digested pEvFz34 vector, 44 ng of the 516 bp Not I/Pac I digested hph-IR insert, and 1 μl of T4 DNA Ligase (New England Biolabs, Beverly, Mass., USA) in a total volume of 20 μl. The ligation mixture was incubated at 37° C. for 15 minutes, 50° C. for 15 minutes, and then placed on ice.

One microliter of the ligation mixture was transformed into SURE® chemically competent *Escherichia coli* cells (Stratagene, La Jolla, Calif., USA) according to the manufacturer's instructions. Transformants were selected on 2XYT agar plates containing 100 μg of ampicillin per ml. Plasmid DNA was purified from several transformants using a BIOROBOT® 9600 and analyzed by digestion with Not I and Pac I to identify plasmids containing the desired hph-IR insert. One putative clone identified as having the correct restriction pattern was sequenced using an EZ:TN™ <TET-1> Insertion Kit (Epicentre Biotechnologies, Madison, Wis., USA), designed to randomly insert transposons tagged with primer binding sites for bidirectional sequencing of recombinant DNA. The transposon insertion reaction was composed of 1×EZ-Tn5™ Reaction Buffer (Epicentre Biotechnologies, Madison, Wis., USA), 0.2 μg of pEvFz35, 0.1 μl of EZ:TN™ <TET-1> Transposon (Epicentre Biotechnologies, Madison, Wis., USA), and 1 μl of EZ-Tn5 Transposase (Epicentre Biotechnologies, Madison, Wis., USA) in a final volume of 10 μl. The reaction mixture was incubated at 37° C. for 2 hours. The insertion reaction was stopped by the addition of 1× Stop Solution (Epicentre Biotechnologies, Madison, Wis., USA) and heating at 70° C. for 10 minutes.

Figure 2:
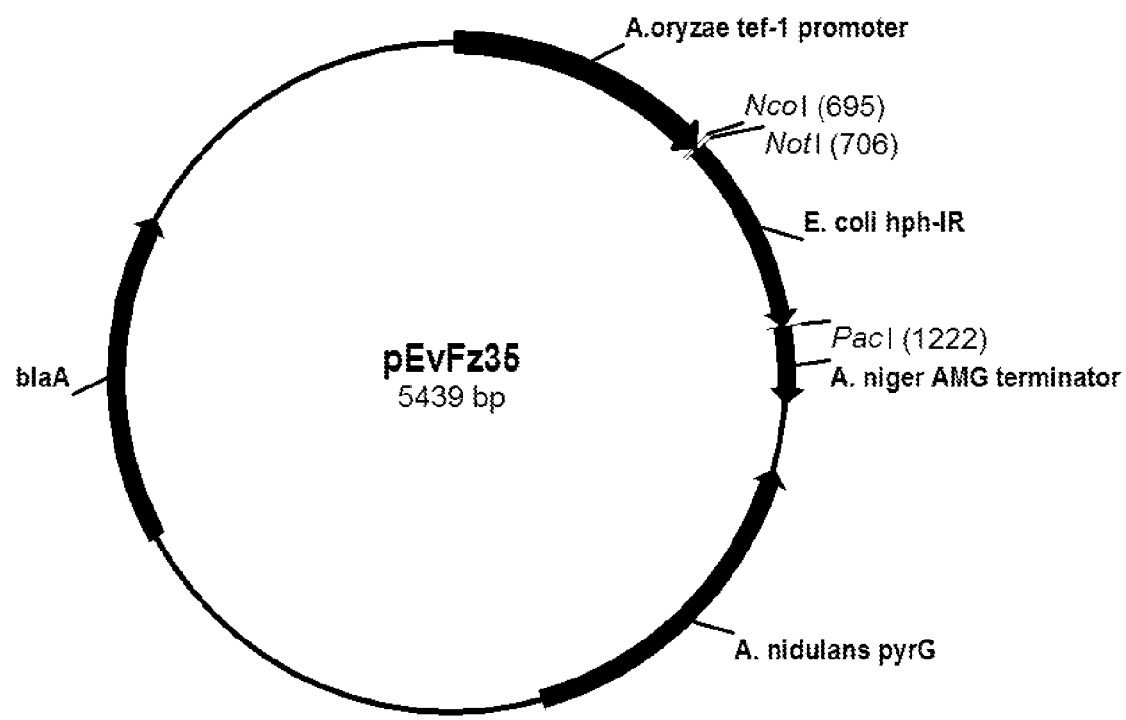
FIG. 2 shows a restriction map of pEvFz35.

ONE SHOT® TOP10 Electrocomp™ *Escherichia coli* cells (Invitrogen Corp., Carlsbad, Calif., USA) were transformed with 1 μl of the transposon targeted DNA mixture according to the manufacturer's protocol. Transformants were selected on LB agar plates containing 10 μg of tetracycline per ml. Plasmid DNA samples from several transformants were purified using a BIOROBOT® 9600 and sequenced bidirectionally using 1.6 pmol of both the TET-1 FP-1 forward primer and TET-1 RP-1 reverse primer (Epicentre Biotechnologies, Madison, Wis., USA) and a 3130xl Genetic Analyzer. The resulting plasmid with the correct DNA sequence was designated pEvFz35 (FIG. 2).

Example 3

Construction of Plasmid pEvFz36

A transitive RNAi vector was constructed for suppressing the expression of an *Aspergillus niger* ATCC 1015 polyketide synthase gene (SEQ ID NO: 4 for the cDNA sequence and SEQ ID NO: 5 for the deduced amino acid sequence; Accession No. XM_001393847.2).

Plasmid pEvFz36 was constructed to contain the *Aspergillus oryzae* tef-1 promoter, a fragment of the open reading frame for the *Aspergillus niger* polyketide synthase gene, the *Escherichia coli* hygromycin phosphotransferase inverted repeat (hph-IR), the *Aspergillus niger* amyloglucosidase (AMG) terminator, and the full-length *Aspergillus nidulans* orotidine-5'-phosphate (pyrG) gene as a selectable marker. The *Aspergillus niger* polyketide synthase gene was chosen as a target for silencing because of its sequence identity to other polyketide synthases involved in conidial pigment biosynthesis in filamentous fungi.

Figure 3:
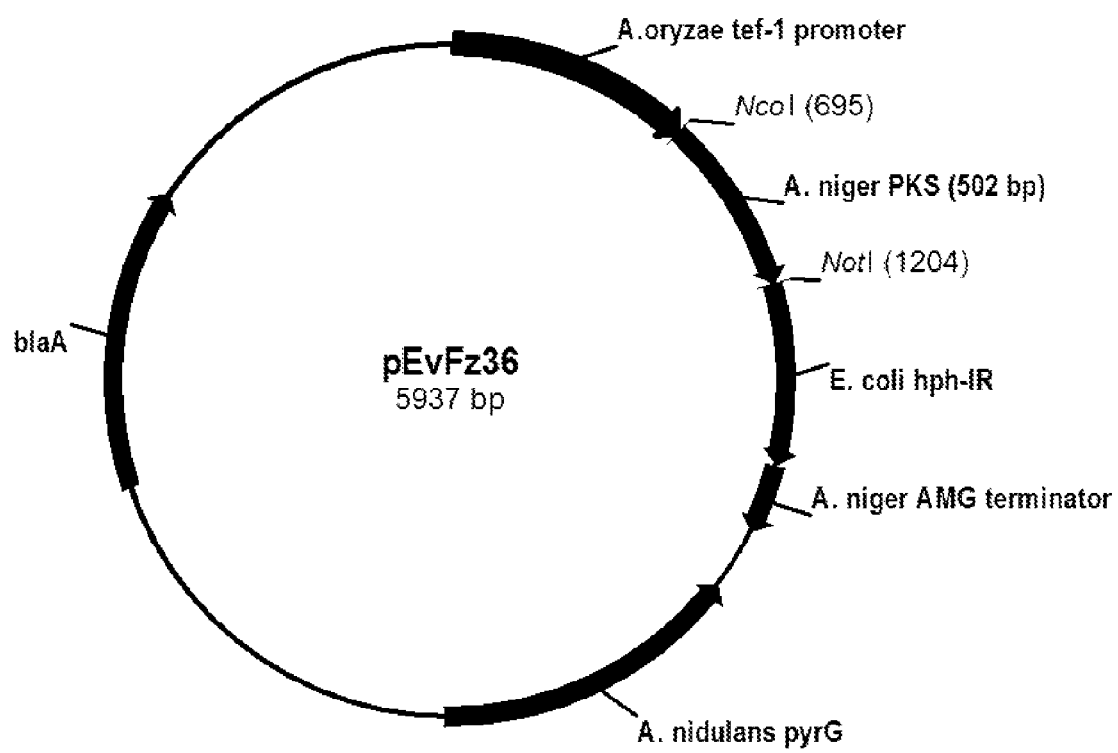
FIG. 3 shows a restriction map of pEvFz36.

A 502 bp fragment from pAmFs031 (WO 2008/080017) was digested with Nco I and Not I, ligated to Nco I/Not I digested pEvFz35 using a QUICK LIGATION™ Kit, and transformed into SURE® chemically competent *Escherichia coli* cells according to the manufacturer's instructions. Transformants were selected on 2XYT agar plates containing 100 μg of ampicillin per ml. Plasmid DNA samples from several transformants were purified using a BIOROBOT® 9600 and analyzed by DNA sequencing using a 3130xl Genetic Analyzer to identify plasmids containing the desired polyketide synthase insert. One plasmid with the expected DNA sequence was designated pEvFz36 (FIG. 3).

Example 4

Construction of Plasmid pHiTe48

A transitive RNAi vector was constructed for co-suppressing the expression of an *Aspergillus niger* ATCC 1015 polyketide synthase gene, described in Example 3, and *Trametes cingulata* amyloglucosidase (AMG) gene (SEQ ID NO: 6 for the cDNA sequence and SEQ ID NO: 7 for the deduced amino acid sequence).

Plasmid pHiTe48 was constructed to contain the *Aspergillus oryzae* tef-1 promoter, a fragment of the open reading frame for the *Aspergillus niger* polyketide synthase gene, a fragment of the open reading frame for the *Trametes cingulata* amyloglucosidase (AMG) gene, the *Escherichia coli* hygromycin phosphotransferase inverted repeat (hph-IR), the *Aspergillus niger* amyloglucosidase (AMG) terminator, and the full-length *Aspergillus nidulans* orotidine-5'-phosphate decarboxylase (pyrG) gene as a selectable marker.

A 200 bp fragment of the *Trametes cingulata* amyloglucosidase open reading frame contained in pHiTe08 (SEQ ID NO: 8) was amplified by PCR using the primers shown below where the 5' ends of both primers were engineered to contain 20 bp of homologous sequence of the ends of the linearized vector pEvFz36 (Example 3).

```
Primer 069733 (sense):
                                       (SEQ ID NO: 9)
5'-GAACCTTACGCGGCCATGCGTTTCACGCTCCTCAC-3'

Primer 069734 (antisense):
                                      (SEQ ID NO: 10)
5'-GAACATCGCGCGGCCGCTTCGGGTTGGATGTGCTCG-3'
```

The amyloglucosidase coding sequence is denoted by underlined letters.

The amplification reaction was composed of 1× GENEAMP® PCR Buffer II (Applied Biosystems, Inc., Foster City, Calif., USA), 0.2 mM dNTPs, 20 ng of pHiTe08, 50 pmoles of sense primer 069733, 50 pmoles of antisense primer 069734, and 5 units of AMPLITAQ GOLD® DNA polymerase (Applied Biosystems, Inc., Foster City, Calif., USA) in a final volume of 50 μl. The reaction was incubated in an EPPENDORF® MASTERCYCLER® 5333 programmed for 1 cycle at 95° C. for 9 minutes; 30 cycles each at 95° C. for 30 seconds, 55° C. for 30 seconds, and 72° C. for 30 seconds; a final extension at 72° C. for 30 seconds; and a hold at 10° C. The resulting PCR product of 200 bp was purified by 1% agarose gel electrophoresis using TAE buffer, excised from the gel, and further purified using a MINELUTE® Gel Extraction Kit.

Plasmid pEvFz36 was digested with Not I and purified by 1% agarose gel electrophoresis using TAE buffer, excised from the gel, and further purified using a QIAQUICK® Gel Extraction Kit.

Figure 4:
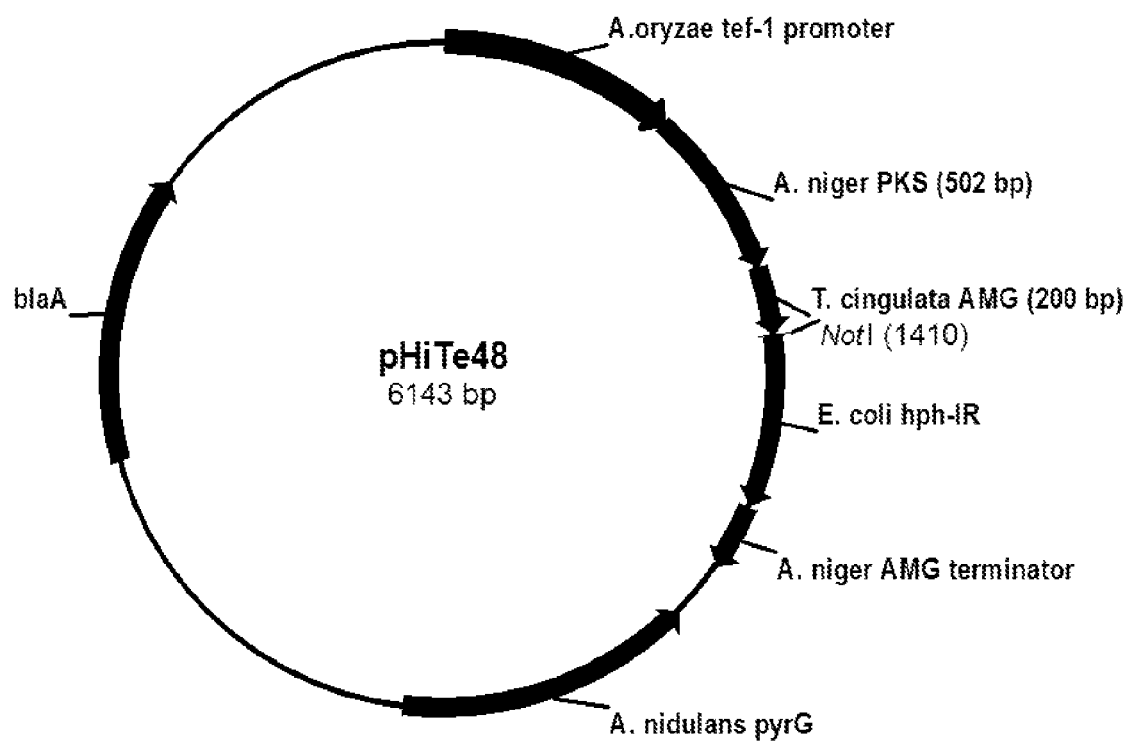
FIG. 4 shows a restriction map of pHiTe48.

The 200 bp PCR product was ligated to the Not I digested pEvFz36 plasmid using an IN-FUSION™ Advantage PCR Cloning Kit and the ligation mixture was transformed into SURE® chemically competent *Escherichia coli* cells according to the manufacturer's instructions. Transformants were selected on 2XYT agar plates containing 100 μg of ampicillin per ml. Plasmid DNA from several transformants were purified using a BIOROBOT® 9600 and analyzed by DNA sequencing using a 3130xl Genetic Analyzer to identify plasmids containing the desired amyloglucosidase insert. One plasmid with the expected DNA sequence was designated pHiTe48 (FIG. 4).

Example 5

Protoplast Preparation and Transformation of *Aspergillus niger*

Protoplast preparation and transformation were performed according to the protocol of Penttila et al., 1987, Gene 61: 155-164. Briefly, conidia were cultivated in 100 ml of YP medium, supplemented with 2% (w/v) glucose and 10 mM uridine, at 30° C. with agitation at 110 rpm for 18 hours. Young germlings were collected by filtration using a Vacuum Driven Disposable Filtration System (Millipore, Bedford, Mass., USA) and washed twice with 20 mM CaCl$_2$-0.7 M KCl. Protoplasts were generated by suspending the washed germlings in 10 ml of 20 mM CaCl$_2$-0.7 M KCl containing 20 mg of GLUCANEX® 200 G (Novozymes Switzerland AG, Neumatt, Switzerland) per ml for 50-60 minutes at 37° C. with mixing at 100 rpm. The protoplasting mix was filtered through sterile MIRACLOTH® (Calbiochem, San Diego, Calif., USA), and the MIRACLOTH® was washed with 20 mM $CaCl_2$-0.7 M KCl to release any protoplasts trapped in the MIRACLOTH®. Protoplasts were collected by centrifuging at 537×g for 10 minutes and resuspending the pellet in 20 ml of STC solution. Washing of the protoplasts was repeated a second time. The protoplasts were counted using a hemocytometer and re-suspended to a final concentration of 1×10$^7$ protoplasts per ml of STC solution. Excess protoplasts were stored in a Cryo 1° C. Freezing Container (Nalgene, Rochester, N.Y., USA) at −80° C.

For selection of the *Aspergillus nidulans* orotidine-5'-phosphate decarboxylase (pyrG) marker, approximately 5 μg of plasmid DNA were added to 100 μl of the protoplast solution and mixed gently. One milliliter of SPTC solution was added, mixed, and incubated at room temperature for 30 minutes. After incubation, 45 ml of COVE-N-JP top agarose were then added to the DNA transformation mix and plated onto three COVE-N-JP transformation agar plates. The plates were incubated at 30° C. for 7-10 days. Transformants were sub-cultured onto COVE-N-gly agar plates and grown at 30° C. for 7-10 days.

Example 6

Cultivation of Transformants

Conidia from selected transformants of Example 5 were inoculated into sterile 14 ml FALCON™ culture tubes (BD Biosciences, San Jose, Calif., USA) containing 4 ml of MU-1/MLC medium (1000 ml of MU-1 medium combined with 200 ml of MLC medium and 40 ml of 50% urea), and incubated at 30° C. and 200 rpm for 7 days. Supernatants from the cultures were collected by centrifugation at 1643×g for 15 minutes and assayed for amyloglucosidase (AMG) activity, as described in Example 7.

For shake flasks, 2-5×10$^7$ conidia from selected transformants were inoculated into 125 ml shake flasks containing 25 ml of MU-1/MLC medium, and incubated at 30° C. and 200 rpm for 7 days. Four milliliters supernatant samples from each culture were collected by centrifugation at 1643×g for 15 minutes and assayed for amyloglucosidase (AMG) activity, as described in Example 7.

Example 7

Amyloglucosidase (AMG) Assay

Culture supernatants were assayed for amyloglucosidase (AMG) activity according to the following method using a BIOMEK® 3000 and BIOMEK® NX (Beckman Coulter, Inc., Fullerton Calif., USA). The culture supernatants were diluted from 0-fold to ⅓-fold to ⅕-fold in 0.1 M sodium acetate-0.01% TRITON® X-100 pH 5.0 (sample buffer). An AMG® enzyme standard (Novozymes NS, Bagsvaerd, Denmark) was diluted using 2-fold steps starting with an 8 AGU/ml concentration and ending with a 1 AGU/ml concentration in the sample buffer. A 20 μl aliquot of each dilution was transferred to a 96-well flat bottom plate. One hundred microliters of p-nitrophenyl-alpha-D-glycopyranoside substrate solution (1 mg/ml in 0.1 M sodium acetate pH 5.0) were added to each well, and the plate was incubated at ambient temperature for 45 minutes. Upon completion of the incubation the reaction was quenched with 100 μl of 0.06 N NaOH. The endpoint of the reaction was measured at 405 nm. Enzyme concentrations were determined by extrapolation from the standard curve.

Example 8

SDS-PAGE Analysis of the Culture Supernatants

Ten microliters of supernatant from each transformant were mixed with 10 μl of Laemmli Sample Buffer (Bio-Rad Laboratories, Inc., Hercules, Calif., USA) supplemented with 0.5% (v/v) 3-mercaptoethanol. After heating at 95° C. for 5 minutes, 20 μl of each sample and 15 μl of PRECISION PLUS PROTEIN™ unstained molecular weight standards (Bio-Rad Laboratories, Inc., Hercules, Calif., USA) were loaded onto a CRITERION STAIN FREE™ gel (Bio-Rad Laboratories, Inc., Hercules, Calif., USA) and electrophoresed at 150 V for 1.5 hours in Tris/Glycine/SDS buffer (Bio-Rad Laboratories, Inc., Hercules, Calif., USA). The protein bands were visualized using a CRITERION STAIN FREE™ Imaging System (Bio-Rad Laboratories, Inc., Hercules, Calif., USA).

Example 9

A Morphology-Based Transitive RNAi Screen Promotes Co-Silencing of the Inserted *Trametes cingulata* Amyloglucosidase (AMG) Target Plasmid pHiTe48 contains a 200 bp fragment derived from the *Trametes cingulata* amyloglucosidase (AMG) gene inserted downstream of a 502 bp fragment *Aspergillus niger* polyketide synthase gene and upstream of the 505 bp *Escherichia coli* hph-IR. Four micrograms of pHiTe48 were used to transform protoplasts of *Aspergillus niger* strain M1137, prepared as described in Example 5, and selected on COVE-N-JP transformation agar plates at 30° C. for 7-10 days. Fifty white-spored transformants, 48-w1 through 48-w50, and 10 black-spored transformants, 48-b1 through 48-b10, were purified twice by re-streaking on COVE-N-gly agar plates at 30° C. for 7-10 days. Conidia from purified transformants were collected and used to inoculate duplicate FALCON™ culture tubes containing 4 ml of MU-1/MLC medium and incubated at 30° C. and 200 rpm for 7 days (Example 6). After 7 days of cultivation, duplicate samples from each culture were centrifuged at 1643×g for 15 minutes to produce supernatants for amyloglucosidase activity assays (Example 7) and SDS-PAGE analysis (Example 8).

Figure 5A:
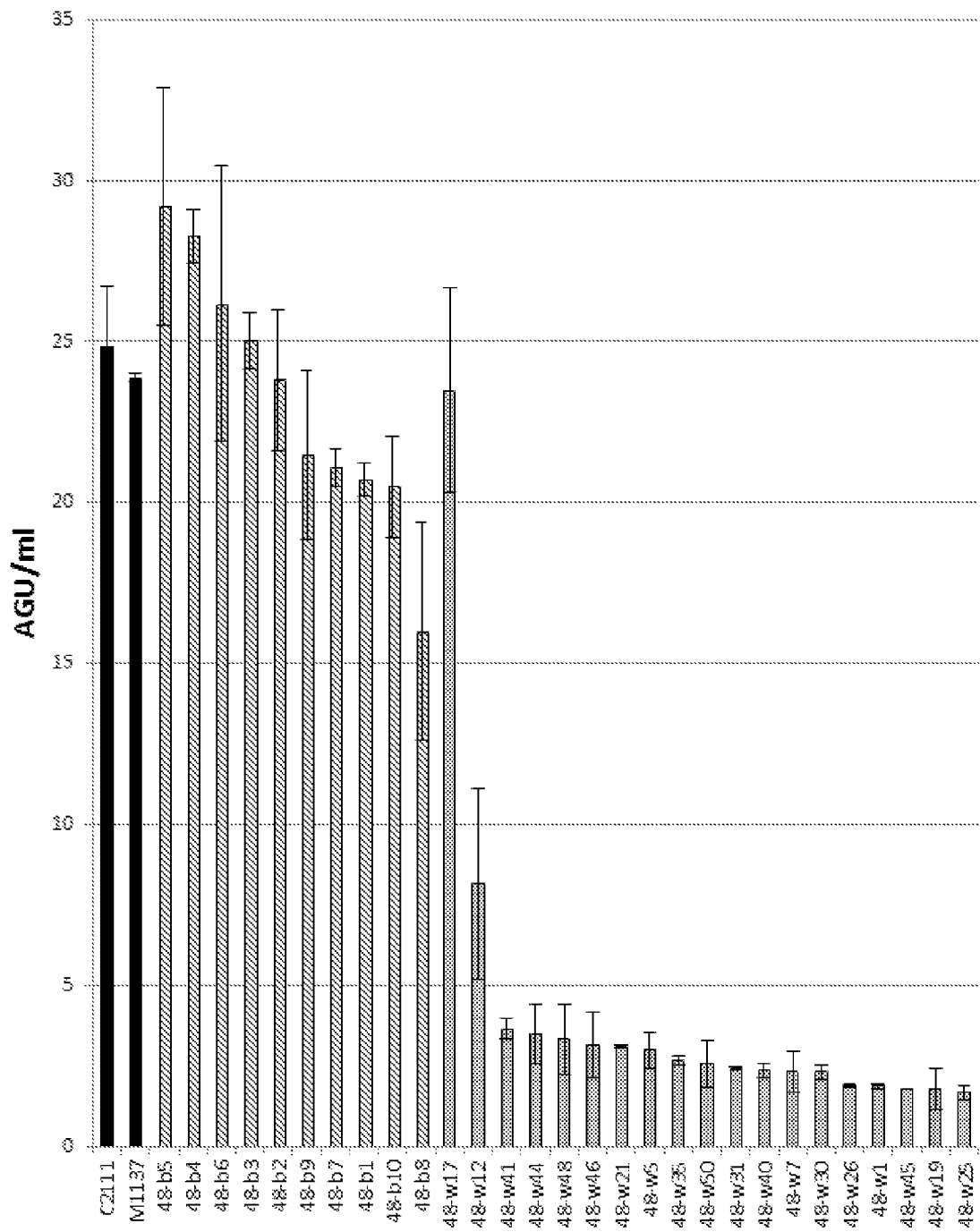
FIGS. 5A and 5B show amyloglucosidase activities of white-spored *Aspergillus niger* transformants relative to the wild-type control strains *Aspergillus niger* C2111 and *Aspergillus niger* M1137.
Figure 5B:
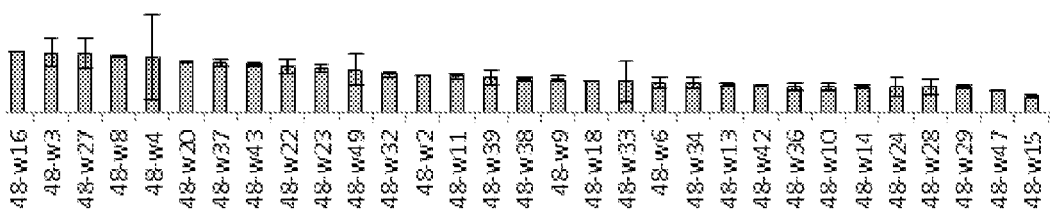
Figure 6:
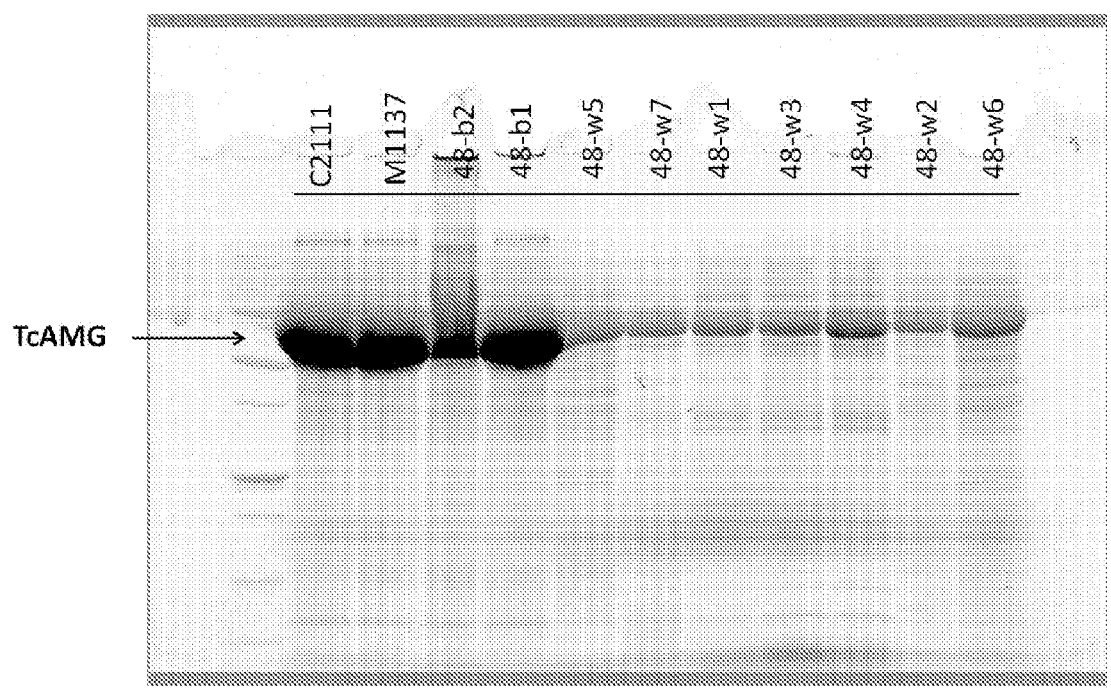
FIG. 6 shows SDS-PAGE analysis of *Aspergillus niger* transformants having reduced amyloglucosidase activities.

Amyloglucosidase activities of all 10 black-spored transformants, 48-b1 through 48-b10, were consistent with the wild-type control strains *Aspergillus niger* C2111 and *Aspergillus niger* M1137 (a pyrG− isolate derived from *Aspergillus niger* C2111). In contrast, amyloglucosidase activities of white-spored transformants were considerably less than the host strain *Aspergillus niger* M1137 and its parent *Aspergillus niger* C2111. Amyloglucosidase activity assays revealed that 49 of 50 white-spored transformants yielded considerably lower amyloglucosidase activities with an average reduction of 93% when compared to the wild-type control strains *Aspergillus niger* C2111 and *Aspergillus niger* M1137 (FIGS. 5A and 5B). Amyloglucosidase activities of the control strain, untransformed *Aspergillus niger* C2111, and the 10 black-spored transformants, 48-b1 through 48-b10, did not differ significantly according to Welch's t-test, $t(10.62)=1.18$, $p>0.2$, whereas amyloglucosidase activities of *Aspergillus niger* C2111 compared to the 50 white-spored transformants, 48-w1 through 48-w50, did differ significantly with t-test results of $t(123.44)=47.80$, $p<0.001$. The results demonstrated a direct correspondence between spore color and amyloglucosidase activity Supernatant samples from selected transformants having reduced amyloglucosidase (AMG) activities were also analyzed by SDS-PAGE as described in Example 8. The results are shown in FIG. 6. Decreases in the yields of secreted amyloglucosidase proteins paralleled lower amyloglucosidase activity as seen in the enzyme assay results.

Figure 7A:
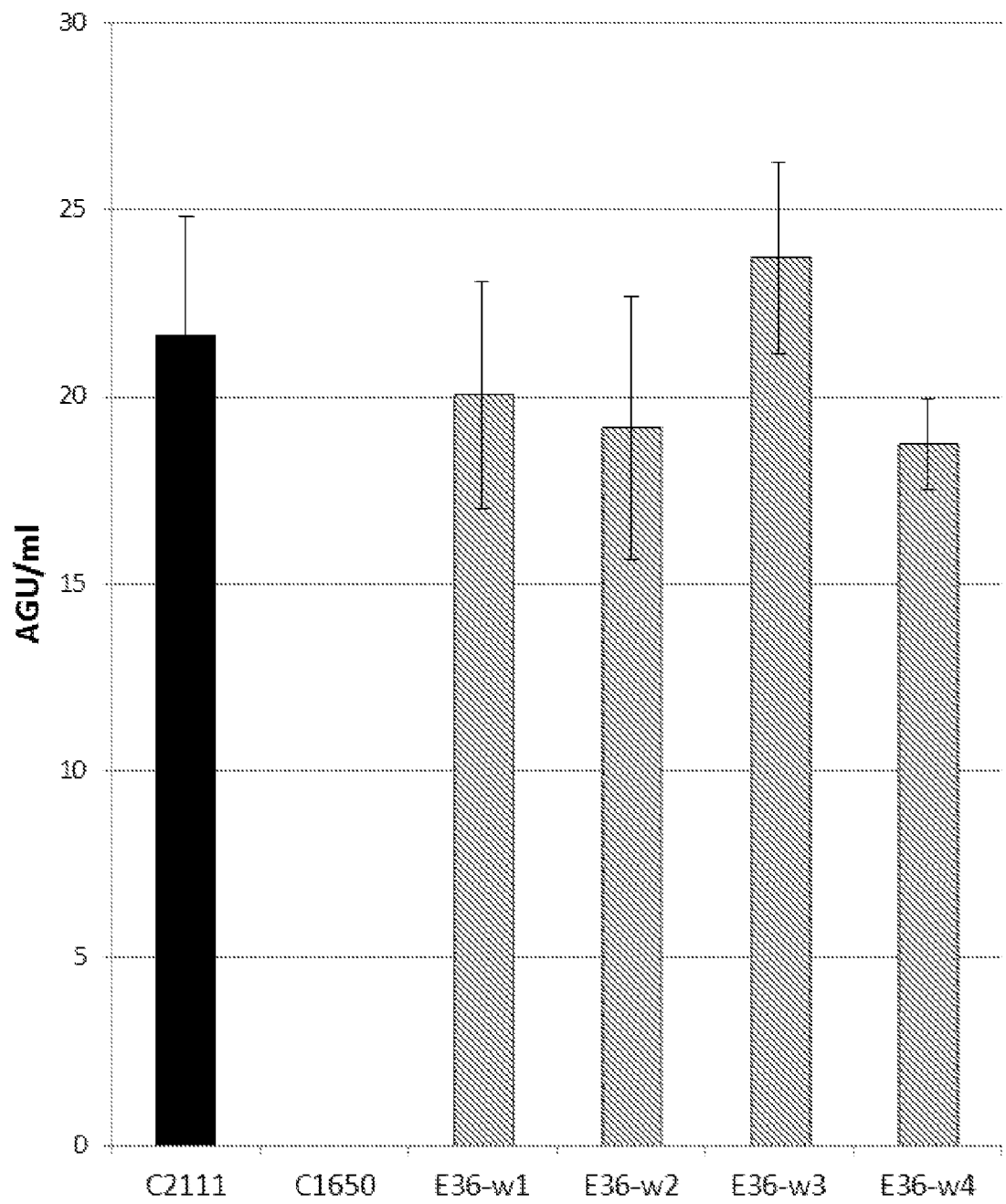
FIGS. 7A and 7B show amyloglucosidase activity of 10 white-spored *Aspergillus niger*, resulting from the introduction of control plasmid pEvFz36 into *Aspergillus niger* M1137 and relative to *Aspergillus niger* strain C2111.
Figure 7B:
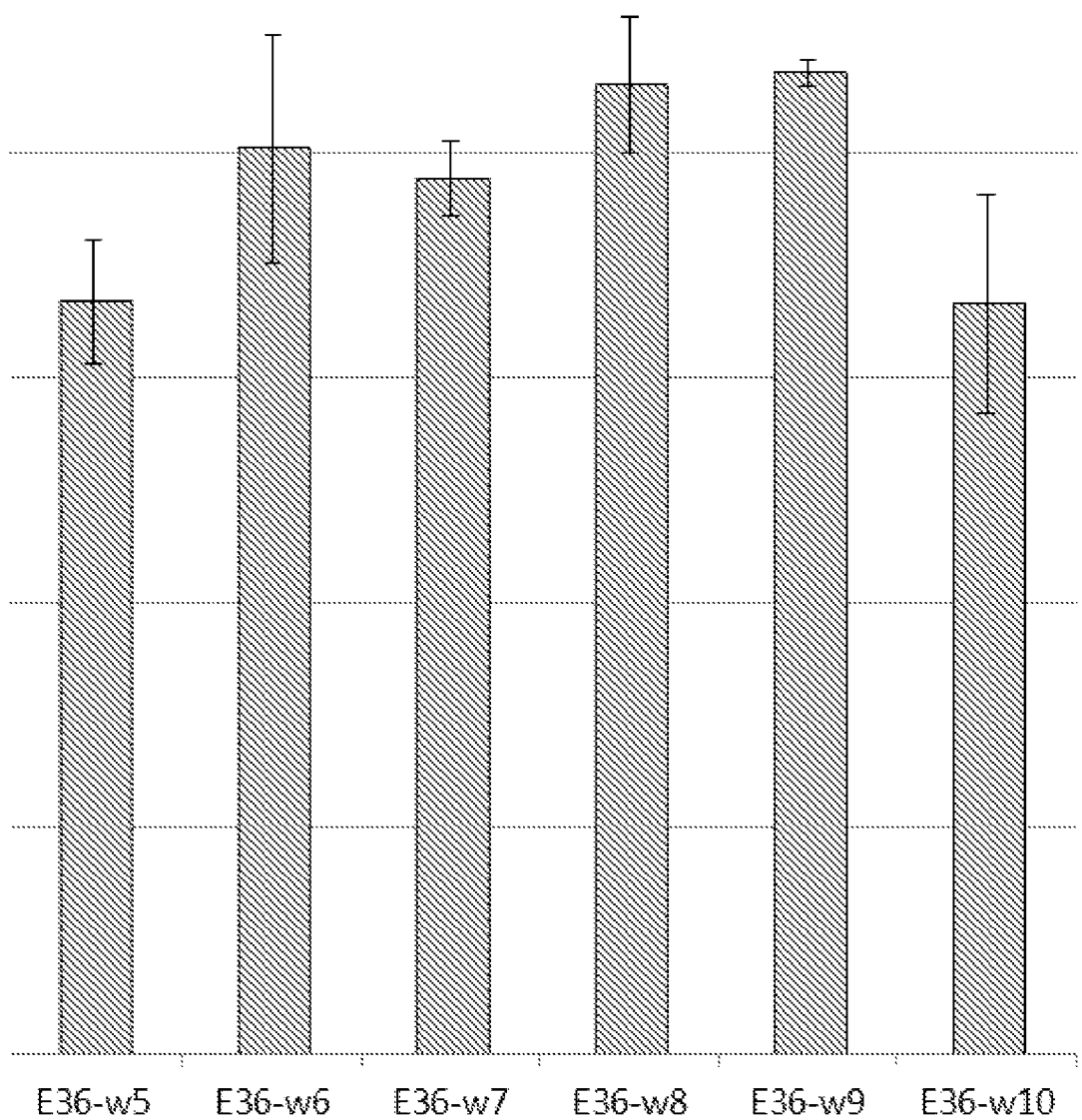
Figure 8A:
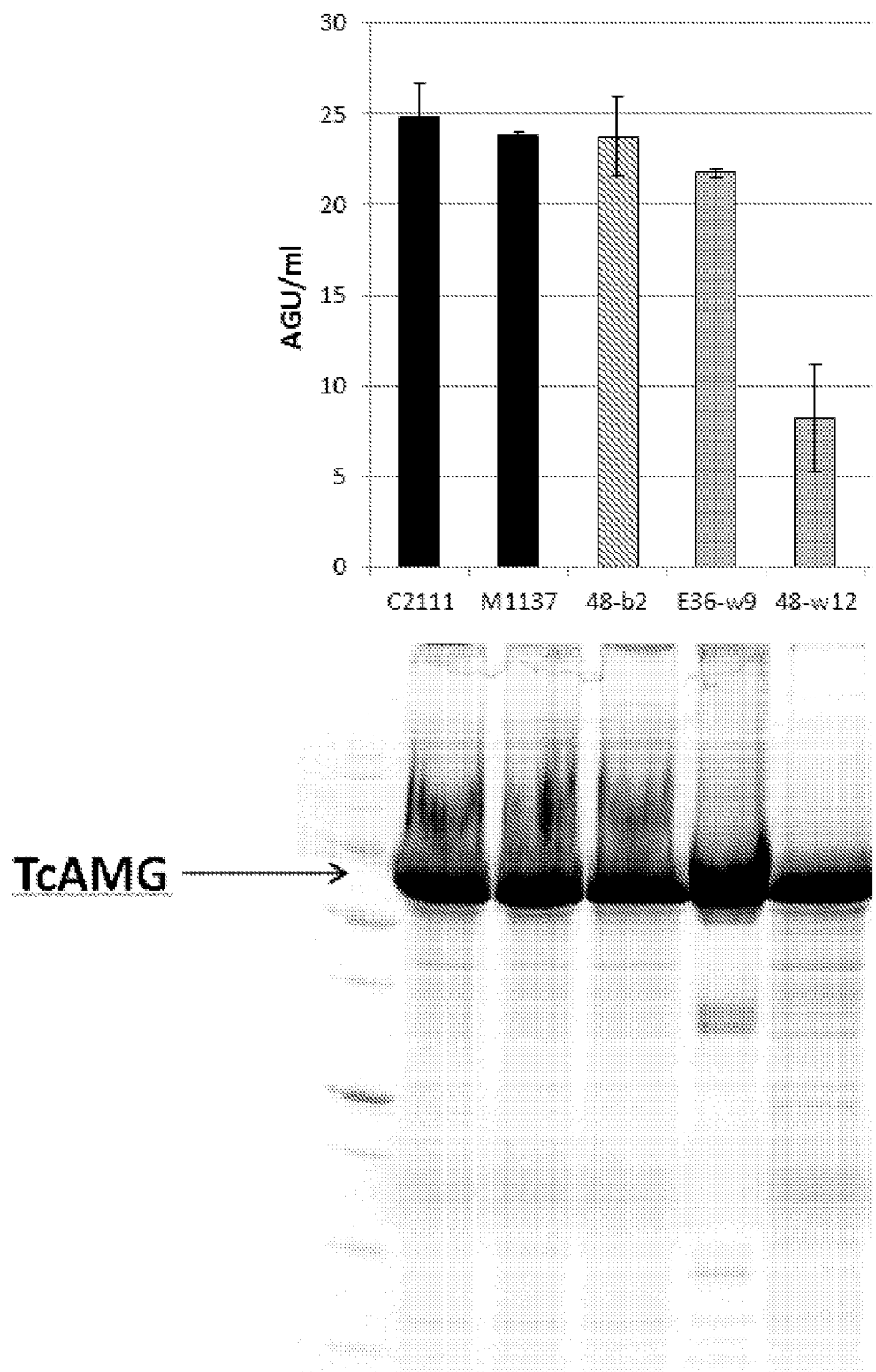
FIGS. 8A and 8B show amyloglucosidase activity and SDS-PAGE analysis of *Aspergillus niger* transformants 48-b2 and E36-w9 in comparison to selected white-spored transformants and control strains *Aspergillus niger* C2111, *Aspergillus niger* M1137 and *Aspergillus niger* C1650.
Figure 8B:
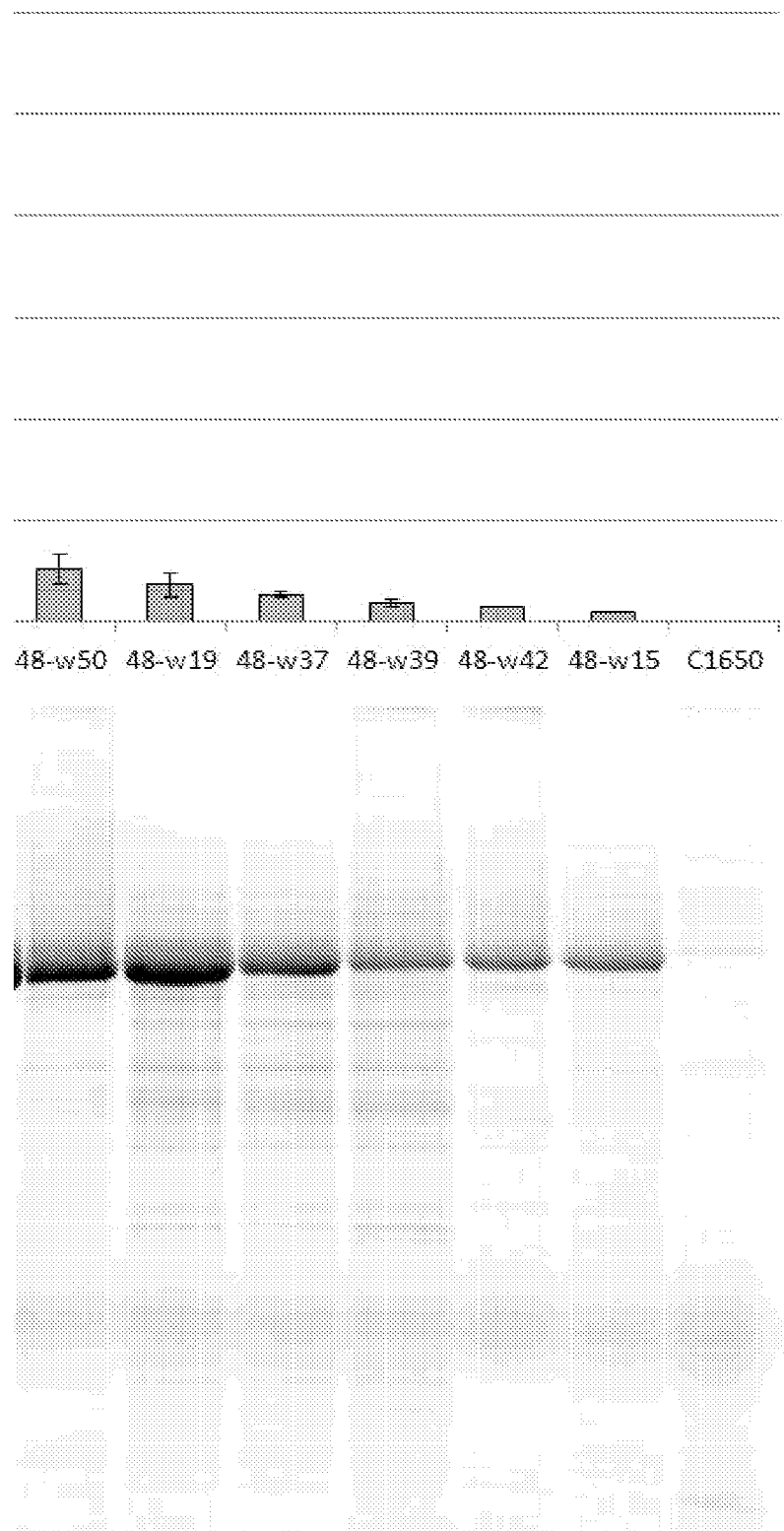

To confirm that spore color did not influence enzyme activity, *Aspergillus niger* strain M1137 transformed with pEvFz36 (*Aspergillus niger* polyketide synthase transitive RNAi vector) yielded both black and white transformants from which 10 white-spored transformants, E36-w1 through E36-w10, were isolated and purified twice on COVE-N-gly agar plates. Tube cultures of the selected transformants were prepared as described in Example 6. When assayed for amyloglucosidase (AMG) activity according to Example 7, all 10 white-spored transformants demonstrated comparable activities with *Aspergillus niger* strain M1137 as shown in FIGS. 7A and 7B. Analysis of transformant E36-w9 via SDS-PAGE, as described in Example 8, displayed amylogucosidase (AMG) protein yields similar to *Aspergillus niger* M1137 as shown in FIGS. 8A and 8B. These results demonstrated that placement of a target sequence inserted downstream of a sequence actively undergoing gene silencing can be efficiently co-suppressed.

Example 10

Construction of Plasmid pEvFz49

A transitive RNAi vector was constructed for the purpose of suppressing the expression of an *Aspergillus oryzae* RIB40 conidial yellow pigment biosynthesis polyketide synthase wA gene (SEQ ID NO: 11 for the cDNA sequence and SEQ ID NO: 12 for the deduced amino acid sequence; Accession No. XP_001822700.1).

Plasmid pEvFz49 was constructed to contain the *Aspergillus oryzae* tef-1 promoter (Example 1), a PCR amplified fragment of the open reading frame for the *Aspergillus oryzae* wA gene, the *Escherichia coli* hygromycin phosphotransferase inverted repeat (hph-IR), the *Aspergillus niger* amyloglucosidase (AMG) terminator, and the full-length *Aspergillus nidulans* pyrG gene as a selectable marker. The *Aspergillus oryzae* wA gene was chosen as a target for silencing because of its sequence identity to other polyketide synthases involved in conidial pigment biosynthesis in fungi.

Figure 9:
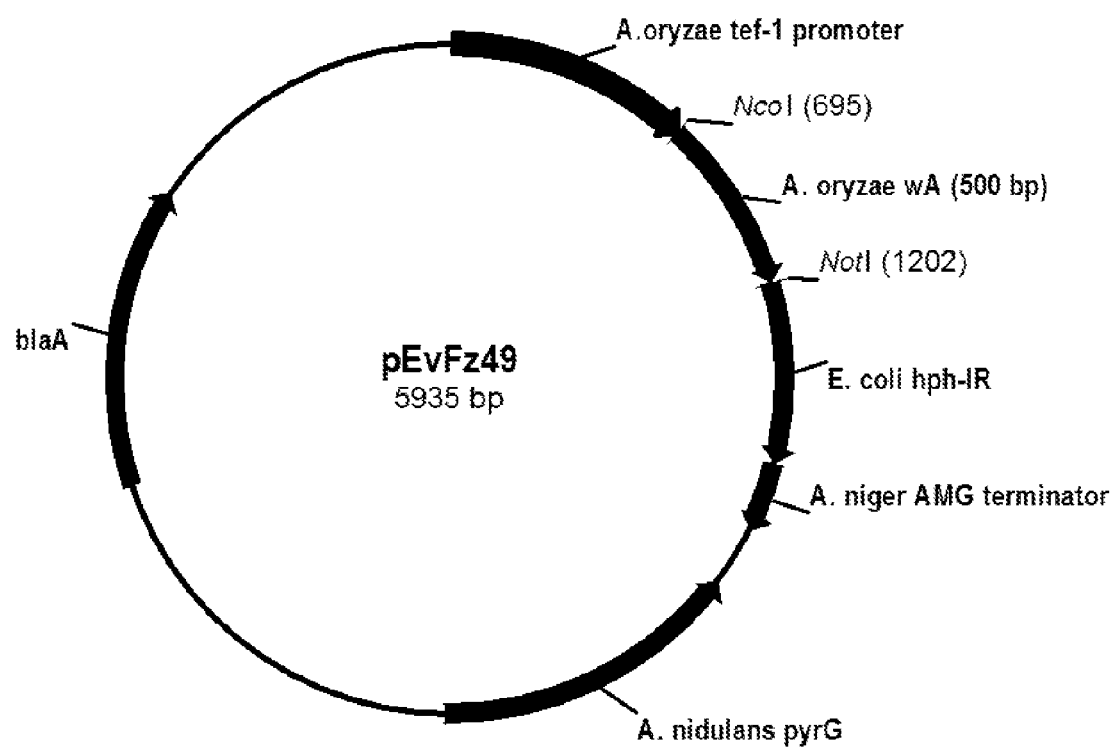
FIG. 9 shows a restriction map of pEvFz49.

A 500 bp fragment from pDM266 (WO 2008/080017) was digested with Nco I and Not I, ligated to Nco I/Not I digested pEvFz35 (Example 2) using a QUICK LIGATION™ Kit, and transformed into SURE® chemically competent *Escherichia coli* cells according to the manufacturer's instructions. Transformants were selected on 2XYT agar plates containing 100 µg of ampicillin per ml. Plasmid DNA samples from several transformants were purified using a BIOROBOT® 9600 and analyzed by DNA sequencing using a 3130xl Genetic Analyzer to identify plasmids containing the desired wA insert. One plasmid with the expected DNA sequence was designated pEvFz49 (FIG. 9).

Example 11

Construction of Transitive RNAi Vectors for Co-Suppression of Both the *Aspergillus oryzae* wA and *Polyporus pinsitus* Laccase Genes Transitive RNAi vectors were constructed for co-suppressing the expression of an *Aspergillus oryzae* RIB40 conidial yellow pigment biosynthesis polyketide synthase wA gene, described in Example 10, and *Polyporus pinsitus* (*Trametes villosa*) laccase gene (SEQ ID NO: 13 for the cDNA sequence and SEQ ID NO: 14 for the deduced amino acid sequence) using varying lengths of the laccase target to determine if silencing efficiency is affected.

All plasmids described in this Example were constructed to contain the *Aspergillus oryzae* tef-1 promoter upstream of a 500 bp fragment of the open reading frame for the *Aspergillus oryzae* wA gene, various fragment lengths within the open reading frame of the *Polyporus pinsitus* laccase gene, the 507 bp *Escherichia coli* hygromycin phosphotransferase inverted repeat (hph-IR) from *Escherichia coli*, *Aspergillus niger* amyloglucosidase (AMG) terminator, and *Aspergillus nidulans* pyrG gene as a selectable marker.

Construction of Plasmid pEvFz51.

Genomic DNA of *Aspergillus oryzae* DSY10 was prepared using a DNEASY® Plant Maxi Kit (QIAGEN Inc., Valencia, Calif., USA) according to the manufacturer's instructions. A 200 bp fragment from the 5' end of the open reading frame of the *Polyporus pinsitus* laccase gene was PCR amplified from *Aspergillus oryzae* DSY10 genomic DNA using the primers shown below where the 5' ends of both primers were engineered to contain 20 bp of homologous sequence of the ends of the linearized vector pEvFz49, described in Example 10.

(sense):
(SEQ ID NO: 15)
5'-CCTGCGTTCGTTCTGCGGCC<u>ATGATGTCGAGGTTTCACTCTC</u>-3'

(antisense):
(SEQ ID NO: 16)
5'-TCCCCGAACATCGCGCGGCC<u>TGGAAGCGATCCCCCATGTTACCGG</u>-3'

The laccase coding sequence is denoted by underlined letters.

The amplification reaction was composed of 1× HERCULASE® Reaction Buffer (Agilent Technologies, La Jolla, Calif., USA), 0.2 mM dNTPs, 200 ng of *A. oryzae* DSY10 genomic DNA, 50 pmoles of sense primer 0612662, 50 pmoles of antisense primer 0612663, and 2.5 units of HERCULASE® Hotstart DNA polymerase (Agilent Technologies, La Jolla, Calif., USA) in a final volume of 50 µl. The reaction was incubated in an EPPENDORF® MASTERCYCLER® 5333 programmed for 1 cycle at 92° C. for 2 minutes; 30 cycles each at 92° C. for 30 seconds, 63° C. for 30 seconds, and 72° C. for 30 seconds; a final extension at 72° C. for 10 minutes; and a hold at 10° C. The resulting PCR product of 240 bp was purified by 0.8% agarose gel electrophoresis using TAE buffer, excised from the gel, and further purified using a MINELUTE® Gel Extraction Kit.

Figure 10:
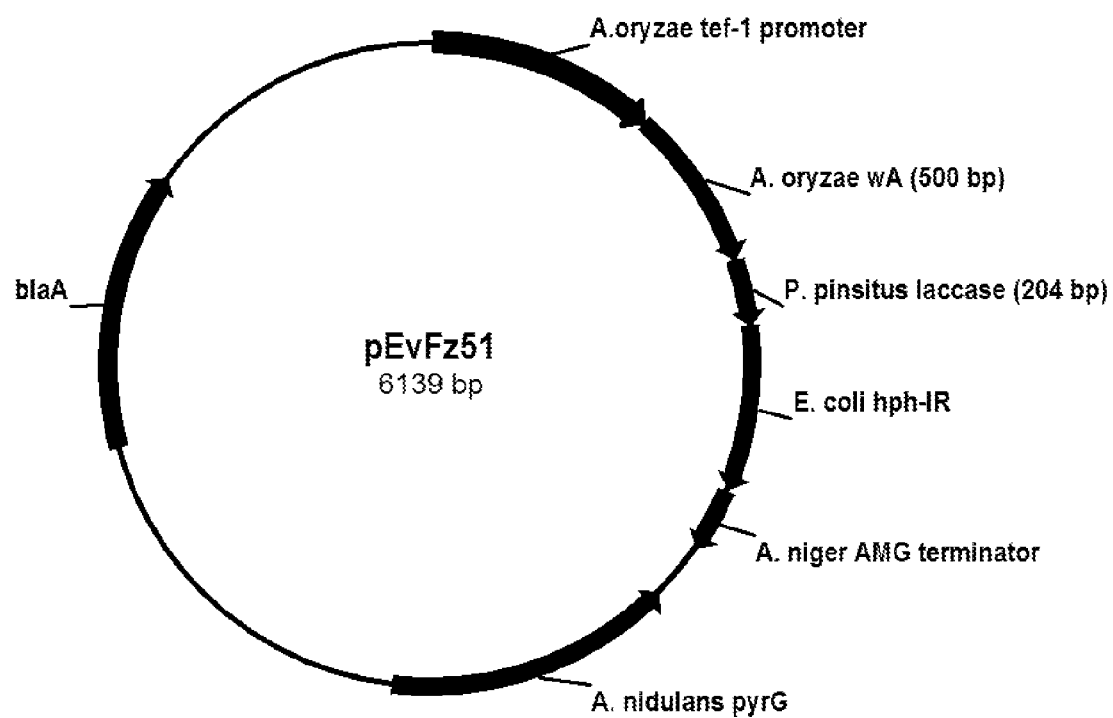
FIG. 10 shows a restriction map of pEvFz51.

Plasmid pEvFz49 was digested with Not I and purified using a QIAQUICK® PCR Purification Kit (QIAGEN Inc., Valencia, Calif., USA) according to the manufacturer's protocol. The 240 bp PCR product was ligated to the Not I digested pEvFz49 using an IN-FUSION™ Advantage PCR Cloning Kit and the ligation mixture was transformed into SURE® chemically competent *Escherichia coli* cells according to the manufacturer's instructions. Transformants were selected on 2XYT agar plates containing 100 µg of ampicillin per ml. Plasmid DNA from several transformants were purified using a BIOROBOT® 9600 and analyzed by DNA sequencing using a 3130xl Genetic Analyzer to identify plasmids containing the desired *Polyporus pinsitus* laccase insert. One plasmid with the expected DNA sequence was designated pEvFz51 (FIG. 10).

Construction of Plasmid pEvFz54.

A 500 bp fragment from the middle region of the open reading frame of the *Polyporus pinsitus* laccase gene was PCR amplified from *Aspergillus oryzae* DSY10 genomic DNA using the primers shown below where the 5' ends of both primers were engineered to contain 20 bp of homologous sequence of the ends of the linearized vector pEvFz49, described in Example 10.

```
Primer 0612666 (sense):
                                        (SEQ ID NO: 17)
5'-CCTGCGTTCGTTCTGCGGCCCGCATTCCCTCTCGGCGCCGACGCC
ACCCTCATCA-3'

Primer 0612667 (antisense):
                                        (SEQ ID NO: 18)
5'-TCCCCGAACATCGCGCGGCCTGATGGCCAGGTCGACACCAC-3'
```

The laccase coding sequence is denoted by underlined letters.

The amplification reaction was composed of 1× HERCULASE® Reaction Buffer, 0.2 mM dNTPs, 200 ng of *A. oryzae* DSY10 genomic DNA, 50 pmoles of sense primer 0612666, 50 pmoles of antisense primer 0612667, and 2.5 units of HERCULASE® Hotstart DNA polymerase in a final volume of 50 µl. The reaction was incubated in an EPPENDORF® MASTERCYCLER® 5333 programmed for 1 cycle at 92° C. for 2 minutes; 30 cycles each at 92° C. for 30 seconds, 65° C. for 30 seconds, and 72° C. for 30 seconds; a final extension at 72° C. for 10 minutes; and a hold at 10° C. The resulting PCR product of 540 bp was purified by 0.8% agarose gel electrophoresis using TAE buffer, excised from the gel, and further purified using a MINELUTE® Gel Extraction Kit.

Plasmid pEvFz49 was digested with Not I and purified using a QIAQUICK® PCR Purification Kit according to the manufacturer's protocol.

Figure 11:
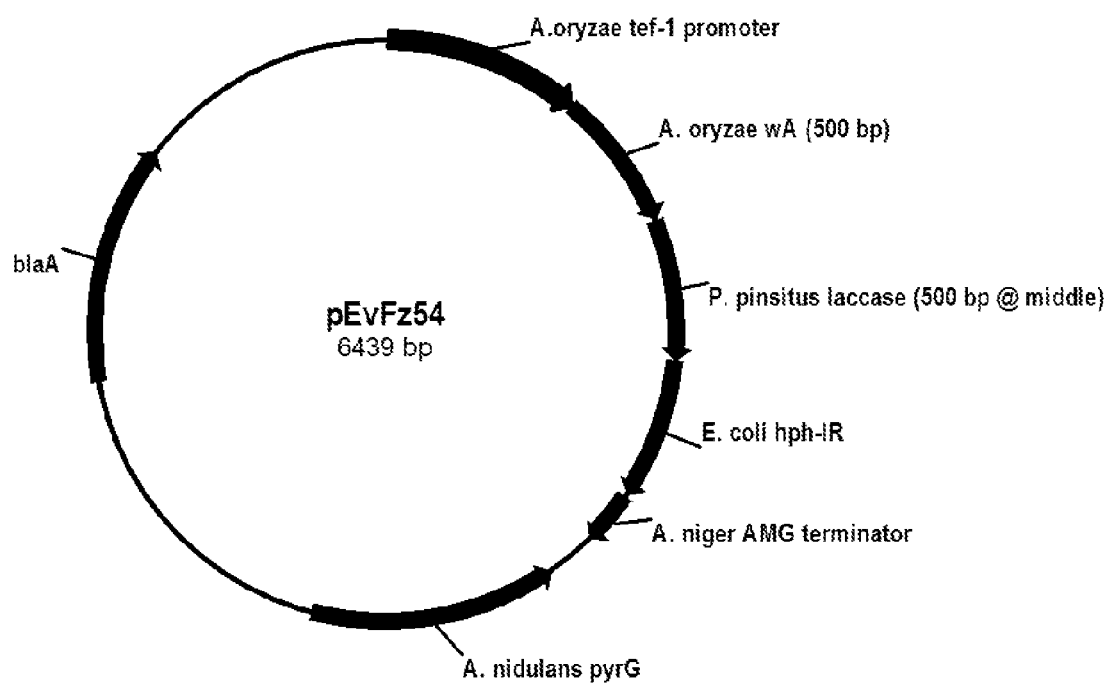
FIG. 11 shows a restriction map of pEvFz54.

The 540 bp PCR product was ligated to the Not I digested pEvFz49 using an IN-FUSION™ Advantage PCR Cloning Kit and the ligation mixture was transformed into SURE® chemically competent *Escherichia coli* cells according to the manufacturer's instructions. Transformants were selected on 2XYT agar plates containing 100 µg of ampicillin per ml. Plasmid DNA from several transformants were purified using a BIOROBOT® 9600 and analyzed by DNA sequencing using a 3130xl Genetic Analyzer to identify plasmids containing the desired *Polyporus pinsitus* laccase insert. One plasmid with the expected DNA sequence was designated pEvFz54 (FIG. 11).

Construction of Plasmid pEvFz55.

A 500 bp fragment from the 3' end of the open reading frame of the *Polyporus pinsitus* laccase gene was PCR amplified from *Aspergillus oryzae* DSY10 genomic DNA using the primers shown below where the 5' ends of both primers were engineered to contain 20 bp of homologous sequence of the ends of the linearized vector pEvFz49, described in Example 10.

```
Primer 0612668 (sense):
                                        (SEQ ID NO: 19)
5'-CCTGCGTTCGTTCTGCGGCCGCACCAACTTCTTCATCAACGGCGCGT
CTTTCAC-3'

Primer 0612669 (antisense):
                                        (SEQ ID NO: 20)
5'-TCCCCGAACATCGCGCGGCCTTACTGGTCGCTCGGGTCGA-3'
```

The laccase coding sequence is denoted by underlined letters.

The amplification reaction was composed of 1× HERCULASE® Reaction Buffer, 0.2 mM dNTPs, 200 ng of *A. oryzae* DSY10 genomic DNA, 50 pmoles of sense primer 0612668, 50 pmoles of antisense primer 0612669, and 2.5 units of HERCULASE® Hotstart DNA polymerase in a final volume of 50 µl. The reaction was incubated in an EPPENDORF® MASTERCYCLER® 5333 programmed for 1 cycle at 92° C. for 2 minutes; 30 cycles each at 92° C. for 30 seconds, 67° C. for 30 seconds, and 72° C. for 30 seconds; a final extension at 72° C. for 10 minutes; and a hold at 10° C. The resulting PCR product of 540 bp was purified by 0.8% agarose gel electrophoresis using TAE buffer, excised from the gel, and further purified using a MINELUTE® Gel Extraction Kit.

Plasmid pEvFz49 was digested with Not I and purified using a QIAQUICK® PCR Purification Kit according to the manufacturer's protocol.

Figure 12:
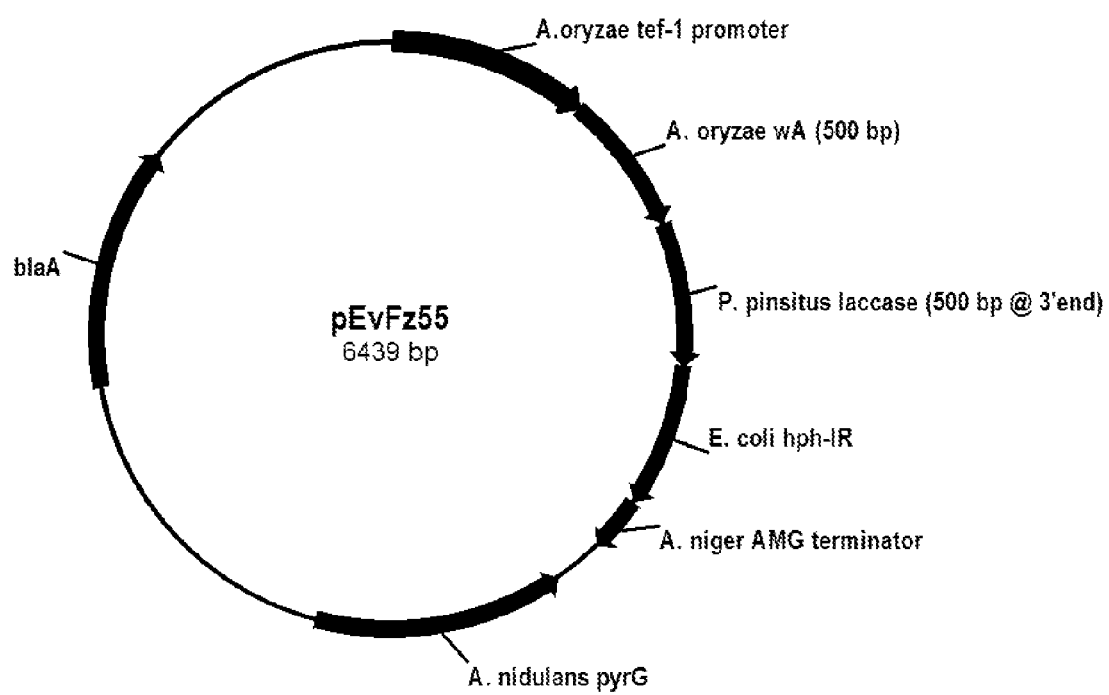
FIG. 12 shows a restriction map of pEvFz55.

The 540 bp PCR product was ligated to the Not I digested pEvFz49 using an IN-FUSION™ Advantage PCR Cloning Kit and the ligation mixture was transformed into SURE® chemically competent *Escherichia coli* cells according to the manufacturer's instructions. Transformants were selected on 2XYT agar plates containing 100 µg of ampicillin per ml. Plasmid DNA from several transformants were purified using a BIOROBOT® 9600 and analyzed by DNA sequencing using a 3130xl Genetic Analyzer to identify plasmids containing the desired *Polyporus pinsitus* laccase insert. One plasmid with the expected DNA sequence was designated pEvFz55 (FIG. 12).

Example 12

Protoplast Preparation and Transformation of *Aspergillus oryzae*

*Aspergillus oryzae* strain DSY10ΔpyrG was grown on a PDA plate supplemented with 10 mM uridine for 7 days at 34° C. Protoplast preparation and transformation were performed according to the protocol of Penttila et al., 1987, Gene 61: 155-164. Briefly, conidia were cultivated in 100 ml of YP medium, supplemented with 2% (w/v) glucose and 10 mM uridine, at 28° C. with agitation at 110 rpm for 16-18 hours. Young germlings were collected by filtration using a sterile funnel lined with sterile MIRACLOTH® and washed twice with 0.7 M KCl, supplemented with 20 mM $CaCl_2$. Protoplasts were generated by suspending the washed germlings in 10 ml of 0.7 M KCl, supplemented with 20 mM $CaCl_2$, containing 20 mg of GLUCANEX® 200 G per ml and 0.2 mg of chitinase (Sigma-Aldrich, St. Louis, Mo., USA) per ml for 30-90 minutes at 37° C. with mixing at 80 rpm. The protoplasting mix was filtered through a sterile funnel lined with sterile MIRACLOTH®, and the MIRACLOTH® was washed with 0.7 M KCl, supplemented with 20 mM $CaCl_2$, to release any protoplasts trapped in the MIRACLOTH®. Protoplasts were collected by centrifuging at 1,303×g for 10 minutes and resuspending the pellet in 20 ml of STC solution. Washing of the protoplasts was repeated a second time. The protoplasts were counted using a hemocytometer and re-suspended to a final concentration of $2 \times 10^7$ protoplasts per ml of STC solution. Excess protoplasts were stored in a Cryo 1° C. Freezing Container at −80° C.

Approximately 3 µg of plasmid DNA was added to 100 µl of the protoplast solution and mixed gently. Three hundred microliters of 60% PEG-4000 solution were added, mixed, and incubated at room temperature for 30 minutes. After incubation, 45 ml of pyrG selection top agar were then added to the DNA transformation mix and plated onto three Minimal medium transformation plates. The plates were incubated at 34° C. for 5-7 days. Primary transformants were visually inspected using a Nikon SMZ1500 stereoscopic microscope (Nikon, Melville, N.Y., USA) for loss of spore coloration. Transformants were spore purified three times on Minimal medium agar plates and grown at 34° C. for 5-7 days.

Example 13

Cultivation of Transformants

Spore suspensions from selected transformants of Example 12 were collected in 0.01% TWEEN® 20 solution. Duplicate shake flasks containing 25 ml of MY25 medium, supplemented with 1 mM $Cu_2SO_4$, were inoculated with 0.2 ml spore suspension from each transformant, and incubated at 34° C. and 200 rpm for 5 days. Culture supernatants were harvested by centrifugation at 1643×g for 10 minutes and assayed for laccase activity, as described in Example 14.

Example 14

Laccase Assay

Culture supernatants were assayed for laccase activity according to the following method using a BIOMEK® 3000 and BIOMEK® NX. The culture supernatants were diluted ⅒ in 0.1 M sodium acetate, 0.01% TRITON® X-100 pH 5.0 (sample buffer) followed by a series dilution from 0-fold to ⅓-fold to ⅑-fold of the diluted sample. A purified laccase standard from *Myceliophthora thermophila* (Novozymes NS, Bagsvaerd, Denmark) was diluted using 2-fold steps starting with a 0.0865 LACCU/ml concentration and ending with a 0.01 LACCU/ml concentration in the sample buffer. A total of 20 μl of each dilution including standard was transferred to a 96-well flat bottom plate. Two hundred microliters of an ABTS (2,2'-azino-bis(3-ethylbenzthiazoline-6-sulfonic acid)) substrate solution (0.1 M sodium acetate pH 5.0+0.275 mg/ml ABTS+0.01% TRITON® X-100) were added to each well and then incubated at ambient temperature for 30 minutes. During the incubation the rate of the reaction was measured at an optical density of 405 nm for the 96-well plate. Sample concentrations were determined by extrapolation from the generated standard curve.

Example 15

Insertional Transcription RNAi Reveals Substantial Co-Suppression of Both Spore Color and Laccase Activity in *Aspergillus oryzae*

Plasmids pEvFz51, pEvFz54, and pEvFz55 derived from pEvFz49 are similar in that all *Polyporus pinsitus* laccase gene derived fragments were inserted at the Not I restriction site of pEvFz49 directly downstream of the 500 bp *Aspergillus oryzae* wA fragment and directly upstream of the 507 bp hph inverted repeat. Plasmid pEvFz51 contains a 200 bp fragment derived from the 5' end of the *Polyporus pinsitus* laccase gene, pEvFz54 contains a 500 bp fragment derived from the central region, and pEvFz55 contains a 500 bp fragment derived from the 3' end of the *Polyporus pinsitus* laccase gene.

Three micrograms of DNA from each plasmid were used to transform protoplasts of *Aspergillus oryzae* strain DSY10ΔpyrG, prepared as described in Example 12, and selected on Minimal medium transformation plates at 34° C. for 5-7 days. Ten transformants displaying a loss of spore coloration and two green-spored transformants, representative of the wild-type phenotype, per plasmid transformed were spore purified twice on Minimal medium agar plates at 34° C. for 5-7 days. Conidia from purified transformants were collected and used to inoculate duplicate shake flasks containing 25 ml of MY25 medium, supplemented with 1 mM $Cu_2SO_4$, and incubated at 34° C. and 200 rpm for 7 days (Example 13). *Aspergillus oryzae* strains DSY10 and HowB104 were included as positive and negative controls for laccase activity, respectively. After 5 days of cultivation, culture samples were harvested by centrifugation at 1643×g for 10 minutes to produce supernatants for laccase activity assay (Example 14).

Figure 13A:
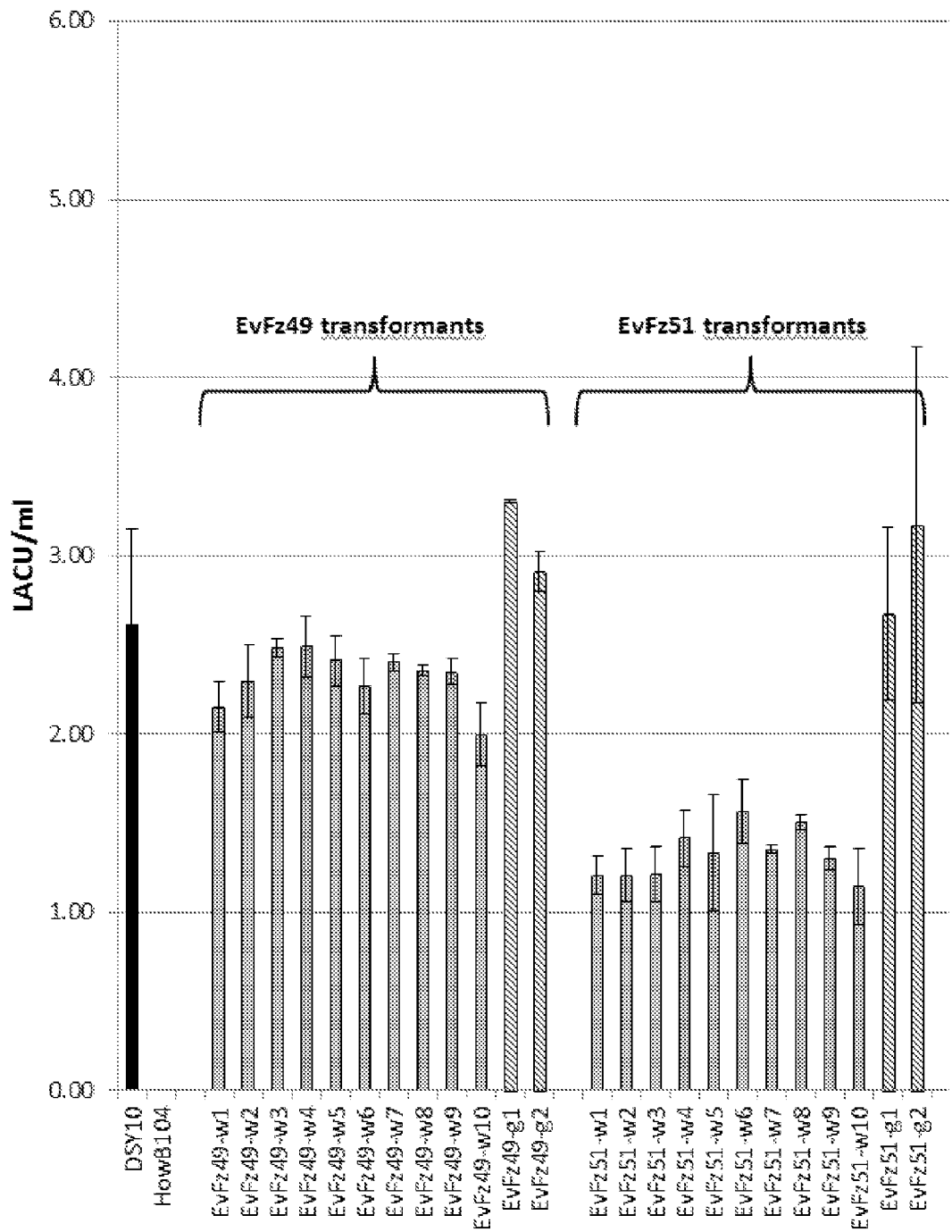
FIGS. 13A and 13B show laccase activity of 10 white-spored *Aspergillus oryzae* transformants resulting from each plasmid and relative to control strain *Aspergillus oryzae* DSY10.
Figure 13B:
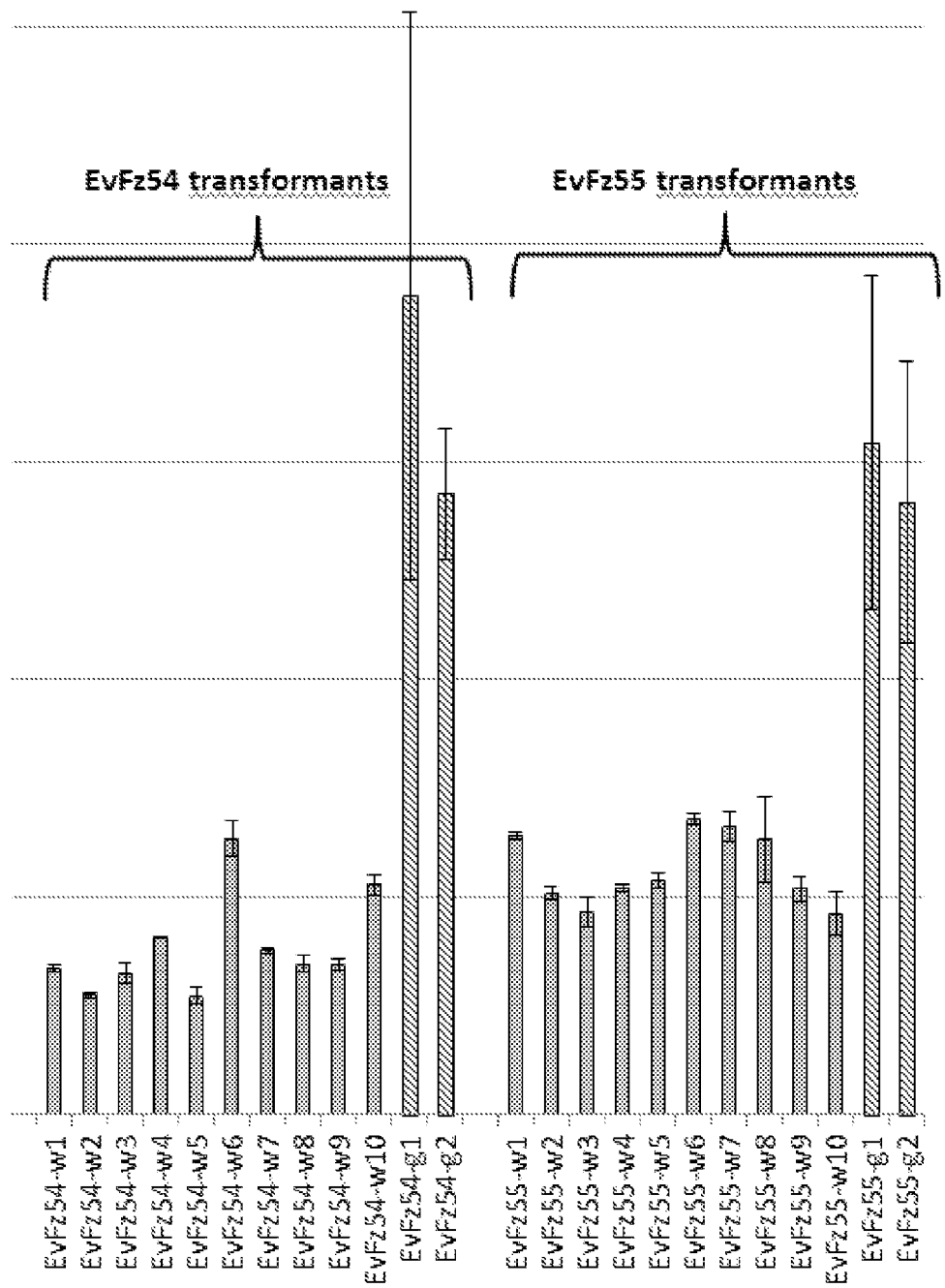

The laccase assay results showed that all white-spored transformants isolated from transformation with pEvFz51 (EvFz51-w1 through EvFz51-w10) had at least a two-fold decrease in enzyme activity in comparison with the control strain *A. oryzae* DSY10. Similar results were demonstrated with transformants EvFz54-w1 through EvFz54-w10 and EvFz55-w1 through EvFz55-w10 (FIGS. 13A and 13B). The laccase activities of all white-spored transformants evaluated were considerably less than the control strain *A. oryzae* DSY10 with an average reduction of 50% when compared to the wild-type control. Six transformants (EvFz51-g1, EvFz51-g2, EvFz54-g1, EvFz54-g2, EvFz55-g1, and EvFz55-g2) with green (wild-type) spore color were also obtained and exhibited comparable enzyme levels to that of *A. oryzae* DSY10, indicating that transformation alone with the three insertional transitive RNAi constructs did not impact either spore coloration or laccase productivity. Moreover, the reduced expression of both genes were closely associated.

To confirm that spore color did not influence enzyme activity, *Aspergillus oryzae* strain DSY10ΔpyrG was transformed with control plasmid pEvFz49, containing only the 500 bp fragment *Aspergillus oryzae* polyketide synthase gene upstream of the 507 bp hph-IR, which yielded transformants with spore color ranging from green (wild-type) to white, and from which two green-spored transformants, EvFz49-g1 and EvFz49-g2, and 10 white-spored transformants, EvFz49-w1 through EvFz49-w10, were isolated and purified twice on Minimal medium agar plates. Shake flasks of the selected transformants were prepared as described in Example 13. When assayed for laccase activity according to Example 14, all 10 white-spored transformants demonstrated comparable activities to *Aspergillus oryzae* strain DSY10 (FIGS. 13A and 13B), as expected, due to the absence of the *Polyporus pinsitus* laccase target. The results demonstrated that variation in spore coloration did not have an impact on laccase activity.

These results also revealed that a target sequence of 200 bp or 500 bp is effective for silencing the gene of interest, and the length of the target is not crucial to inducing gene silencing events within a population. This experiment clearly demonstrated the successful co-suppression of two targets in *Aspergillus oryzae*.

Example 16

Construction of Plasmid pHiTe43

The yeast fcy1 gene encoding cytosine deaminase was previously identified in *Saccharomyces cerevisiae* by gene mutation counter-selective growth on solid media containing the cytosine analogue, 5-fluorocytosine (5-FC) (Hartzog et al., 2005, Yeast 22: 789-798). In the presence of a functional fcy1 marker, 5-FC is converted to the toxic compound 5-fluorouracil (5-FU) (Hartzog et al., 2005, supra).

For construction of pHiTe43, an *Aspergillus niger* fcy1 (SEQ ID NO: 21 for the cDNA sequence and SEQ ID NO: 22 for the deduced amino acid sequence; EMBL:am269962) gene fragment was obtained by PCR using genomic DNA from *Aspergillus niger* strain M1137 as a template. Genomic DNA of *Aspergillus niger* strain M1137 was prepared using a DNEASY® Plant Mini Kit (QIAGEN Inc., Valencia, Calif., USA). A 266 bp fragment of the fcy1 gene with Nco I and Not I sites introduced at the ends was obtained by PCR using the following primers:

```
Primer HTCA-28 (sense):
                                      (SEQ ID NO: 23)
5'-CATGGCCATGGGCTGAGATGTCCGCGCT-3'

Primer HTCA-29 (antisense):
                                      (SEQ ID NO: 24)
5'-ATAAGAATGCGGCCGCCAAAGCTCCGGCTTCTCCT-3'.
```

The amplification reaction was composed of 1× GENEAMP® PCR Buffer II, 0.2 mM dNTPs, 100 ng of *Aspergillus niger* M1137 genomic DNA, 50 pmoles of sense primer HTCA-28, 50 pmoles of antisense primer HTCA-29, and 5 units of AMPLITAQ GOLD® DNA polymerase in a final volume of 50 µl. The reaction was incubated in an EPPENDORF® MASTERCYCLER® 5333 programmed for 1 cycle at 95° C. for 9 minutes; 30 cycles each at 95° C. for 30 seconds, 55° C. for 30 seconds, and 72° C. for 30 seconds; a final extension at 72° C. for 30 seconds; and a hold at 10° C. The resulting PCR product of 266 bp was purified by 0.8% agarose gel electrophoresis using TAE buffer, excised from the gel, and further purified using a MINELUTE® Gel Extraction Kit.

Plasmid pEvFz36 (Example 3) was digested with Nco I and Not I and purified using a QIAQUICK® PCR Purification Kit according to the manufacturer's protocol.

Figure 14:
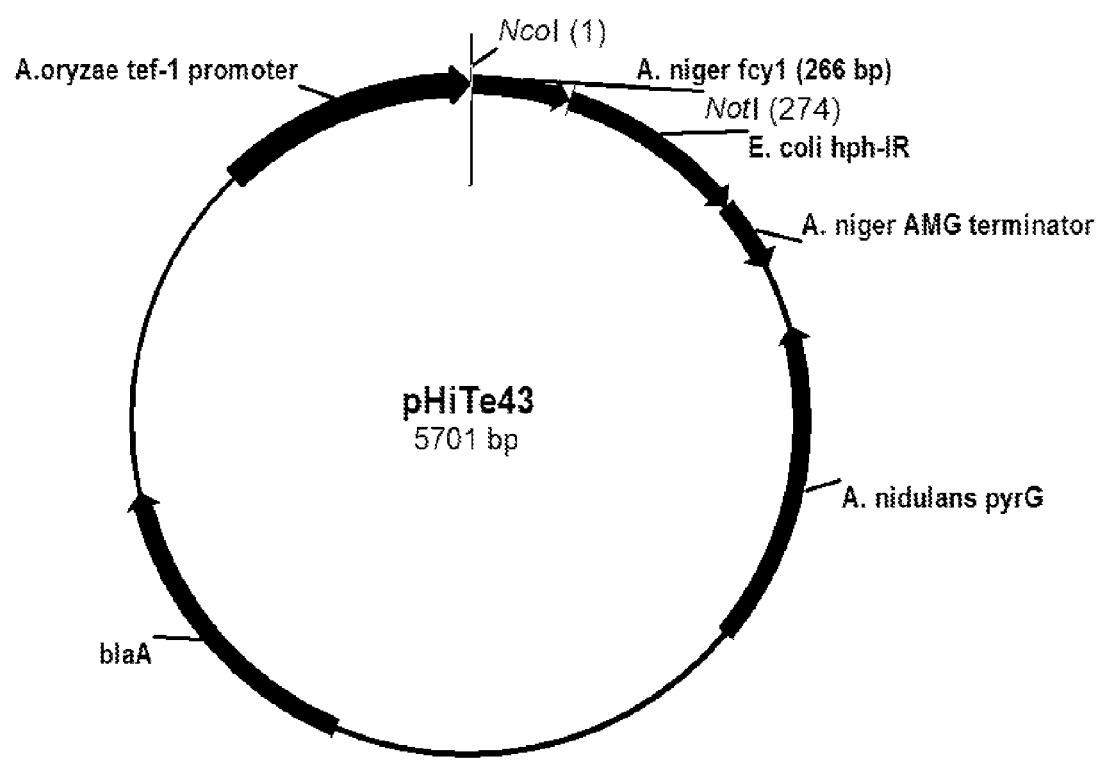
FIG. 14 shows a restriction map of pHiTe43.

The 266 bp PCR product was ligated to the Nco I/Not I digested pEvFz36 plasmid using a QUICK LIGATION™ Kit and the ligation mixture was transformed into SURE® chemically competent *Escherichia coli* cells according to the manufacturer's instructions. Transformants were selected on 2XYT agar plates containing 100 µg of ampicillin per ml. Plasmid DNA from several transformants were purified using a BIOROBOT® 9600 and analyzed by DNA sequencing using a 3130 4 Genetic Analyzer to identify plasmids containing the desired *Aspergillus niger* fcy1 insert. One plasmid bearing the correct sequence was designated pHiTe43 (FIG. 14).

Example 17

Construction of Plasmid pHiTe49

A 200 bp fragment of the *Trametes cingulata* amyloglucosidase (AMG) open reading frame was amplified from pHiTe08 (SEQ ID NO: 8) using the primers shown below where the 5' ends of both primers were engineered to contain 15-17 bp of homologous sequence of the ends of the linearized vector pHiTe43, described in Example 16.

```
Primer HTCA-40 (sense):
                                      (SEQ ID NO: 25)
5'-GGAGCTTTGGCGGCCATGCGTTTCACGCTCCTCAC-3'

Primer HTCA-41 (antisense):
                                      (SEQ ID NO: 26)
5'-GAACATCGCGCGGCCGCTTCGGGTGGATGTGCTCG-3'
```

The amplification reaction was composed of 1× GENEAMP® PCR Buffer II, 0.2 mM dNTPs, 20 ng of pHiTe08 plasmid DNA, 50 pmoles of sense primer HTCA-40, 50 pmoles of antisense primer HTCA-41, and 5 units of AMPLITAQ GOLD® DNA polymerase in a final volume of 50 µl. The reaction was incubated in an EPPENDORF® MASTERCYCLER® 5333 programmed for 1 cycle at 95° C. for 9 minutes; 30 cycles each at 95° C. for 30 seconds, 55° C. for 30 seconds, and 72° C. for 30 seconds; a final extension at 72° C. for 30 seconds; and a hold at 10° C. The resulting PCR product of 200 bp was purified by 0.8% agarose gel electrophoresis using TAE buffer, excised from the gel, and further purified using a MINELUTE® Gel Extraction Kit.

Plasmid pHiTe43 was digested with Not I and then dephosphorylated with Antarctic phosphatase (New England Biolabs, Inc., Ipswich, Mass., USA). The dephosphorylation reaction was composed of 1× Antarctic Phosphatase Reaction Buffer and 5 units of Antarctic phosphatase added to the previous Not I digestion. The reaction was incubated at 37° C. for 15 minutes followed by heat inactivation at 70° C. for 5 minutes. The dephosphorylation reaction was used directly in the ligation.

Figure 15:
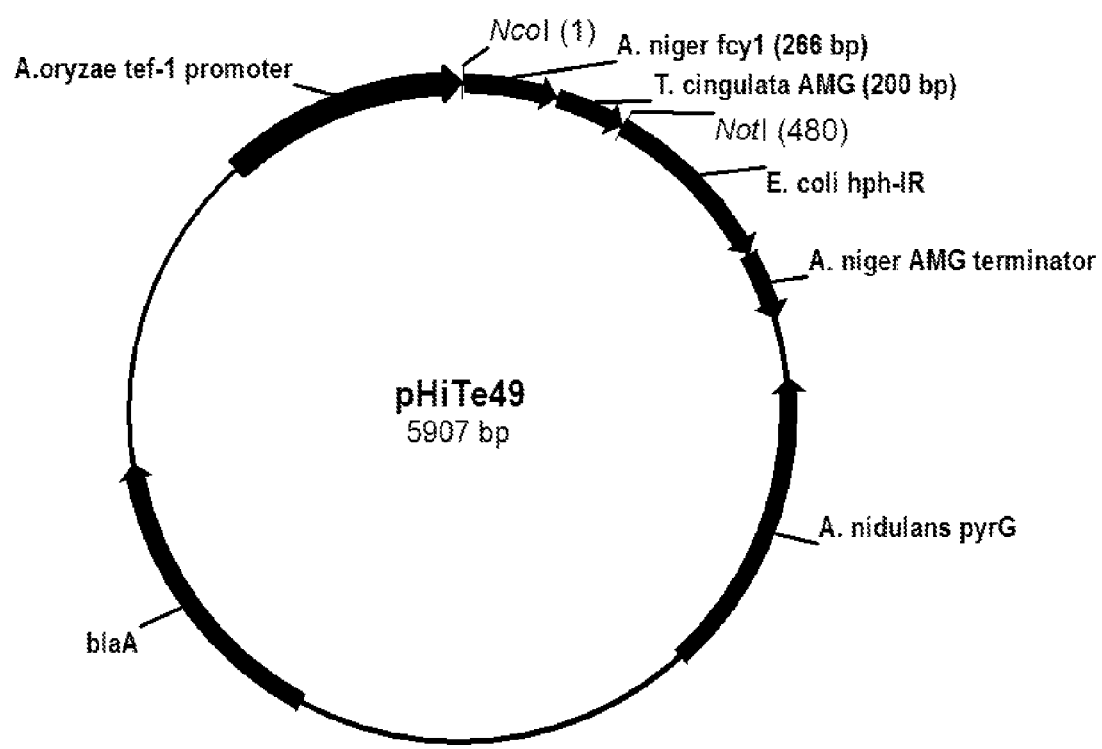
FIG. 15 shows a restriction map of pHiTe49.

The 200 bp PCR product was ligated to the Not I digested pHiTe43 using an IN-FUSION™ Advantage PCR Cloning Kit and the ligation mixture was transformed into SURE® chemically competent *Escherichia coli* cells according to the manufacturer's instructions. Transformants were selected on 2XYT agar plates containing 100 µg of ampicillin per ml. Plasmid DNA from several transformants were purified using a BIOROBOT® 9600 and analyzed by DNA sequencing using a 3130xl Genetic Analyzer to identify plasmids containing the desired *Polyporus pinsitus* laccase insert. One plasmid bearing the correct DNA sequence was designated pHiTe49 (FIG. 15).

Example 18

Counter Selection of Fcy1 Using Insertional Transitive Silencing Reveals Efficient Co-Suppression of the *Trametes cingulata* AMG Target in *Aspergillus niger*

Figure 16A:
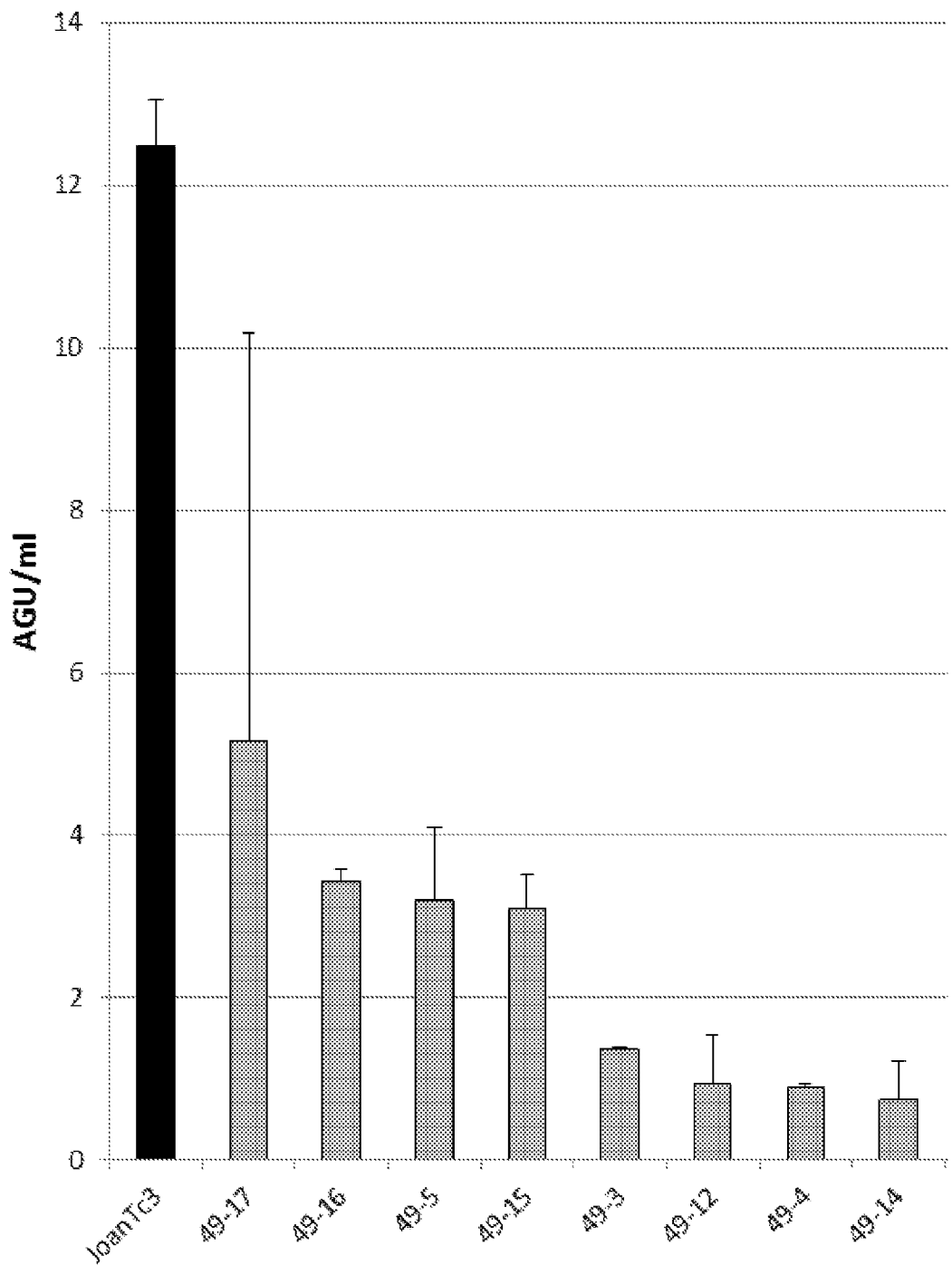
FIGS. 16A and 16B show amyloglucosidase assay results of 18 fcy1-resistant transformants in comparison to control strain *Aspergillus niger* strain JoanTc3.
Figure 16B:

Plasmid pHiTe49 was used to transform protoplasts prepared from *Aspergillus niger* strain EvFz5 as described in Example 5. Transformed protoplasts were spread onto COVE-N-JP transformation agar plates lacking uridine and 5-fluorocytosine (Sigma-Aldrich, St. Louis, Mo., USA). Orotidine-5'-phosphate carboxylase (pyrG) prototrophs were allowed to regenerate for 4 days at 30° C. at which time 15 ml of COVE-N-JP top agarose containing 1 µg/ml 5-fluorocytosine (5-FC) was overlaid on the transformation plates with additional incubation for 6-10 days at 30° C. A total of 18 transformants regenerated on 1 µg/ml 5-FC were subcultured twice on COVE-N-gly agar plates containing 1 µg/ml 5-FC. For tube culture analysis, conidia from the transformants able to grow on 5-FC were inoculated into 14 ml FALCON™ culture tubes containing 4 ml of MU-1/MLC medium and incubated at 30° C. and 200 rpm for 7 days (Example 6). Four milliliters of broth from each culture were collected by centrifugation at 1643×g for 15 minutes. Collected broth was assayed for amyloglucosidase (AMG) activity, as described in Example 7. Activity in all 18 transformants expressed amyloglucosidase at a median enzyme activity of 1.4 AGU compared to 13 AGU expressed in the untransformed host strain *Aspergillus niger* JoanTc3. Overall, the 18 transformants displayed an average decrease of enzyme of 89.5% (FIGS. 16A and 16B). These experiments confirmed (1) potency of RNA interference was sufficient to simulate genetic auxotrophs of fcy1 and (2) simultaneous co-suppression of both *Aspergillus niger* fcy1 and *Trametes cingulata* AMG indicated an equivalence of gene silencing upstream of the RNAi inducer.

The present invention is further described by the following numbered paragraphs:

[1] A method for co-silencing expression of genes encoding biological substances in a filamentous fungal strain, comprising: (a) inserting into the genome of the filamentous fungal strain a double-stranded transcribable nucleic acid construct comprising a promoter operably linked to a first polynucleotide comprising a first transcribable region with homology to a first target gene encoding a first biological substance, a second polynucleotide comprising a second transcribable region with homology to a second target gene encoding a second biological substance, and a third polynucleotide comprising a third transcribable region with no effective homology to the first and second target genes; wherein the third transcribable region comprises two segments complementary to each other in reverse orientation; and wherein the first, second, and third transcribable regions are transcribed as a single-stranded RNA molecule; and (b) producing short interfering RNAs (siRNAs) by cultivating the filamentous fungal strain under conditions to produce RNA transcripts of the double-stranded transcribable nucleic acid construct that are then converted to the siRNAs, which interact with RNA transcripts of the target genes to silence expression of the target genes encoding the first and second biological substances.

[2] The method of paragraph 1, wherein the first transcribable region with homology to the first target gene comprises at least 19 nucleotides of the first target gene.

[3] The method of paragraph 1 or 2, wherein the second transcribable region with homology to the second target gene comprises at least 19 nucleotides of the second target gene.

[4] The method of any of paragraphs 1-3, wherein the third transcribable region with no effective homology to the first and second target genes comprises at least 19 nucleotides.

[5] The method of paragraph 4, wherein the third transcribable region has no effective homology to the genome of the filamentous fungal strain.

[6] The method of paragraph 4, wherein the third transcribable region has homology to a third target gene.

[7] The method of any of paragraphs 1-6, wherein expression of the first target gene is reduced by at least 20%, at least 30%, at least 40%, at least 50%, at least 60%, at least 70%, at least 80%, at least 90%, or 100%.

[8] The method of any of paragraphs 1-7, wherein expression of the second target gene is reduced by at least 20%, at least 30%, at least 40%, at least 50%, at least 60%, at least 70%, at least 80%, at least 90%, or 100%.

[9] The method of paragraph 6-8, wherein expression of the third target gene is reduced by at least 20%, at least 30%, at least 40%, at least 50%, at least 60%, at least 70%, at least 80%, at least 90%, or 100%.

[10] The method of any of paragraphs 1-9, wherein the short interfering RNAs interact with RNA transcripts of one or more homologues of the target genes to silence expression of the one or more homologues of the target genes.

[11] The method of paragraph 10, wherein expression of the one or more homologues of the target genes are reduced by at least 20%, at least 30%, at least 40%, at least 50%, at least 60%, at least 70%, at least 80%, at least 90%, or 100%.

[12] The method of any of paragraphs 1-11, wherein the double-stranded transcribable nucleic acid construct further comprises at least one additional polynucleotide comprising an additional transcribable region with homology to an additional target gene encoding an additional biological substance.

[13] The method of paragraph 12, wherein the additional transcribable region with homology to the additional target gene comprises at least 19 nucleotides of the additional target gene.

[14] The method of paragraph 12 or 13, wherein expression of the additional target gene is reduced by at least 20%, at least 30%, at least 40%, at least 50%, at least 60%, at least 70%, at least 80%, at least 90%, or 100%.

[15] The method of any of paragraphs 12-14, wherein the short interfering RNAs interact with RNA transcripts of one or more homologues of the additional target gene to silence expression of the one or more homologues of the additional target gene.

[16] The method of paragraph 15, wherein expression of the one or more homologues of the additional target gene is reduced by at least 20%, at least 30%, at least 40%, at least 50%, at least 60%, at least 70%, at least 80%, at least 90%, or 100%.

[17] A filamentous fungal strain comprising a double-stranded transcribable nucleic acid construct comprising a promoter operably linked to a first polynucleotide comprising a first transcribable region with homology to a first target gene encoding a first biological substance, a second polynucleotide comprising a second transcribable region with homology to a second target gene encoding a second biological substance, and a third polynucleotide comprising a third transcribable region with no effective homology to the first and second target genes wherein the third transcribable region comprises two segments complementary to each other in reverse orientation; wherein the first, second, and third transcribable regions are transcribed as a single-stranded RNA molecule; and wherein production of short interfering RNAs (siRNAs) is by cultivating the filamentous fungal strain under conditions to produce RNA transcripts of the double-stranded transcribable nucleic acid construct that are then converted to the siRNAs, which interact with RNA transcripts of the target genes to silence expression of the target genes encoding the first and second biological substances.

[18] The filamentous fungal strain of paragraph 17, wherein the first homologous region comprises at least 19 nucleotides of the first target gene.

[19] The filamentous fungal strain of paragraph 17 or 18, wherein the second homologous region comprises at least 19 nucleotides of the second target gene.

[20] The filamentous fungal strain of any of paragraphs 17-19, wherein the third transcribable region with no effective homology to the first and second target genes comprises at least 19 nucleotides.

[21] The filamentous fungal strain of paragraph 20, wherein the third transcribable region has no effective homology to the genome of the filamentous fungal strain.

[22] The filamentous fungal strain of paragraph 20, wherein the third transcribable region has homology to a third target gene.

[23] The filamentous fungal strain of any of paragraphs 17-20, wherein expression of the first target gene is reduced by at least 20%, at least 30%, at least 40%, at least 50%, at least 60%, at least 70%, at least 80%, at least 90%, or 100%.

[24] The filamentous fungal strain of any of paragraphs 17-23, wherein expression of the second target gene is reduced by at least 20%, at least 30%, at least 40%, at least 50%, at least 60%, at least 70%, at least 80%, at least 90%, or 100%.

[25] The filamentous fungal strain of paragraph 22-24, wherein expression of the third target gene is reduced by at least 20%, at least 30%, at least 40%, at least 50%, at least 60%, at least 70%, at least 80%, at least 90%, or 100%.

[26] The filamentous fungal strain of any of paragraphs 17-25, wherein the short interfering RNAs interact with RNA transcripts of one or more homologues of the target genes to silence expression of the one or more homologues of the target genes.

[27] The filamentous fungal strain of paragraph 26, wherein expression of the one or more homologues of the target genes is reduced by at least 20%, at least 30%, at least 40%, at least 50%, at least 60%, at least 70%, at least 80%, at least 90%, or 100%.

[28] The filamentous fungal strain of any of paragraphs 17-27, wherein the double-stranded transcribable nucleic acid construct further comprises at least one additional polynucleotide comprising an additional transcribable region with homology to an additional target gene encoding an additional biological substance.

[29] The filamentous fungal strain of paragraph 28, wherein the additional transcribable region with homology to the additional target gene comprises at least 19 nucleotides of the additional target gene.

[30] The filamentous fungal strain of paragraph 28 or 29, wherein expression of the additional target gene is reduced by at least 20%, at least 30%, at least 40%, at least 50%, at least 60%, at least 70%, at least 80%, at least 90%, or 100%.

[31] The filamentous fungal strain of any of paragraphs 28-30, wherein the short interfering RNAs interact with RNA transcripts of one or more homologues of the additional target gene to silence expression of the one or more homologues of the additional target gene.

[32] The filamentous fungal strain of paragraph 31, wherein expression of the one or more homologues of the additional target gene is reduced by at least 20%, at least 30%, at least 40%, at least 50%, at least 60%, at least 70%, at least 80%, at least 90%, or 100%.

[33] A method for producing a biological substance of interest, comprising: cultivating a filamentous fungal strain under conditions conducive for production of the biological substance of interest, wherein the filamentous fungal strain comprises a double-stranded transcribable nucleic acid construct comprising a promoter operably linked to a first polynucleotide comprising a first transcribable region with homology to a first target gene encoding a first biological substance, a second polynucleotide comprising a second transcribable region with homology to a second target gene encoding a second biological substance, and a third polynucleotide comprising a third transcribable region with no effective homology to the first and second target genes wherein the third transcribable region comprises two segments complementary to each other in reverse orientation; wherein the first, second, and third transcribable regions are transcribed as a single-stranded RNA molecule; wherein production of short interfering RNAs (siRNAs) is by cultivating the filamentous fungal strain under conditions to produce RNA transcripts of the double-stranded transcribable nucleic acid construct that are then converted to the siRNAs comprising sequences of the target genes to be silenced, which interact with RNA transcripts of the target genes to silence expression of the target genes encoding the first and second biological substances; and wherein the filamentous fungal strain comprises a fourth polynucleotide encoding the biological substance of interest.

[34] The method of paragraph 33, further comprising recovering the biological substance of interest from the cultivation medium.

[35] The method of paragraph 33 or 34, wherein the first transcribable region with homology to the first target gene comprises at least 19 nucleotides of the first target gene.

[36] The method of any of paragraphs 33-35, wherein the second transcribable region with homology to the second target gene comprises at least 19 nucleotides of the second target gene.

[37] The method of any of paragraphs 33-36, wherein the third transcribable region with no effective homology to the first and second target gene comprises at least 19 nucleotides.

[38] The method of paragraph 37, wherein the third transcribable region has no effective homology to the genome of the filamentous fungal strain.

[39] The method of paragraph 37, wherein the third transcribable region has homology to a third target gene.

[40] The method of any of paragraphs 33-39, wherein expression of the first target gene is reduced by at least 20%, at least 30%, at least 40%, at least 50%, at least 60%, at least 70%, at least 80%, at least 90%, or 100%.

[41] The method of any of paragraphs 33-40, wherein expression of the second target gene is reduced by at least 20%, at least 30%, at least 40%, at least 50%, at least 60%, at least 70%, at least 80%, at least 90%, or 100%.

[42] The method of paragraph 39-41, wherein expression of the third target gene is reduced by at least 20%, at least 30%, at least 40%, at least 50%, at least 60%, at least 70%, at least 80%, at least 90%, or 100%.

[43] The method of any of paragraphs 33-42, wherein the short interfering RNAs interact with RNA transcripts of one or more homologues of the target genes to silence expression of the one or more homologues of the target genes.

[44] The method of paragraph 43, wherein expression of the one or more homologues of the target genes is reduced by at least 20%, at least 30%, at least 40%, at least 50%, at least 60%, at least 70%, at least 80%, at least 90%, or 100%.

[45] The method of any of paragraphs 33-44, wherein the double-stranded transcribable nucleic acid construct further comprises at least one additional polynucleotide comprising an additional transcribable region with homology to an additional target gene encoding an additional biological substance.

[46] The method of paragraph 45, wherein the additional transcribable region with homology to the additional target gene comprises at least 19 nucleotides of the additional target gene.

[47] The method of paragraph 45 or 46, wherein expression of the additional target gene is reduced by at least 20%, at least 30%, at least 40%, at least 50%, at least 60%, at least 70%, at least 80%, at least 90%, or 100%.

[48] The method of any of paragraphs 45-47, wherein the short interfering RNAs interact with RNA transcripts of one or more homologues of the additional target gene to silence expression of the one or more homologues of the additional target gene.

[49] The method of paragraph 48, wherein expression of the one or more homologues of the additional target gene is reduced by at least 20%, at least 30%, at least 40%, at least 50%, at least 60%, at least 70%, at least 80%, at least 90%, or 100%.

[50] A method for identifying a gene encoding a biological substance of interest in a filamentous fungal cell, comprising: (a) transforming a population of the filamentous fungal host cell with a double-stranded transcribable nucleic acid construct comprising a promoter operably linked to a first polynucleotide comprising a first transcribable region with homology to a first target gene encoding a phenotypic marker, a second polynucleotide comprising a second transcribable region with homology to a second target gene encoding the biological substance of interest, and a third polynucleotide comprising a third transcribable region with no effective homology to the first and second target genes; wherein the third transcribable region comprises two segments complementary to each other in reverse orientation; wherein the first, second, and third transcribable regions are transcribed as a single-stranded RNA molecule; and wherein the double-stranded transcribable nucleic acid construct inserts into the genome of the filamentous fungal host cell; (b) producing short interfering RNAs (siRNAs), comprising sequences of the target genes to be silenced, by cultivating the filamentous fungal host cell under conditions to produce RNA transcripts of the double-stranded transcribable nucleic acid construct that are then converted to the siRNAs, which interact with RNA transcripts of the first target gene resulting in a phenotypic change of the transformed filamentous fungal host cell and interact with RNA transcripts of the second target gene silencing expression of the biological substance of interest; (c) selecting transformants from the transformed population of the filamentous fungal host cell which exhibit the phenotypic change; and (d) screening each of the selected transformants exhibiting the phenotypic change for silencing of the second target gene encoding the biological substance of interest by measuring the level of the biological substance produced by each of the transformants relative to the level of the biological substance produced by the filamentous fungal host cell.

[51] The method of paragraph 50, further comprising isolating the second target gene encoding the biological substance of interest.

[52] The method of paragraph 50 or 51, wherein the first transcribable region with homology to the first target gene comprises at least 19 nucleotides of the first target gene.

[53] The method of any of paragraphs 50-52, wherein the second transcribable region with homology to the second target gene comprises at least 19 nucleotides of the second target gene.

[54] The method of any of paragraphs 50-53, wherein the third transcribable region with no effective homology to the first and second target genes comprises at least 19 nucleotides.

[55] The method of any of paragraphs 50-54, wherein expression of the first target gene is reduced by at least 20%, at least 30%, at least 40%, at least 50%, at least 60%, at least 70%, at least 80%, at least 90%, or 100%.

[56] The method of any of paragraphs 50-55, wherein expression of the second target gene is reduced by at least 20%, at least 30%, at least 40%, at least 50%, at least 60%, at least 70%, at least 80%, at least 90%, or 100%.

[57] The method of any of paragraphs 50-56, wherein the short interfering RNAs interact with RNA transcripts of one or more homologues of the first and second target genes to silence expression of the one or more homologues of the first and second target genes.

[58] The method of paragraph 57, wherein expression of the one or more homologues of the target genes are reduced by at least 20%, at least 30%, at least 40%, at least 50%, at least 60%, at least 70%, at least 80%, at least 90%, or 100%.

[59] The method of any of paragraphs 50-58, wherein the double-stranded transcribable nucleic acid construct further comprises at least one additional polynucleotide comprising an additional transcribable region with homology to an additional target gene encoding an additional biological substance.

[60] The method of paragraph 59, wherein the additional transcribable region with homology to the additional target gene comprises at least 19 nucleotides of the additional target gene.

[61] The method of paragraph 59 or 60, wherein expression of the additional target gene is reduced by at least 20%, at least 30%, at least 40%, at least 50%, at least 60%, at least 70%, at least 80%, at least 90%, or 100%.

[62] The method of any of paragraphs 59-61, wherein the short interfering RNAs interact with RNA transcripts of one or more homologues of the additional target gene to silence expression of the one or more homologues of the additional target gene.

[63] The method of paragraph 62, wherein expression of the one or more homologues of the additional target gene is reduced by at least 20%, at least 30%, at least 40%, at least 50%, at least 60%, at least 70%, at least 80%, at least 90%, or 100%.

[64] A method for identifying a gene encoding a biological substance of interest in a filamentous fungal cell, comprising: (a) transforming a population of the filamentous fungal cell with a DNA library from the filamentous fungal cell wherein each member of the DNA library is cloned into a double-stranded transcribable nucleic acid construct comprising a promoter operably linked to a first polynucleotide comprising a first transcribable region with homology to a first target gene encoding a phenotypic marker, a second polynucleotide comprising a member of the DNA library as a second transcribable region with homology to a second target gene encoding the biological substance of interest, and a third polynucleotide comprising a third transcribable region with no effective homology to the first and second target genes; wherein the third transcribable region comprises two segments complementary to each other in reverse orientation; wherein the first, second, and third transcribable regions are transcribed as a single-stranded RNA molecule; and wherein the double-stranded transcribable nucleic acid construct inserts into the genome of the filamentous fungal cell; (b) producing short interfering RNAs (siRNAs), comprising sequences of the target genes to be silenced, by cultivating the transformed population of the filamentous fungal cell under conditions to produce RNA transcripts of the double-stranded transcribable nucleic acid construct that are then converted to the siRNAs, which interact with RNA transcripts of the first target gene resulting in a phenotypic change of the transformed filamentous fungal cell and interact with RNA transcripts of the second target gene silencing expression of the biological substance of interest; (c) selecting transformants from the transformed population of the filamentous fungal cell which exhibit the phenotypic change; and (d) screening each of the selected transformants exhibiting the phenotypic change for silencing of the second target gene encoding the biological substance of interest by measuring the level of the biological substance produced by each of the transformants relative to the level of the biological substance produced by the filamentous fungal cell.

[65] The method of paragraph 64, further comprising isolating the second target gene encoding the biological substance of interest.

[66] The method of paragraph 64 or 65, wherein the first transcribable region with homology to the first target gene comprises at least 19 nucleotides of the first target gene.

[67] The method of any of paragraphs 64-66, wherein the second transcribable region with homology to the second target gene comprises at least 19 nucleotides of the second target gene.

[68] The method of any of paragraphs 64-67, wherein the third transcribable region with no effective homology to the first and second target genes comprises at least 19 nucleotides.

[69] The method of any of paragraphs 64-68, wherein expression of the first target gene is reduced by at least 20%, at least 30%, at least 40%, at least 50%, at least 60%, at least 70%, at least 80%, at least 90%, or 100%.

[70] The method of any of paragraphs 64-69, wherein expression of the second target gene is reduced by at least 20%, at least 30%, at least 40%, at least 50%, at least 60%, at least 70%, at least 80%, at least 90%, or 100%.

[71] The method of any of paragraphs 64-70, wherein the short interfering RNAs interact with RNA transcripts of one or more homologues of the first and second target genes to silence expression of the one or more homologues of the first and second target genes.

[72] The method of paragraph 71, wherein expression of the one or more homologues of the target genes are reduced by at least 20%, at least 30%, at least 40%, at least 50%, at least 60%, at least 70%, at least 80%, at least 90%, or 100%.

[73] The method of any of paragraphs 64-72, wherein the double-stranded transcribable nucleic acid construct further comprises at least one additional polynucleotide comprising an additional transcribable region with homology to an additional target gene encoding an additional biological substance.

[74] The method of paragraph 73, wherein the additional transcribable region with homology to the additional target gene comprises at least 19 nucleotides of the additional target gene.

[75] The method of paragraph 73 or 74, wherein expression of the additional target gene is reduced by at least 20%, at least 30%, at least 40%, at least 50%, at least 60%, at least 70%, at least 80%, at least 90%, or 100%.

[76] The method of any of paragraphs 73-75, wherein the short interfering RNAs interact with RNA transcripts of one or more homologues of the additional target gene to silence expression of the one or more homologues of the additional target gene.

[77] The method of paragraph 76, wherein expression of the one or more homologues of the additional target gene is reduced by at least 20%, at least 30%, at least 40%, at least 50%, at least 60%, at least 70%, at least 80%, at least 90%, or 100%.

[78] A double-stranded transcribable nucleic acid construct comprising a promoter operably linked to a first polynucleotide comprising a first transcribable region with homology to a first target gene encoding a first biological substance, a second polynucleotide comprising a second transcribable region with homology to a second target gene encoding a second biological substance, and a third polynucleotide comprising a third transcribable region with no effective homology to the first and second target genes.

[79] A double-stranded transcribable nucleic acid construct comprising a promoter operably linked to a first polynucleotide comprising a first transcribable region with homology to a first target gene encoding a phenotypic marker, a second polynucleotide comprising a member of a DNA library as a second transcribable region with homology to a second target gene encoding a biological substance of interest, and a third polynucleotide comprising a third transcribable region with no effective homology to the first and second target genes.

[80] A vector comprising the double-stranded transcribable nucleic acid construct of paragraph 78 or 79.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A method for identifying a gene encoding a biological substance of interest in an *Aspergillus* cell, comprising:
   (a) transforming a population of the *Aspergillus* cell with a double-stranded transcribable nucleic acid construct comprising a promoter operably linked to a first polynucleotide comprising a first transcribable region with homology to a first target gene encoding a phenotypic marker, a second polynucleotide comprising a second transcribable region with homology to a second target gene encoding the biological substance of interest, and a third polynucleotide comprising a third transcribable region with no effective homology to the first and second target genes; wherein the third transcribable region comprises two segments complementary to each other in reverse orientation; wherein the first, second, and third transcribable regions are transcribed as a single-stranded RNA molecule; and wherein the double-stranded transcribable nucleic acid construct inserts into the genome of the *Aspergillus* cell;
   (b) producing short interfering RNAs (siRNAs), comprising sequences of the target genes to be silenced, by cultivating the *Aspergillus* cell under conditions to produce RNA transcripts of the double-stranded transcribable nucleic acid construct that are then converted to the siRNAs, which interact with RNA transcripts of the first target gene resulting in a phenotypic change of the transformed *Aspergillus* cell and interact with RNA transcripts of the second target gene silencing expression of the biological substance of interest;
   (c) selecting transformants from the transformed population of the *Aspergillus* cell which exhibit the phenotypic change; and
   (d) screening each of the selected transformants exhibiting the phenotypic change for silencing of the second target gene encoding the biological substance of interest by measuring the level of the biological substance produced by each of the transformants relative to the level of the biological substance produced by the *Aspergillus* cell.

2. The method of claim 1, further comprising isolating the second target gene encoding the biological substance of interest.

3. The method of claim 1, wherein expression of each of the target genes is reduced by at least 20%, at least 30%, at least 40%, at least 50%, at least 60%, at least 70%, at least 80%, at least 90%, or 100%.

4. The method of claim 1, wherein the first transcribable region with homology to the first target gene comprises at least 19 nucleotides of the first target gene.

5. The method of claim 1, wherein the second transcribable region with homology to the second target gene comprises at least 19 nucleotides of the second target gene.

6. The method of claim 1, wherein the third transcribable region with no effective homology to the first and second target genes comprises at least 19 nucleotides.

7. The method of claim 1, wherein expression of the first target gene is reduced by at least 20%, at least 30%, at least 40%, at least 50%, at least 60%, at least 70%, at least 80%, at least 90%, or 100%.

8. The method of claim 1, wherein expression of the second target gene is reduced by at least 20%, at least 30%, at least 40%, at least 50%, at least 60%, at least 70%, at least 80%, at least 90%, or 100%.

9. The method of claim 1, wherein the short interfering RNAs interact with RNA transcripts of one or more homologues of the first and second target genes to silence expression of the one or more homologues of the first and second target genes.

10. The method of claim 9, wherein expression of the one or more homologues of the target genes are reduced by at least 20%, at least 30%, at least 40%, at least 50%, at least 60%, at least 70%, at least 80%, at least 90%, or 100%.

11. The method of claim 1, wherein the double-stranded transcribable nucleic acid construct further comprises at least one additional polynucleotide comprising an additional transcribable region with homology to an additional target gene encoding an additional biological substance.

12. The method of claim 11, wherein the additional transcribable region with homology to the additional target gene comprises at least 19 nucleotides of the additional target gene.

13. The method of claim 11, wherein expression of the additional target gene is reduced by at least 20%, at least 30%, at least 40%, at least 50%, at least 60%, at least 70%, at least 80%, at least 90%, or 100%.

14. The method of claim 11, wherein the short interfering RNAs interact with RNA transcripts of one or more homologues of the additional target gene to silence expression of the one or more homologues of the additional target gene.

15. The method of claim 14, wherein expression of the one or more homologues of the additional target gene is reduced by at least 20%, at least 30%, at least 40%, at least 50%, at least 60%, at least 70%, at least 80%, at least 90%, or 100%.

16. The method of claim 1, wherein the *Aspergillus* cell is *Aspergillus niger*.

17. The method of claim 1, wherein the *Aspergillus* cell is *Aspergillus oryzae*.

* * * * *

SEQUENCE LISTING

```
<160> NUMBER OF SEQ ID NOS: 26

<210> SEQ ID NO 1
<211> LENGTH: 42
<212> TYPE: DNA
<213> ORGANISM: Artificial Sequence
<220> FEATURE:
<223> OTHER INFORMATION: ARTIFICIAL DNA PRIMER

<400> SEQUENCE: 1
gagtcagtga gcgaggaagc actgtggacc agacaggcgc ca                        42

<210> SEQ ID NO 2
<211> LENGTH: 42
<212> TYPE: DNA
<213> ORGANISM: Artificial Sequence
```

```
<220> FEATURE:
<223> OTHER INFORMATION: ARTIFICIAL DNA PRIMER

<400> SEQUENCE: 2
ctgcggccgc gggcccatgg tgctcagata ctacggctga tc                          42

<210> SEQ ID NO 3
<211> LENGTH: 6487
<212> TYPE: DNA
<213> ORGANISM: Artificial Sequence
<220> FEATURE:
<223> OTHER INFORMATION: The DNA of plasmid pSaMF2049004

<400> SEQUENCE: 3
tggtaactgt cagaccaagt ttactcatat atactttaga ttgatttaaa acttcattat        60
atactttaga ttgatttaaa acttcatttt taatttaaaa ggatctaggt gaagatcctt       120
tttgataatc tcatgaccaa atcccttaa cgtgagtttt cgttccactg agcgtcagac        180
cccgtagaaa agatcaaagg atcttcttga tccttttttt ttctgcgcgt aatctgctgc       240
ttgcaaacaa aaaaaccacc gctaccagcg gtggtttgtt tgccggatca agagctacca      300 actcttttc cgaaggtaac tggcttcagc agagcgcaga taccaaatac tgttcttcta       360
gtgtagccgt agttaggcca ccacttcaag aactctgtag caccgcctac atacctcgct       420
ctgctaatcc tgttaccagt ggctgctgcc agtggcgata gtcgtgtct taccgggttg        480 gactcaagac gatagttacc ggataaggcg cagcggtcgg gctgaacggg gggttcgtgc       540
acacagccca gcttggagcg aacgacctac accgaactga tacctacag cgtgagcta        600 tgagaaagcg ccacgcttcc cgaagggaga aaggcggaca ggtatccggt aagcggcagg       660
gtcggaacag gagagcgcac gagggagctt ccaggggga acgcctggta tctttatagt       720
cctgtcgggt ttcgccacct ctgacttgag cgtcgatttt tgtgatgctc gtcaggggg       780 cggagcctat ggaaaaacgc cagcaacgcg gcctttttac ggttcctggc cttttgctgg      840 cctttgctc acatgttctt tcctgcgtta tcccctgatt ctgtggataa ccgtattacc       900
gcctttgagt gagctgatac cgctcgccgc agccgaacga ccgagcgcag cgagtcagtg       960
agcgaggaag cggaagagcg cccaatacgc aaaccgcctc tccccgcgcg ttggccgatt     1020
cattaatgca gctggcacga caggtttccc gactggaaag cgggcagtga gcgcaacgca       1080
attaatgtga gttagctcac tcattaggca ccccaggctt tacactttat gcttccggct       1140
cgtatgttgt gtggaattgt gagcggataa caatttcaca caggaaacag ctatgaccat       1200
gattacgaat tgtttaaacg actgtggacc agacaggcgc cactcggccg gccacagct       1260 gcttgggtgt tgaccgggag cggaccaatt aaggactcga acgaccgcgg ggttcaaatg       1320
caaacaagta caacacgcag caaacgaagc agcccaccac tgcgttgatg cccagtttga       1380
ctgtccgaaa tccaccggaa aggtggaaac atactatgta acaatcagag ggaagaaaaa       1440
atttttatcg acgaggcagg atagtgactg atggtgggt catggtcggg tctccgagcg       1500
aaagagaacc aaggaaacaa gatcaacgag gttggtgtac ccaaaaggcc gcagcaacaa      1560
gagtcatcgc ccaaaagtca acagtctgga agagactccg ccgtgcagat tctgcgtcgg       1620
tcccgcacat gcgtggtggg ggcattaccc ctccatgtcc aatgataagg gcggcggtcg       1680
agggcttaag cccgcccact aattcgcctt ctcgcttgcc cctccatata aggattcccc       1740
ctccttcccc tcccacaact ttttttcctt ttctctctct tcgtccgcatc agtacgtata      1800 tctttccccc atacctcctt tcctactctt cttccattca ttcaactctt ctccttactg      1860
```

```
acatctgttt tgctcagtac ctctacgcga tcagccgtag tatctgagca catgggcccg    1920
cggccgcaga tctacgcgta ctagtgctag cccgggcatg cgttaattaa ctagaggtga    1980
ctgacacctg gcggtagaca atcaatccat ttcgctatag ttaaaggatg gggatgaggg    2040
caattggtta tatgatcatg tatgtagtgg gtgtgcataa tagtagtgaa atggaagcca    2100
agtcatgtga ttgtaatcga ccgacggaat tgaggatatc cggaaataca gacaccgtga    2160
aagccatgct cttccttcg tgtagaagac cagacagaca gtccctgatt tacccttgca     2220
caaagcacta gaaaattagc attccatcct tctctgcttg ctctgctgat atcactgtca    2280
ttcaatgcat ctggaaacgc aaccctgaag ggattcttcc tttgagagat ggaagcgtgt    2340
catatctctt cggttctacg gcaggttttt ttctgctctt tcgtagcatg gcatggtcac    2400
ttcagcgctt atttacagtt gctggtattg atttcttgtg caaattgcta tctgacactt    2460
attagctatg gagtcaccac atttcccagc aacttcccca cttcctctgc aatcgccaac    2520
gtcctctctt cactgagtct ccgtccgata acctgcactg caaccggtgc cccatgatac    2580
gcctccggat catactcttc ctgcacgagg gcatcaagct cactaaccgc cttgaaactc    2640
tcattcttct tatcgatgtt cttatccgca aggtaaccg gaacaaccac gctcgtgaaa     2700
tccagcaggt tgatcacaga ggcataccca tagtaccgga actggtcatg ccgtaccgca    2760
gcggtaggcg taatcggcgc gatgatggcg tccagttcct tcccggcctt ttcttcagcc    2820
tcccgccatt tctcaaggta ctccatctgg taattccact tctggagatg cgtgtcccag    2880
agctcgttca tgttaacagc tttgatgttc gggttcagta ggtctttgat atttggagtc    2940
gccggctcgc cggatgcact gatatcgcgc attacgtcgg cgctgccgtc agccgcgtag    3000
atatgggaga tgagatcgtg gccgaaatcg tgcttgtatg gcgtccacgg ggtcacggtg    3060
tgaccggctt tggcgagtgc ggcgacggtg gtttccacgc cgcgcaggat aggagggtgt    3120
ggaaggacat tgccgtcgaa gttgtagtag ccgatattga gcccgccgtt cttgatcttg    3180
gaggcaataa tgtccgactc ggactggcgc cagggcatgg ggatgacctt ggagtcgtat    3240
ttccaaggct cctgaccgag gacggatttg tgaagaggc ggaggtctaa catacttcat     3300
cagtgactgc cggtctcgta tatagtataa aaagcaagaa aggaggacag tggaggcctg    3360
gtatagagca ggaaaagaag gaagaggcga aggactcacc ctcaacagag tgcgtaatcg    3420
gcccgacaac gctgtgcacc gtctcctgac cctccatgct gttcgccatc tttgcatacg    3480
gcagccgccc atgactcggc cttagaccgt acaggaagtt gaacgcggcc ggcactcgaa    3540
tcgagccacc gatatccgtt cctacaccga tgacgccacc acgaatccca acgatcgcac    3600
cctcaccacc agaactgccg ccgcacgacc agttcttgtt gcgtgggttg acggtgcgcc    3660
cgatgatgtt gttgactgtc tcgcagacca tcagggtctg cgggacagag gtcttgacgt    3720
agaagacggc accggctttg cggagcatgg ttgtcagaac cgagtcccct tcgtcgtact    3780
tgtttagcca tgagatgtag cccattgatg tttcgtagcc ctggtggcat atgttagctg    3840
acaaaaaggg acatctaacg acttaggggc aacggtgtac cttgactcga agctggtctt    3900
tgagagagat ggggaggcca tgaagtggac caacgggtct cttgtgcttt gcgtagtatt    3960
catcgagttc ccttgcctgc gcgagagcgg cgtcagggaa gaactcgtgg gcgcagtttg    4020
tctgcacaga agccagcgtc agcttgatag tcccataagg tggcgttgtt acatctccct    4080
gagaggtaga ggggacccta ctaactgctg ggcgattgct gcccgtttac agaatgctag    4140
cgtaacttcc accgaggtca actctccggc cgccagcttg acacaagat ctgcagcgga     4200
ggcctctgtg atcttcagtt cggcctctga aaggatcccc gatttctttg ggaaatcaat    4260
```

```
aacgctgtct tccgcaggca gcgtctggac tttccattca tcagggatgg ttttttgcgag    4320
gcgggcgcgc ttatcagcgg ccagttcttc ccaggattga ggcattctgt gttagcttat    4380
agtcaggatg ttggctcgac gagtgtaaac tgggagttgg catgagggtt atgtaggctt    4440
ctttagcccc gcatccccct cattctcctc attgatcccg ggggagcgga tggtgttgat    4500
aagagactaa ttatagggtt tagctggtgc ctagctggtg attggctggc ttcgccgaat    4560
tttacgggcc aaggaaagct gcagaaccgc ggcactggta acggtaatt aagctatcag     4620
ccccatgcta acgagtttaa attacgtgta ttgctgataa acaccaacag agctttactg    4680
aaagatggga gtcacggtgt ggcttcccca ctgcgattat tgcacaagca gcgagggcga    4740
acttgactgt cgtcgctgag cagcctgcag tcaaacatac atatatatca accgcgaaga    4800
cgtctggcct tgtagaacac gacgctccct agcaacacct gccgtgtcag cctctacggt    4860
tgttacttgc attcaggatg ctctccagcg ggcgagctat tcaaaatatt caaagcaggt    4920
atctcgtatt gccaggattc agctgaagca acaggtgcca aggaaatctg cgtcggttct    4980
catctgggct tgctcggtcc tggcgtagaa tgcatcctag agtttaaaca gcttggcact    5040
ggccgtcgtt ttacaacgtc gtgactggga aaaccctggc gttacccaac ttaatcgcct    5100
tgcagcacat ccccctttcg ccagctggcg taatagcgaa gaggcccgca ccgatcgccc    5160
ttcccaacag ttgcgcagcc tgaacggcga atggcgcctg atgcggtatt ttctccttac    5220
gcatctgtgc ggtatttcac accgcatatg gtgcactctc agtacaatct gctctgatgc    5280
cgcatagtta agccagcccc gacacccgcc aacacccgct gacgcgccct gacgggcttg    5340
tctgctcccg gcatccgctt acagacaagc tgtgaccgtc tccgggagct gcatgtgtca    5400
gaggttttca ccgtcatcac cgaaacgcgc gagacgaaag gcctcgtga tacgcctatt     5460
tttataggtt aatgtcatga taataatggt ttcttagacg tcaggtggca cttttcgggg    5520
aaatgtgcgc ggaaccccta tttgtttatt tttctaaata cattcaaata tgtatccgct    5580
catgagacaa taaccctgat aaatgcttca ataatattga aaaggaaga gtatgagtat     5640
tcaacatttc cgtgtcgccc ttattccctt ttttgcggca ttttgccttc ctgttttgc     5700
tcacccagaa acgctggtga agtaaaaga tgctgaagat cagttgggtg cacgagtggg    5760
ttacatcgaa ctggatctca acagcggtaa gatccttgag agttttcgcc ccgaagaacg    5820
ttttccaatg atgagcactt ttaaagttct gctatgtggc gcggtattat cccgtattga    5880
cgccgggcaa gagcaactcg gtcgccgcat acactattct cagaatgact tggttgagta    5940
ctcaccagtc acagaaaagc atcttacgga tggcatgaca gtaagagaat tatgcagtgc    6000
tgccataacc atgagtgata acactgcggc caacttactt ctgacaacga tcggaggacc    6060
gaaggagcta accgcttttt tgcacaacat gggggatcat gtaactcgcc ttgatcgttg    6120
ggaaccggag ctgaatgaag ccataccaaa cgacgagcgt gacaccacga tgcctgtagc    6180
aatggcaaca acgttgcgca aactattaac tggcgaacta cttactctag cttcccggca    6240
acaattaata gactggatgg aggcggataa agttgcagga ccacttctgc gctcggccct    6300
tccggctggc tggtttattg ctgataaatc tggagccggt gagcgtgggt ctcgcggtat    6360
cattgcagca ctggggccag atggtaagcc ctcccgtatc gtagttatct acacgacggg    6420
gagtcaggca actatggatg aacgaaatag acagatcgct gagataggtg cctcactgat    6480
taagcat                                                              6487
```

<210> SEQ ID NO 4

<211> LENGTH: 6387
<212> TYPE: DNA
<213> ORGANISM: Aspergillus niger

<400> SEQUENCE: 4

| | | | | | |
|---|---|---|---|---|---|
| atggagggtc | catctcgtgt | gtaccttttt | ggagaccaga | ccagcgacat | cgaagctggc | 60 |
| ctgcgccgtc | tgctccaagc | gaagaatagt | accattgtcc | agtcctttt | ccagcaatgc | 120 |
| ttccatgcaa | ttcgtcaaga | gatcgcgaag | ctcccgccgt | ctcatcggaa | gctcttccca | 180 |
| cgcttcacga | gcatcgttga | tctcctttcc | aggagtcgtg | aatcaggtcc | tagccctgtc | 240 |
| ctggagagtg | cattgacatg | catctaccaa | ttggggttgtt | tcattcactt | ttacggggat | 300 |
| cttggacatg | actaccctac | accctccaac | agccatcttg | ttggcctgtg | cactggtgtt | 360 |
| ctgagctgca | cggctgtaag | ttgcgccaga | aatgttggag | agcttattcc | agctgcagtg | 420 |
| gaatcggttg | taattgcact | gcgactggga | atctgcgttt | tcgagttcg | agaactggtg | 480 |
| gactccgccg | attccgagtc | aacatgctgg | tcagcgttgg | tttctggaat | cagtgaagca | 540 |
| gaggctagcc | acctgatcga | cgagtacagt | agtaagaagg | ctactccgcc | ttcttcgaaa | 600 |
| ccgtatatca | gcgcggtaag | ctctaatggc | gttactgtca | gcgcaccacc | tacggtactt | 660 |
| gatgaattcg | tcgagacctg | catttccaag | aattacaagc | cagtgaaggc | cctattcat | 720 |
| ggcccgtacc | atgcgccaca | tctgtatgat | gataaggata | tcgaccgcat | cctgcagcag | 780 |
| tcctctgctc | tagaaggact | gaccggctgt | tcacccgtta | ttcccatcat | ctccagtaac | 840 |
| actggaaagc | cgatcaaggc | caagtccatc | aaagatctct | tcaaggtcgc | actggaggag | 900 |
| atactcctac | gacgactatg | ctgggacaag | gtcacggagt | cctgcacatc | agtctgcaag | 960 |
| accggcacaa | accactcttg | caaattgttt | ccgatctcga | gtagcgccac | tcaaagtttg | 1020 |
| ttcacagtcc | tcaagaaggc | cggtgtgagc | atcagcttgg | agactggggt | aggagagatc | 1080 |
| gcgacgaacc | cagaaatgcg | gaaccttact | ggcaaggcag | aaaattcaaa | gattgctatc | 1140 |
| attggtatgt | ctgaagatt | tcctgactcg | gatggtacgg | agagcttctg | gaacctcctg | 1200 |
| tacaaaggac | tcgacgtaca | tcgcaaagtc | cccgcagacc | gttgggacgt | tgatgcccac | 1260 |
| gtcgacatga | ccgggtcaaa | gagaaacaca | agcaaagtgg | cttacggttg | ctggatcaac | 1320 |
| gaacccggcc | tgtttgaccc | ccgattcttc | aacatgtcgc | ctcgggaagc | actccaagca | 1380 |
| gatcctgcac | aacgtcttgc | gttgcttaca | gcgtacgagg | ctctcgagat | ggctggcttc | 1440 |
| atcccggata | gctctccatc | gacgcagagg | gaccgtgtgg | gtattttcta | cggaatgacc | 1500 |
| agtgacgact | accgtgagat | caacagcggc | caggacattg | atacctattt | catccctggc | 1560 |
| ggtaaccgag | catttacgcc | gggtcggata | aactactact | tcaaatttag | cggccccagt | 1620 |
| gtgagcgttg | acacagcgtg | ctcgtctagt | cttgctgcta | tccacatggc | ttgcaattcg | 1680 |
| atctggagaa | atgactgcga | tgccgccatc | actggaggtg | tgaacattct | gaccaaccct | 1740 |
| gacaaccacg | ccgtctggaa | tcggggccat | ttcctgtcca | ccactggcaa | ctgtaacacc | 1800 |
| tttgatgacg | gcgccgacgg | ctactgtaga | gcggacggag | ttggaagcat | cgttttgaag | 1860 |
| cggcttgaag | atgccgaggc | cgacaacgac | ccgatcctgg | ccgtcatcaa | cggtgcttac | 1920 |
| accaaccact | cggcggaggc | cgtgtcaatc | actcgtcccc | atgttggcgc | gcaagcattc | 1980 |
| atcttcaaca | agctgctcaa | tgatgcgaat | atcgaccta | aggacgtgag | ctacgtggaa | 2040 |
| atgcatggca | ctggaactca | agcaggtgat | gcagtcgaaa | tgcagtccgt | tcttgacgtc | 2100 |
| ttcgcaccag | actaccgccg | gggtccggt | caatcgcttc | atatcggttc | tgccaaggca | 2160 |
| aacattggac | acggtgaatc | cgcatcagga | gtgactgctc | ttgtcaaggt | cctcctaatg | 2220 |

```
atgagagaga acatgattcc tcctcattgt ggtatcaaga ccaagatcaa ttccaatttc    2280
ccgacagact tggcgaagcg caatgttcat atcgccttcc aacccactcc ctggaatcgg    2340
ccagcttcag gaaagcggcg aactttcgtc aacaactttt ctgctgctgg tggtaacact    2400
gctcttctac tggaagatgc tcccataccg gaacgccaag ggcaggaccc caggtcgttc    2460
catttggtct ccgtgtcagc aagatcccag tctgcattga agaacaacgt cgaagctctg    2520
gtgaagtaca ttgactctca gggcaagtcc tttggtgtga agagactga attccttcca    2580 aacctggcgt acacgaccac cgcacgccgt atccaccatc ccttccgtgt cactgcggtt    2640
ggagcgaacc tacaatcact gcgtgactcg ctgcatggtg ctttgcaccg tgagacatat    2700
accccagttc cctcaacggc tcctggtatt ggtttcgtct tcaccggcca aggagcccaa    2760
tactccggaa tgggcaagga actctaccgc agttgtttcc aattccgaac caccattgag    2820
cattttgact gcatcgcaag aagccagggc cttccttcta tccttcctct tgtcgatgga    2880
agcgtggctg tcgaagaact tagccctgtc gtggtacaag tgggaactac ctgtgtacaa    2940
atggctctag taaattactg gactgctctg ggtgtgaagc cggcctttat catcggacac    3000
agtcttggag actatgcagc ccttaacacg gccggtgttc tatccaccag cgatacaatc    3060
tatctttgtg gccggcgtgc tcagttgctg acgaaggaat gcaagattgg gacacattcg    3120
atgctggcca tcaaggcgtc cctggcgagg gtcaaacatt tcctcagaga cgagctccac    3180
gaagtctctt gtgttaacgc acctgcggag accgtcgtca gcggccttgt cgctgatatc    3240
gacgagttgg ctcagaaatg ctccacagag ggtttgaagt caaccaagct caaggttcct    3300
tacgcgttcc attcctctca ggttgatcct atcttggagg cctcgaaga tattgcccaa    3360 ggtgtcacct tccacaagcc gacaacacct ttcgtctcag ccctgttcgg ggaagtgatc    3420
accgatgcta actgggagtg tctcggcccc aagtacctgc gcgatcattg cagaaagacg    3480
gtcaacttcc ttggcggcgt ggaggctacg aggcatgcga agctgaccaa tgacaagact    3540 ctgtggggttg agatcggctc acataccatt tgctctggaa tgatcaaagc aactcttgga    3600
ccgcaagtta caacggttgc atctctacgc cgcgaagaag atacctggaa ggtccttcg    3660 aacagtcttg cgagccttca tctggcgggt attgatatca actggaagca atatcaccag    3720
gactttagct cctctctcca ggtcctccgc ctcccagcct acaagtggga tctcaagaac    3780
tactggattc cctataccaa caacttctgc ctgagcaagg gcgctccagt tgcgacagta    3840
gcggcagggc cacagcatga gtacctgaca accgcggctc agaaggtcat tgagactcga    3900
agtgatggag caacagctac agtcgtgata gagaacgaca ttgctgatcc cgagctcaac    3960
cgcgtcattc aaggccataa ggtcaacggt actgctttgt gtccctcatc actatatgcc    4020
gacatctctc aaacgcttgc agagtatctc atcaaaaagt acaagcctga gtacgacgga    4080
cttggactgg atgtgtgtga ggtcacagtg ccacgaccac tgattgcgaa aggcggacag    4140 cagctctttta gagtatctgc gacagcggat tgggcggaga agaagacaac ccttcagata    4200
tattcagtca ctgcggaggg gaagaagacg gctgaccacg caacttgcac tgtccgattc    4260
tttgactgcg ctgctgcgga ggcggaatgg aaacgagttt cctaccttgt caagaggagc    4320
attgaccgac tgcatgatat cgccgaaaat ggtgacgctc accgtcttgg tagaggcatg    4380
gtttacaaac tcttcgctgc cttggttgat tatgacgaca acttcaagtc cattcgcgag    4440
gttattcttg acagtgaaca gcacgaagcg actgcacgcg tcaagttcca agcaccacaa    4500
ggcaatttcc accgaaaccc gttctggatt gacagttttg acacctgtc tgggttcatc    4560
```

```
atgaacgcaa gcgatgcaac cgactccaag aaccaggtct tgtcaatca cggatgggac    4620 tccatgcgtt gtttgaagaa gttctcgcct gatgtcacct acaggactta tgttagaatg    4680
cagccttgga aagactccat ctgggctggt gatgtctacg ttttcgatgg ggatgatatc    4740
gttgcggtgt atggtgcagt caagttccaa gccttatcac gcaagattct cgataccggtc   4800 ctacctccaa gtcgtgctag cgccccggcc ccggcgaagc ctgctgctaa gcccagcgcc    4860
ccaagcttgg tcaaacgggc acttaccatc ctcgcagagg aagtgggtct gtctgaatcc    4920
gagattacgg atgatctggt cttcgcagac tacggtgtgg actcccttct ttcgttgacg    4980
gtcacgggca ggtatcgtga agagctggat atcgatctcg aatcctccat cttcatcgac    5040
cagccgaccg tgaaagactt caagcagttc ttggccccaa tgagccaggg agaagccagc    5100
gatgggtcca ccagtgaccc agagtctagt agctccttca atggtggctc ttcaacagac    5160
gagtccagtg ctgggtcccc tgtcagctca ccaccaaatg agaaggttac gcaggtcgag    5220
cagcatgcta cgataaagga gattcgcgcc atttttggccg atgagattgg tgttacggag    5280
gaggagctga aggacgatga gaacttggga gagatgggga tggactctct gctttcgctt    5340
acggtgcttg gtaggatccg tgagacattg atctggatc taccgggcga gttcttcatc    5400
gagaatcaaa ctctgaatga cgtggaggat gcattgggcc tcaaacccaa ggcagctcct    5460
gcgcctgcgc ctgcgcctgc tcccgtaccc gcacccgtgt ccgcgcccat attgaaggag    5520
cctgtcccca acgcaaactc taccatcatg gcccgggcga gcccgcaccc tcgatcaacc    5580
tccattctgt tgcaaggaaa cccgaaaacc gcgaccaaga ccctgttcct gttccctgat    5640
gggtctggct ccgcaacatc gtatgcaacc attcccggag tgtccccgga cgtgtgtgtc    5700
tacggattga actgcccgta catgaagact ccagagaagc tcaagtatcc ccttgctgag    5760
atgacattcc cctatctggc cgagatccgc cgcagacagc ccaagggccc gtacaacttc    5820
ggtggatggt ctgcaggtgg tatttgcgcc tatgatgccg ctcgctacct aatccttgaa    5880
gagggcgaac aggttgaccg attgcttctt cttgactcgc ccttccccat ggcttagag     5940 aagttgccca ctcggctgta cggcttcatc aactcaatgg gtctctttgg tgaaggcaac    6000
aaggctcccc cggcctggtt gctccctcat ttcctggcct tcattgattc cctcgatacc    6060
tacaaggccg tccccctccc cttttgacgat ccgaagtggg ccaagaagat gcccaagaca    6120
ttcatggtct gggccaagga cggtatctgc agcaagccgg atgacccgtg gcccgagccg    6180
gacccggacg gcaagccgga cacgagagag atggtctggc ctcctcaagaa ccggaccgac    6240 atgggaccca acaagtggga cacactcgtc gggcccaaa acgtcggtgg aatcactgtg    6300
atagagggtg cgaatcattt caccatgact ttggacccca aggctaaaga attgggctcg    6360
ttcattggca acgccatggc caattaa                                       6387
```

<210> SEQ ID NO 5
<211> LENGTH: 2128
<212> TYPE: PRT
<213> ORGANISM: Aspergillus niger

<400> SEQUENCE: 5

Met Glu Gly Pro Ser Arg Val Tyr Leu Phe Gly Asp Gln Thr Ser Asp
1               5                   10                  15

Ile Glu Ala Gly Leu Arg Arg Leu Leu Gln Ala Lys Asn Ser Thr Ile
            20                  25                  30

Val Gln Ser Phe Phe Gln Gln Cys Phe His Ala Ile Arg Gln Glu Ile
        35                  40                  45

-continued

```
Ala Lys Leu Pro Pro Ser His Arg Lys Leu Phe Pro Arg Phe Thr Ser
 50                  55                  60
Ile Val Asp Leu Leu Ser Arg Ser Arg Glu Ser Gly Pro Ser Pro Val
 65                  70                  75                  80
Leu Glu Ser Ala Leu Thr Cys Ile Tyr Gln Leu Gly Cys Phe Ile His
                 85                  90                  95
Phe Tyr Gly Asp Leu Gly His Asp Tyr Pro Thr Pro Ser Asn Ser His
                100                 105                 110
Leu Val Gly Leu Cys Thr Gly Val Leu Ser Cys Thr Ala Val Ser Cys
                115                 120                 125
Ala Arg Asn Val Gly Glu Leu Ile Pro Ala Ala Val Glu Ser Val Val
130                 135                 140
Ile Ala Leu Arg Leu Gly Ile Cys Val Phe Arg Val Arg Glu Leu Val
145                 150                 155                 160
Asp Ser Ala Asp Ser Glu Ser Thr Cys Trp Ser Ala Leu Val Ser Gly
                165                 170                 175
Ile Ser Glu Ala Glu Ala Ser His Leu Ile Asp Glu Tyr Ser Ser Lys
                180                 185                 190
Lys Ala Thr Pro Pro Ser Ser Lys Pro Tyr Ile Ser Ala Val Ser Ser
                195                 200                 205
Asn Gly Val Thr Val Ser Ala Pro Pro Thr Val Leu Asp Glu Phe Val
210                 215                 220
Glu Thr Cys Ile Ser Lys Asn Tyr Lys Pro Val Lys Ala Pro Ile His
225                 230                 235                 240
Gly Pro Tyr His Ala Pro His Leu Tyr Asp Asp Lys Asp Ile Asp Arg
                245                 250                 255
Ile Leu Gln Gln Ser Ser Ala Leu Glu Gly Leu Thr Gly Cys Ser Pro
                260                 265                 270
Val Ile Pro Ile Ile Ser Ser Asn Thr Gly Lys Pro Ile Lys Ala Lys
                275                 280                 285
Ser Ile Lys Asp Leu Phe Lys Val Ala Leu Glu Glu Ile Leu Leu Arg
                290                 295                 300
Arg Leu Cys Trp Asp Lys Val Thr Glu Ser Cys Thr Ser Val Cys Lys
305                 310                 315                 320
Thr Gly Thr Asn His Ser Cys Lys Leu Phe Pro Ile Ser Ser Ser Ala
                325                 330                 335
Thr Gln Ser Leu Phe Thr Val Leu Lys Lys Ala Gly Val Ser Ile Ser
                340                 345                 350
Leu Glu Thr Gly Val Gly Glu Ile Ala Thr Asn Pro Glu Met Arg Asn
                355                 360                 365
Leu Thr Gly Lys Ala Glu Asn Ser Lys Ile Ala Ile Ile Gly Met Ser
                370                 375                 380
Gly Arg Phe Pro Asp Ser Asp Gly Thr Glu Ser Phe Trp Asn Leu Leu
385                 390                 395                 400
Tyr Lys Gly Leu Asp Val His Arg Lys Val Pro Ala Asp Arg Trp Asp
                405                 410                 415
Val Asp Ala His Val Asp Met Thr Gly Ser Lys Arg Asn Thr Ser Lys
                420                 425                 430
Val Ala Tyr Gly Cys Trp Ile Asn Glu Pro Gly Leu Phe Asp Pro Arg
                435                 440                 445
Phe Phe Asn Met Ser Pro Arg Glu Ala Leu Gln Ala Asp Pro Ala Gln
450                 455                 460
Arg Leu Ala Leu Leu Thr Ala Tyr Glu Ala Leu Glu Met Ala Gly Phe
```

```
            465                 470                 475                 480
        Ile Pro Asp Ser Ser Pro Ser Thr Gln Arg Asp Arg Val Gly Ile Phe
                            485                 490                 495
        Tyr Gly Met Thr Ser Asp Asp Tyr Arg Glu Ile Asn Ser Gly Gln Asp
                    500                 505                 510
        Ile Asp Thr Tyr Phe Ile Pro Gly Gly Asn Arg Ala Phe Thr Pro Gly
                515                 520                 525
        Arg Ile Asn Tyr Tyr Phe Lys Phe Ser Pro Ser Val Ser Val Asp
            530                 535                 540
        Thr Ala Cys Ser Ser Ser Leu Ala Ala Ile His Met Ala Cys Asn Ser
        545                 550                 555                 560
        Ile Trp Arg Asn Asp Cys Asp Ala Ala Ile Thr Gly Val Asn Ile
                        565                 570                 575
        Leu Thr Asn Pro Asp Asn His Ala Gly Leu Asp Arg Gly His Phe Leu
                    580                 585                 590
        Ser Thr Thr Gly Asn Cys Asn Thr Phe Asp Asp Gly Ala Asp Gly Tyr
                595                 600                 605
        Cys Arg Ala Asp Gly Val Gly Ser Ile Val Leu Lys Arg Leu Glu Asp
            610                 615                 620
        Ala Glu Ala Asp Asn Asp Pro Ile Leu Ala Val Ile Asn Gly Ala Tyr
        625                 630                 635                 640
        Thr Asn His Ser Ala Glu Ala Val Ser Ile Thr Arg Pro His Val Gly
                        645                 650                 655
        Ala Gln Ala Phe Ile Phe Asn Lys Leu Leu Asn Asp Ala Asn Ile Asp
                    660                 665                 670
        Pro Lys Asp Val Ser Tyr Val Glu Met His Gly Thr Gly Thr Gln Ala
                675                 680                 685
        Gly Asp Ala Val Glu Met Gln Ser Val Leu Asp Val Phe Ala Pro Asp
            690                 695                 700
        Tyr Arg Arg Gly Pro Gly Gln Ser Leu His Ile Gly Ser Ala Lys Ala
        705                 710                 715                 720
        Asn Ile Gly His Gly Glu Ser Ala Ser Gly Val Thr Ala Leu Val Lys
                        725                 730                 735
        Val Leu Leu Met Met Arg Glu Asn Met Ile Pro Pro His Cys Gly Ile
                    740                 745                 750
        Lys Thr Lys Ile Asn Ser Asn Phe Pro Thr Asp Leu Ala Lys Arg Asn
                755                 760                 765
        Val His Ile Ala Phe Gln Pro Thr Pro Trp Asn Arg Pro Ala Ser Gly
            770                 775                 780
        Lys Arg Arg Thr Phe Val Asn Asn Phe Ser Ala Ala Gly Gly Asn Thr
        785                 790                 795                 800
        Ala Leu Leu Leu Glu Asp Ala Pro Ile Pro Glu Arg Gln Gly Gln Asp
                        805                 810                 815
        Pro Arg Ser Phe His Leu Val Ser Val Ser Ala Arg Ser Gln Ser Ala
                    820                 825                 830
        Leu Lys Asn Asn Val Glu Ala Leu Val Lys Tyr Ile Asp Ser Gln Gly
                835                 840                 845
        Lys Ser Phe Gly Val Lys Glu Thr Glu Phe Leu Pro Asn Leu Ala Tyr
            850                 855                 860
        Thr Thr Thr Ala Arg Arg Ile His His Pro Phe Arg Val Thr Ala Val
        865                 870                 875                 880
        Gly Ala Asn Leu Gln Ser Leu Arg Asp Ser Leu His Gly Ala Leu His
                        885                 890                 895
```

-continued

Arg Glu Thr Tyr Thr Pro Val Pro Ser Thr Ala Pro Gly Ile Gly Phe
            900                 905                 910

Val Phe Thr Gly Gln Gly Ala Gln Tyr Ser Gly Met Gly Lys Glu Leu
            915                 920                 925

Tyr Arg Ser Cys Phe Gln Phe Arg Thr Thr Ile Glu His Phe Asp Cys
            930                 935                 940

Ile Ala Arg Ser Gln Gly Leu Pro Ser Ile Leu Pro Leu Val Asp Gly
945                 950                 955                 960

Ser Val Ala Val Glu Glu Leu Ser Pro Val Val Gln Val Gly Thr
                965                 970                 975

Thr Cys Val Gln Met Ala Leu Val Asn Tyr Trp Thr Ala Leu Gly Val
            980                 985                 990

Lys Pro Ala Phe Ile Ile Gly His Ser Leu Gly Asp Tyr Ala Ala Leu
            995                 1000                1005

Asn Thr Ala Gly Val Leu Ser Thr Ser Asp Thr Ile Tyr Leu Cys
    1010                1015                1020

Gly Arg Arg Ala Gln Leu Leu Thr Lys Glu Cys Lys Ile Gly Thr
    1025                1030                1035

His Ser Met Leu Ala Ile Lys Ala Ser Leu Ala Glu Val Lys His
    1040                1045                1050

Phe Leu Arg Asp Glu Leu His Glu Val Ser Cys Val Asn Ala Pro
    1055                1060                1065

Ala Glu Thr Val Val Ser Gly Leu Val Ala Asp Ile Asp Glu Leu
    1070                1075                1080

Ala Gln Lys Cys Ser Thr Glu Gly Leu Lys Ser Thr Lys Leu Lys
    1085                1090                1095

Val Pro Tyr Ala Phe His Ser Ser Gln Val Asp Pro Ile Leu Glu
    1100                1105                1110

Ala Phe Glu Asp Ile Ala Gln Gly Val Thr Phe His Lys Pro Thr
    1115                1120                1125

Thr Pro Phe Val Ser Ala Leu Phe Gly Glu Val Ile Thr Asp Ala
    1130                1135                1140

Asn Trp Glu Cys Leu Gly Pro Lys Tyr Leu Arg Asp His Cys Arg
    1145                1150                1155

Lys Thr Val Asn Phe Leu Gly Gly Val Glu Ala Thr Arg His Ala
    1160                1165                1170

Lys Leu Thr Asn Asp Lys Thr Leu Trp Val Glu Ile Gly Ser His
    1175                1180                1185

Thr Ile Cys Ser Gly Met Ile Lys Ala Thr Leu Gly Pro Gln Val
    1190                1195                1200

Thr Thr Val Ala Ser Leu Arg Arg Glu Glu Asp Thr Trp Lys Val
    1205                1210                1215

Leu Ser Asn Ser Leu Ala Ser Leu His Leu Ala Gly Ile Asp Ile
    1220                1225                1230

Asn Trp Lys Gln Tyr His Gln Asp Phe Ser Ser Leu Gln Val
    1235                1240                1245

Leu Arg Leu Pro Ala Tyr Lys Trp Asp Leu Lys Asn Tyr Trp Ile
    1250                1255                1260

Pro Tyr Thr Asn Asn Phe Cys Leu Ser Lys Gly Ala Pro Val Ala
    1265                1270                1275

Thr Val Ala Ala Gly Pro Gln His Glu Tyr Leu Thr Thr Ala Ala
    1280                1285                1290

-continued

```
Gln Lys Val Ile Glu Thr Arg Ser Asp Gly Ala Thr Ala Thr Val
1295                1300                1305

Val Ile Glu Asn Asp Ile Ala Asp Pro Glu Leu Asn Arg Val Ile
1310                1315                1320

Gln Gly His Lys Val Asn Gly Thr Ala Leu Cys Pro Ser Ser Leu
1325                1330                1335

Tyr Ala Asp Ile Ser Gln Thr Leu Ala Glu Tyr Leu Ile Lys Lys
1340                1345                1350

Tyr Lys Pro Glu Tyr Asp Gly Leu Gly Leu Asp Val Cys Glu Val
1355                1360                1365

Thr Val Pro Arg Pro Leu Ile Ala Lys Gly Gly Gln Gln Leu Phe
1370                1375                1380

Arg Val Ser Ala Thr Ala Asp Trp Ala Glu Lys Lys Thr Thr Leu
1385                1390                1395

Gln Ile Tyr Ser Val Thr Ala Glu Gly Lys Lys Thr Ala Asp His
1400                1405                1410

Ala Thr Cys Thr Val Arg Phe Phe Asp Cys Ala Ala Ala Glu Ala
1415                1420                1425

Glu Trp Lys Arg Val Ser Tyr Leu Val Lys Arg Ser Ile Asp Arg
1430                1435                1440

Leu His Asp Ile Ala Glu Asn Gly Asp Ala His Arg Leu Gly Arg
1445                1450                1455

Gly Met Val Tyr Lys Leu Phe Ala Ala Leu Val Asp Tyr Asp Asp
1460                1465                1470

Asn Phe Lys Ser Ile Arg Glu Val Ile Leu Asp Ser Glu Gln His
1475                1480                1485

Glu Ala Thr Ala Arg Val Lys Phe Gln Ala Pro Gln Gly Asn Phe
1490                1495                1500

His Arg Asn Pro Phe Trp Ile Asp Ser Phe Gly His Leu Ser Gly
1505                1510                1515

Phe Ile Met Asn Ala Ser Asp Ala Thr Asp Ser Lys Asn Gln Val
1520                1525                1530

Phe Val Asn His Gly Trp Asp Ser Met Arg Cys Leu Lys Lys Phe
1535                1540                1545

Ser Pro Asp Val Thr Tyr Arg Thr Tyr Val Arg Met Gln Pro Trp
1550                1555                1560

Lys Asp Ser Ile Trp Ala Gly Asp Val Tyr Val Phe Asp Gly Asp
1565                1570                1575

Asp Ile Val Ala Val Tyr Gly Ala Val Lys Phe Gln Ala Leu Ser
1580                1585                1590

Arg Lys Ile Leu Asp Thr Val Leu Pro Pro Ser Arg Ala Ser Ala
1595                1600                1605

Pro Ala Pro Ala Lys Pro Ala Ala Lys Pro Ser Ala Pro Ser Leu
1610                1615                1620

Val Lys Arg Ala Leu Thr Ile Leu Ala Glu Glu Val Gly Leu Ser
1625                1630                1635

Glu Ser Glu Ile Thr Asp Asp Leu Val Phe Ala Asp Tyr Gly Val
1640                1645                1650

Asp Ser Leu Leu Ser Leu Thr Val Thr Gly Arg Tyr Arg Glu Glu
1655                1660                1665

Leu Asp Ile Asp Leu Glu Ser Ser Ile Phe Ile Asp Gln Pro Thr
1670                1675                1680

Val Lys Asp Phe Lys Gln Phe Leu Ala Pro Met Ser Gln Gly Glu
```

```
            1685                1690                1695

Ala Ser Asp Gly Ser Thr Ser Asp Pro Glu Ser Ser Ser Ser Phe
    1700                1705                1710

Asn Gly Gly Ser Ser Thr Asp Glu Ser Ser Ala Gly Ser Pro Val
    1715                1720                1725

Ser Ser Pro Pro Asn Glu Lys Val Thr Gln Val Glu Gln His Ala
    1730                1735                1740

Thr Ile Lys Glu Ile Arg Ala Ile Leu Ala Asp Glu Ile Gly Val
    1745                1750                1755

Thr Glu Glu Glu Leu Lys Asp Asp Glu Asn Leu Gly Glu Met Gly
    1760                1765                1770

Met Asp Ser Leu Leu Ser Leu Thr Val Leu Gly Arg Ile Arg Glu
    1775                1780                1785

Thr Leu Asp Leu Asp Leu Pro Gly Glu Phe Phe Ile Glu Asn Gln
    1790                1795                1800

Thr Leu Asn Asp Val Glu Asp Ala Leu Gly Leu Lys Pro Lys Ala
    1805                1810                1815

Ala Pro Ala Pro Ala Pro Ala Pro Ala Pro Val Pro Ala Pro Val
    1820                1825                1830

Ser Ala Pro Ile Leu Lys Glu Pro Val Pro Asn Ala Asn Ser Thr
    1835                1840                1845

Ile Met Ala Arg Ala Ser Pro His Pro Arg Ser Thr Ser Ile Leu
    1850                1855                1860

Leu Gln Gly Asn Pro Lys Thr Ala Thr Lys Thr Leu Phe Leu Phe
    1865                1870                1875

Pro Asp Gly Ser Gly Ser Ala Thr Ser Tyr Ala Thr Ile Pro Gly
    1880                1885                1890

Val Ser Pro Asp Val Cys Val Tyr Gly Leu Asn Cys Pro Tyr Met
    1895                1900                1905

Lys Thr Pro Glu Lys Leu Lys Tyr Pro Leu Ala Glu Met Thr Phe
    1910                1915                1920

Pro Tyr Leu Ala Glu Ile Arg Arg Arg Gln Pro Lys Gly Pro Tyr
    1925                1930                1935

Asn Phe Gly Gly Trp Ser Ala Gly Gly Ile Cys Ala Tyr Asp Ala
    1940                1945                1950

Ala Arg Tyr Leu Ile Leu Glu Glu Gly Glu Gln Val Asp Arg Leu
    1955                1960                1965

Leu Leu Leu Asp Ser Pro Phe Pro Ile Gly Leu Glu Lys Leu Pro
    1970                1975                1980

Thr Arg Leu Tyr Gly Phe Ile Asn Ser Met Gly Leu Phe Gly Glu
    1985                1990                1995

Gly Asn Lys Ala Pro Pro Ala Trp Leu Leu Pro His Phe Leu Ala
    2000                2005                2010

Phe Ile Asp Ser Leu Asp Thr Tyr Lys Ala Val Pro Leu Pro Phe
    2015                2020                2025

Asp Asp Pro Lys Trp Ala Lys Lys Met Pro Lys Thr Phe Met Val
    2030                2035                2040

Trp Ala Lys Asp Gly Ile Cys Ser Lys Pro Asp Asp Pro Trp Pro
    2045                2050                2055

Glu Pro Asp Pro Asp Gly Lys Pro Asp Thr Arg Glu Met Val Trp
    2060                2065                2070

Leu Leu Lys Asn Arg Thr Asp Met Gly Pro Asn Lys Trp Asp Thr
    2075                2080                2085
```

| Leu | Val | Gly | Pro | Gln | Asn | Val | Gly | Gly | Ile | Thr | Val | Ile | Glu | Gly |
|---|---|---|---|---|---|---|---|---|---|---|---|---|---|---|
| | 2090 | | | | 2095 | | | | 2100 | | | | | |

| Ala | Asn | His | Phe | Thr | Met | Thr | Leu | Gly | Pro | Lys | Ala | Lys | Glu | Leu |
|---|---|---|---|---|---|---|---|---|---|---|---|---|---|---|
| 2105 | | | | | 2110 | | | | | 2115 | | | | |

| Gly | Ser | Phe | Ile | Gly | Asn | Ala | Met | Ala | Asn |
|---|---|---|---|---|---|---|---|---|---|
| 2120 | | | | | 2125 | | | | |

<210> SEQ ID NO 6
<211> LENGTH: 1725
<212> TYPE: DNA
<213> ORGANISM: Trametes cingulata

<400> SEQUENCE: 6

```
atgcgtttca cgctcctcac ctccctcctg ggcctcgccc tcggcgcgtt cgcgcagtcg      60
agtgcggccg acgcgtacgt cgcgtccgaa tcgcccatcg ccaaggcggg tgtgctcgcc     120
aacatcgggc ccagcggctc aagtccaac ggagcaaagg caggcatcgt gattgcaagt      180
ccgagcacat ccaacccgaa ctacctgtac acatggacgc gcgactcgtc cctcgtgttc     240
aaggcgctca tcgaccagtt caccactggc gaagatacct cgctccgaac tctgattgac     300
gagttcacct cggcggaggc catactccag caggtgccga acccgagcgg acagtcagc     360
actggaggcc tcggcgagcc caagttcaac atcgacgaga ccgcgttcac ggatgcctgg     420
ggtcgtcctc agcgcgatgg tcccgctctc cgggcgactg ccatcatcac ctacgccaac     480
tggctcctcg acaacaagaa cacgacctac gtgaccaaca ctctctggcc tatcatcaag     540
ctcgacctcg actacgtcgc cagcaactgg aaccagtcca cgtttgatct ctgggaggag     600
attaactcct cgtcgttctt cactaccgcc gtccagcacc gtgctctgcg cgagggcgcg     660
actttcgcta tcgcatcgg acaaacctcg gtggtcagcg gtacaccac ccaagcaaac      720
aaccttctct gcttcctgca gtcgtactgg aaccccaccg gcggctatat caccgcaaac     780
acgggcggcg ccgctctgg caaggacgcg aacaccgttc tcacgtcgat ccacaccttc     840
gacccggccg ctggatgcga cgctgttacg ttccagccgt gctcggacaa ggcgctgtcg     900
aacttgaagg tgtacgtcga tgcgttccgc tcgatctact ccatcaacag cgggatcgcc     960
tcgaatgcgg ccgttgctac cggccgctac cccgaggaca gctacatggg cggaaaccca    1020
tggtacctca ccacctccgc cgtcgctgag cagctctacg atgcgctcat tgtgtggaac    1080
aagcttggcg ccctgaacgt cacgagcacc tccctcccct tcttccagca gttctcgtca    1140
ggcgtcaccg tcggcaccta tgcctcatcc tcgtccacct tcaagacgct cacttccgcc    1200
atcaagacct tcgccgacgg cttcctcgcg gtcaacgcca gtacacgcc ctcgaacggc     1260
ggccttgctg aacagtacag ccggagcaac ggctcgcccg tcagcgctgt ggacctgacg    1320
tggagctatg ctgctgccct cacgtcgttt gctgcgcgct caggcaagac gtatgcgagc    1380
tggggcgcgg cgggtttgac tgtcccgacg acttgctcgg ggagtggcgg tgctgggact    1440
gtggccgtca ccttcaacgt gcaggcgacc accgtgttcg gcgagaacat ttacatcaca    1500
ggctcggtcc ccgctctcca gaactggtcg cccgacaacg cgctcatcct ctcagcggcc    1560
aactacccca cttggagcat caccgtgaac ctgccggcga gcacgacgat cgagtacaag    1620
tacattcgca agttcaacgg cgcggtcacc tgggagtccg acccgaacaa ctcgatcacg    1680
acgcccgcga gcggcacgtt cacccagaac gacacctggc ggtag                    1725
```

<210> SEQ ID NO 7
<211> LENGTH: 574

<212> TYPE: PRT
<213> ORGANISM: Trametes cingulata

<400> SEQUENCE: 7

```
Met Arg Phe Thr Leu Leu Thr Ser Leu Leu Gly Leu Ala Leu Gly Ala
1               5                   10                  15

Phe Ala Gln Ser Ser Ala Ala Asp Ala Tyr Val Ala Ser Glu Ser Pro
            20                  25                  30

Ile Ala Lys Ala Gly Val Leu Ala Asn Ile Gly Pro Ser Gly Ser Lys
        35                  40                  45

Ser Asn Gly Ala Lys Ala Gly Ile Val Ile Ala Ser Pro Ser Thr Ser
50                  55                  60

Asn Pro Asn Tyr Leu Tyr Thr Trp Thr Arg Asp Ser Ser Leu Val Phe
65                  70                  75                  80

Lys Ala Leu Ile Asp Gln Phe Thr Thr Gly Glu Asp Thr Ser Leu Arg
                85                  90                  95

Thr Leu Ile Asp Glu Phe Thr Ser Ala Glu Ala Ile Leu Gln Gln Val
            100                 105                 110

Pro Asn Pro Ser Gly Thr Val Ser Thr Gly Gly Leu Gly Glu Pro Lys
        115                 120                 125

Phe Asn Ile Asp Glu Thr Ala Phe Thr Asp Ala Trp Gly Arg Pro Gln
130                 135                 140

Arg Asp Gly Pro Ala Leu Arg Ala Thr Ala Ile Ile Thr Tyr Ala Asn
145                 150                 155                 160

Trp Leu Leu Asp Asn Lys Asn Thr Thr Tyr Val Thr Asn Thr Leu Trp
                165                 170                 175

Pro Ile Ile Lys Leu Asp Leu Asp Tyr Val Ala Ser Asn Trp Asn Gln
            180                 185                 190

Ser Thr Phe Asp Leu Trp Glu Glu Ile Asn Ser Ser Phe Phe Thr
        195                 200                 205

Thr Ala Val Gln His Arg Ala Leu Arg Glu Gly Ala Thr Phe Ala Asn
210                 215                 220

Arg Ile Gly Gln Thr Ser Val Val Ser Gly Tyr Thr Thr Gln Ala Asn
225                 230                 235                 240

Asn Leu Leu Cys Phe Leu Gln Ser Tyr Trp Asn Pro Thr Gly Gly Tyr
                245                 250                 255

Ile Thr Ala Asn Thr Gly Gly Gly Arg Ser Gly Lys Asp Ala Asn Thr
            260                 265                 270

Val Leu Thr Ser Ile His Thr Phe Asp Pro Ala Ala Gly Cys Asp Ala
        275                 280                 285

Val Thr Phe Gln Pro Cys Ser Asp Lys Ala Leu Ser Asn Leu Lys Val
290                 295                 300

Tyr Val Asp Ala Phe Arg Ser Ile Tyr Ser Ile Asn Ser Gly Ile Ala
305                 310                 315                 320

Ser Asn Ala Ala Val Ala Thr Gly Arg Tyr Pro Glu Asp Ser Tyr Met
                325                 330                 335

Gly Gly Asn Pro Trp Tyr Leu Thr Thr Ser Ala Val Ala Glu Gln Leu
            340                 345                 350

Tyr Asp Ala Leu Ile Val Trp Asn Lys Leu Gly Ala Leu Asn Val Thr
        355                 360                 365

Ser Thr Ser Leu Pro Phe Phe Gln Gln Phe Ser Ser Gly Val Thr Val
370                 375                 380

Gly Thr Tyr Ala Ser Ser Ser Ser Thr Phe Lys Thr Leu Thr Ser Ala
385                 390                 395                 400
```

Ile Lys Thr Phe Ala Asp Gly Phe Leu Ala Val Asn Ala Lys Tyr Thr
                405                 410                 415

Pro Ser Asn Gly Gly Leu Ala Glu Gln Tyr Ser Arg Ser Asn Gly Ser
            420                 425                 430

Pro Val Ser Ala Val Asp Leu Thr Trp Ser Tyr Ala Ala Ala Leu Thr
        435                 440                 445

Ser Phe Ala Ala Arg Ser Gly Lys Thr Tyr Ala Ser Trp Gly Ala Ala
450                 455                 460

Gly Leu Thr Val Pro Thr Thr Cys Ser Gly Ser Gly Gly Ala Gly Thr
465                 470                 475                 480

Val Ala Val Thr Phe Asn Val Gln Ala Thr Thr Val Phe Gly Glu Asn
                485                 490                 495

Ile Tyr Ile Thr Gly Ser Val Pro Ala Leu Gln Asn Trp Ser Pro Asp
            500                 505                 510

Asn Ala Leu Ile Leu Ser Ala Ala Asn Tyr Pro Thr Trp Ser Ile Thr
        515                 520                 525

Val Asn Leu Pro Ala Ser Thr Thr Ile Glu Tyr Lys Tyr Ile Arg Lys
530                 535                 540

Phe Asn Gly Ala Val Thr Trp Glu Ser Asp Pro Asn Asn Ser Ile Thr
545                 550                 555                 560

Thr Pro Ala Ser Gly Thr Phe Thr Gln Asn Asp Thr Trp Arg
                565                 570

<210> SEQ ID NO 8
<211> LENGTH: 10703
<212> TYPE: DNA
<213> ORGANISM: Trametes cingulata

<400> SEQUENCE: 8

```
ctagccgtcg gtgtgatgga aatccagcac gttgcaggac caagaatccc cgggtgcggg      60
ggtgggctcg gctgaatggt ctgatcatac tgctagtact agtagttgct gtaaggaacc     120
gtcgggggtg ttattaatag ctggacttgc agatggaaca tgaacatgtc ctgaccattg     180
tatccctcgt gcatgaagcc tgtccctggg agttggtagt agttcatgcc tgagttagta     240
caatgggtat ttgggctagt taccgctgaa tagaagttct cacctgcaag gggaagacca     300
tttgtggttg tcgttgttgt tactgttatt gttattgtta catgagtggg gaagaccaat     360
tgacaatccc gatactttcc aatcccttct cggatttcgt gcaacatcac tgcccatttt     420
gatattatta ttattattat tattatcatc atgattgtat tatggcacga cacgagtgga     480
attcacgtca tcgtctgcca agccagtccc tttccatcca gacctcccga ttaccaagcc     540
cttccgccag tcagcttcgt cctcctcctc atcgccaagc ctgcccttcg gcgggtcat     600
ggaccccccg gccaatgagc aacgcgccat tggccgtgtg tctgcatctc gatacgcatc     660
ccaggattcc ttaccgaaag atatcatccc aagtaaggta cacgcctggt atcgaacaaa     720
acatgctggg acggacggct cctacattcg ttactagtca tacaatctag tcaattagta     780
gctgctgcca atgccaatgc caatgccaat gcctctctat ataattccct cagttccccc     840
ctctcttctc tcctcctccc ctccccttcc ttctcctctc actgctccaa ttgcctcatc     900
ttccctggac gtagtccaac ttcccccctt cccttcggat ccaccatgcg tttcacgctc     960
ctcacctccc tcctgggcct cgccctcggc gcgttcgcgc agtcgagtgc ggccgacgcg    1020
tacgtcgcgt ccgaatcgcc catcgccaag gcgggtgtgc tcgccaacat cgggcccagc    1080
ggctccaagt ccaacggagc aaaggcaggc atcgtgattg caagtccgag cacatccaac    1140
```

```
ccgaactacc tgtacacatg gacgcgcgac tcgtccctcg tgttcaaggc gctcatcgac    1200
cagttcacca ctggcgaaga tacctcgctc cgaactctga ttgacgagtt cacctcggcg    1260
gaggccatac tccagcaggt gccgaacccg agcgggacag tcagcactgg aggcctcggc    1320
gagcccaagt tcaacatcga cgagaccgcg ttcacggatg cctggggtcg tcctcagcgc    1380
gatggtcccg ctctccgggc gactgccatc atcacctacg ccaactggct cctcgacaac    1440
aagaacacga cctacgtgac caacactctc tggcctatca tcaagctcga cctcgactac    1500
gtcgccagca actggaacca gtccacgttt gatctctggg aggagattaa ctcctcgtcg    1560
ttcttcacta ccgccgtcca gcaccgtgct ctgcgcgagg gcgcgacttt cgctaatcgc    1620
atcggacaaa cctcggtggt cagcgggtac accacccaag caaacaacct tctctgcttc    1680
ctgcagtcgt actggaaccc caccggcggc tatatcaccg caaacacggg cggcggccgc    1740
tctggcaagg acgcgaacac cgttctcacg tcgatccaca ccttcgaccc ggccgctgga    1800
tgcgacgctg ttacgttcca gccgtgctcg gacaaggcgc tgtcgaactt gaaggtgtac    1860
gtcgatgcgt tccgctcgat ctactccatc aacagcggga tcgcctcgaa tgcggccgtt    1920
gctaccggcc gctaccccga ggacagctac atgggcggaa acccatggta cctcaccacc    1980
tccgccgtcg ctgagcagct ctacgatgcg ctcattgtgt ggaacaagct tggcgccctg    2040
aacgtcacga gcacctccct ccccttcttc cagcagttct cgtcaggcgt caccgtcggc    2100
acctatgcct catcctcgtc caccttcaag acgctcactt ccgccatcaa gaccttcgcc    2160
gacggcttcc tcgcggtcaa cgccaagtac acgccctcga acggcggcct tgctgaacag    2220
tacagccgga gcaacggctc gcccgtcagc gctgtggacc tgacgtggag ctatgctgct    2280
gccctcacgt cgtttgctgc gcgctcaggc aagacgtatg cgagctgggg cgcggcgggt    2340
ttgactgtcc cgacgacttg ctcggggagt ggcggtgctg ggactgtggc cgtcaccttc    2400
aacgtgcagg cgaccaccgt gttcggcgag aacatttaca tcacaggctc ggtccccgct    2460
ctccagaact ggtcgcccga caacgcgctc atcctctcag cggccaacta ccccacttgg    2520
agcatcaccg tgaacctgcc ggcgagcacg acgatcgagt acaagtacat tcgcaagttc    2580
aacggcgcgg tcacctggga gtccgacccg aacaactcga tcacgacgcc cgcgagcggc    2640
acgttcaccc agaacgacac ctggcggtag ctcgagaggg tgactgacac ctggcggtag    2700
acaatcaatc catttcgcta tagttaaagg atggggatga gggcaattgg ttatatgatc    2760
atgtatgtag tgggtgtgca taatagtagt gaaatggaag ccaagtcatg tgattgtaat    2820
cgaccgacgg aattgaggat atccggaaat acagacaccg tgaaagccat ggtctttcct    2880
tcgtgtagaa gaccagacag acagtccctg atttacccTt gcacaaagca ctagaaaatt    2940
agcattccat ccttctctgc ttgctctgct gatatcactg tcattcaatg catagccatg    3000
agctcatctt agatccaagc acgtaattcc atagccgagg tccacagtgg agcagcaaca    3060
ttccccatca ttgctttccc caggggcctc ccaacgacta aatcaagagt atatctctac    3120
cgtccaatag atcgtcttcg cttcaaaatc tttgacaatt ccaagagggt ccccatccat    3180
caaacccagt tcaataatag ccgagatgca tggtggagtc aattaggcag tattgctgga    3240
atgtcggggc cagttggccc ggtggtcatt ggccgcctgt gatgccatct gccactaaat    3300
ccgatcattg atccaccgcc cacgaggcgc gtctttgctt tttgcgcggc gtccaggttc    3360
aactctctcg cactagcaaa gtattttcgg tacgattttg acatttgctc cattgtcgag    3420
gatggatgga acgagcggcg tgcgccacga aagtgaggct attgcctatc agctctttgc    3480
```

```
tacattccgg aaacaaacat cccttttgt gaattatcta cgcaacttag atggcgtgaa    3540
cgcatcttca aagtctttcg gcaggtccgg cacgactttt gcatccagag aagcgcctac    3600
atgtgtattc gaccacctcc tagcgcgctt ggatatgagg aaatattact gagagtcgaa    3660
aacaagctcc accgcaccag ctcttcttgg agttttatat taaagaatat tcccagctcg    3720
ttgtattatt cttttctac cgtgctaatg tatcaaggac tttggtacct attaacgtta    3780
ttattcgtgt gctattccca aacataaccc tgtatatgtt tcgaacgccg ttatgaccca    3840
tgtcttacat actcattaag tcattccctt ggataatctc gactcagatg cggcggttga    3900
tgtaggagga gaggtaatcg aggacctcct gggagatgat gccgttccag gcggggtagc    3960
ggatggagcc ctcggcggag cccttgagct gctcgatatg ctgccactcc tcgatggggt    4020
tggtctcatc cttgagggcg atcatctcct tggagatggg atcgtaggcg tagtagcggg    4080
agactagtgc gaagtaatga tcggggatgg cggtgatctg atggggtgtag gtggtgcggg    4140 cgacggcgga ggcgcgctta tcggaccagt tgccgacgac gttggtgagc tcggtgaggc    4200
ccttcatgga gaggaaggag gtcatgagat ggcggccgat atgggacttg gggccgttct    4260
tgatggcgaa gatggagtag ggggcgttct tcttgagggc cttgttgtag gagcggacga    4320
ggttatcctt gaggagctgg tactcctgct tgttggagga ggagttgccg gtgcggttga    4380
cgcgcttgag gacgggctcg gagttgcgga ggaactcatc gaggtagacg aggggatcga    4440
tgcggccgcg ggcggagaag aagtagatat ggcgggagac ggaggtcttg gtctcggtga    4500
cgaggcactg gatgatgacg ccgaggtact tgttctggac gagcttgaag gacttgggat    4560
cgacgttctt gatatcggag aagcggccgc agttgatgaa ggtggcgagg aagaggaact    4620
ggtagagggt cttggtcttg gtgaagcggg aggtgtactc gaaggagttg aggatcttct    4680
cggtgatctc ccagatggac tcgccctcgg agaggagggc cttgagcatc ttcttggaat    4740
gggagttgcc cttatcggcc tcctcggagg actcgaactg gagctggagg gaggagacga    4800
tatcggtgat atcggactga tgcttctggc cgtagtaggg gatgatggtg aactcccagg    4860
cggggatgag cttcttgagg gaggcctcca ggatggtggc cttctgggtc ttgtacttga    4920
actggaggga cttgttgacg atatcgaagg agagggagtt ggagatgatg tgttgtagg    4980 acatgaaggt ggcgcgcttg atggcggtgc cgttatgggt gatcatccag cagaggtagg    5040
tgagctcggc ggcgcagagg gcgatcttct cgccggaggg gcgctcgaag cgctcgacga    5100
actggcggac gaggaccttg ggggggtct tgcagaggat atcgaactgg ggcatggtgg    5160
atcgatcccc tgtcagttgg gttgttggaa tctgggagcc ggacagaaag gaatgctacc    5220
tcctttatag gtagtgtccg gttaatagcc tctggatcag aagtacaacg tctccccgtg    5280
agagggcaat cagcctgttt ccggctcttt tggttataaa ctcctgaata gccattcgtt    5340
ttcccagata gcgtagcagc aactgcaagc tgtgcatgtg ctagagccca tgcgggcaaa    5400
gaaaaacccc agactaaacc cagtggaccc cgatccgctc cacaaaccga attgctgaat    5460
agcctgaatg aagaatctct gcagaattct attgctcctt gttccagtgg aaacggcgc    5520 cgcttggcac gcttaagtat catggttcag ctccgtttca aatagaggca gctccggcga    5580
ctgttctaga cccgtgggcc aagacgagtc catctgtctg taatgctatc ggaagctatt    5640
ggatggcccc tgagcatcag gtagatgagg tttccggctc tcaatcagag tttagggcaa    5700
tcggccggta cacgttcaat gagaactcca gctaggcat agatgtccta ccatagccac    5760
cgctagacca cttactgggt actacatttt cggggaataa tgatcaacgc acttccatta    5820
attaacctag tactaaatga cgtttgtgaa cagcccaaag cctacaaatt caactgcgca    5880
```

```
caacgcgccc acggcaactt cctcgagaac gcgccgcaga caatgctctc tatcctggtg    5940
gcaggcgtca agtacccaga ggcagcagcg ggcttaggag cggcctgggt tgttctccgc    6000
accctctaca tgctgggcta tatttatagc gacaagccga acggcaccgg caggtacaat    6060
ggttcgctgt acttgcttgc gcaagcgggt ctttggggat tgagcgcatt tggtgttgca    6120
aaggatttga tgtaaatgta gtcgacatct tagcacagag gggagagttg ataaaatgtg    6180
gtctgtttga atgatagtcg ggttcgtgac ctatattcgt gatagtggag ataggtctgc    6240
gcctatctta tcgggccgga gcaaaaattc caccgcagcg gggtgagttt cgttataca    6300 gccatcccac ttccagcttc aaattgtcag tttaatccag cccaattcaa tcattggaga    6360
accgccatca tgtcttcgaa gtcccacctc ccctacgcaa ttcgcgcaac caaccatccc    6420 aacccttaa catctaaact cttctccatc gccgaggaga agaaaaccaa cgtcaccgtc    6480
tccgcagacg ttactacttc cgccgagctc ctcgatcttg ctgaccgcct aggcccctat    6540
atcgcagttc tgaaaaccca catcgacatc ctcaccgatc tcaccccgtc gaccttcc    6600 tcgctccaat ccctcgcgac aaagcacaac ttcctcatct ttgaggaccg caagttcatc    6660
gacatcggca acaccgtgca aaagcagtac acggtggcg ctctccgcat ctccgaatgg    6720
gcacacatca tcaactgcgc catcctgccg ggcgaaggga tcgtcgaggc cctcgcacag    6780
acaaccaagt ctcctgactt taaagacgcg aatcaacgag gtctcctgat tcttgccgag    6840
atgacgagta agggatctct tgcgacaggg gagtacacgg cacgctcggt tgagtacgcg    6900
cggaagtata aggggtttgt gatgggattc gtgagtacaa gggcgttgag tgaggtgctg    6960
cccgaacaga aagaggagag cgaggatttt gtcgtctta cgactggggt gaatctgtcg    7020
gataaggggg ataagctggg gcagcagtat cagacacctg ggtcggcggt tgggcgaggt    7080
gcggacttta tcattgcggg taggggcatc tataaggcgg acgatccagt cgaggcggtt    7140
cagaggtacc gggaggaagg ctggaaagct tacgagaaaa gagttggact ttgagggtga    7200
ctgacacctg gcggtagaca atcaatccat ttcgctatag ttaaaggatg gggatgaggg    7260
caattggtta tatgatcatg tatgtagtgg gtgtgcataa tagtagtgaa atggaagcca    7320
agtcatgtga ttgtaatcga ccgacggaat tgaggatatc cggaaataca gacaccgtga    7380
aagccatggt cttccttcg tgtagaagac cagacagaca gtccctgatt tacccttgca    7440
caaagcacta gaaaattagc attccatcct tctctgcttg ctctgctgat atcactgtca    7500
ttcaatgcat agccatgagc tcatcttaga tccaagcacg taattccata gccgaggtcc    7560
acagtggagc agcaacattc cccatcattg ctttccccag gggcctccca acgactaaat    7620
caagagtata tctctaccgt ccaatagatc gtcttcgctt caaaatcttt gacaattcca    7680
agagggtccc catccatcaa acccagttca ataatagccg agatgcatgg tggagtcaat    7740
taggcagtat tgctggaatg tcggggccag ttggccgggt ggtcattggc cgcctgtgat    7800
gccatctgcc actaaatccg atcattgatc caccgcccac gaggcgcgtc tttgcttttt    7860
gcgcggcgtc caggttcaac tctctcctct aggttgaagt tcctattccg agttcctatt    7920
cttcaaatag tataggaact tcaactagct agtgcatgca agcttggcct ccgcggcctg    7980
cggccgcagc ttggcgtaat catggtcata gctgtttcct gtgtgaaatt gttatccgct    8040
cacaattcca cacaacatac gagccggaag cataaagtgt aaagcctggg gtgcctaatg    8100
agtgagctaa ctcacattaa ttgcgttgcg ctcactgccc gctttccagt cgggaaacct    8160
gtcgtgccag ctgcattaat gaatcggcca acgcgcgggg agaggcggtt tgcgtattgg    8220
```

```
gcgctcttcc gcttcctcgc tcactgactc gctgcgctcg gtcgttcggc tgcggcgagc    8280
ggtatcagct cactcaaagg cggtaatacg gttatccaca gaatcagggg ataacgcagg    8340
aaagaacatg tgagcaaaag gccagcaaaa ggccaggaac cgtaaaaagg ccgcgttgct    8400
ggcgtttttc cataggctcc gcccccctga cgagcatcac aaaaatcgac gctcaagtca    8460
gaggtggcga acccgacag gactataaag ataccaggcg tttccccctg gaagctccct    8520
cgtgcgctct cctgttccga ccctgccgct taccggatac ctgtccgcct ttctcccttc    8580
gggaagcgtg gcgctttctc atagctcacg ctgtaggtat ctcagttcgg tgtaggtcgt    8640
tcgctccaag ctgggctgtg tgcacgaacc ccccgttcag cccgaccgct gcgccttatc    8700
cggtaactat cgtcttgagt ccaacccggt aagacacgac ttatcgccac tggcagcagc    8760
cactggtaac aggattagca gagcgaggta tgtaggcggt gctacagagt tcttgaagtg    8820
gtggcctaac tacggctaca ctagaaggac agtatttggt atctgcgctc tgctgaagcc    8880
agttaccttc ggaaaaagag ttggtagctc ttgatccggc aaacaaacca ccgctggtag    8940
cggtggtttt tttgtttgca agcagcagat tacgcgcaga aaaaaaggat ctcaagaaga    9000
tcctttgatc ttttctacgg ggtctgacgc tcagtggaac gaaaactcac gttaagggat    9060
tttggtcatg agattatcaa aaaggatctt cacctagatc cttttaaatt aaaaatgaag    9120
ttttaaatca atctaaagta tatatgagta aacttggtct gacagttacc aatgcttaat    9180
cagtgaggca cctatctcag cgatctgtct atttcgttca tccatagttg cctgactccc    9240
cgtcgtgtag ataactacga tacgggaggg cttaccatct ggccccagtg ctgcaatgat    9300
accgcgagac ccacgctcac cggctccaga tttatcagca ataaaccagc cagccggaag    9360
ggccgagcgc agaagtggtc ctgcaacttt atccgcctcc atccagtcta ttaattgttg    9420
ccgggaagct agagtaagta gttcgccagt taatagtttg cgcaacgttg ttgccattgc    9480
tacaggcatc gtggtgtcac gctcgtcgtt tggtatggct tcattcagct ccggttccca    9540
acgatcaagg cgagttacat gatcccccat gttgtgcaaa aaagcggtta gctccttcgg    9600
tcctccgatc gttgtcagaa gtaagttggc cgcagtgtta tcactcatgg ttatggcagc    9660
actgcataat tctcttactg tcatgccatc cgtaagatgc ttttctgtga ctggtgagta    9720
ctcaaccaag tcattctgag aatagtgtat gcggcgaccg agttgctctt gcccggcgtc    9780
aatacgggat aataccgcgc cacatagcag aactttaaaa gtgctcatca ttggaaaacg    9840
ttcttcgggg cgaaaactct caaggatctt accgctgttg agatccagtt cgatgtaacc    9900
cactcgtgca cccaactgat cttcagcatc ttttactttc accagcgttt ctgggtgagc    9960
aaaaacagga aggcaaaatg ccgcaaaaaa gggaataagg gcgacacgga aatgttgaat   10020
actcatactc ttcctttttc aatattattg aagcatttat cagggttatt gtctcatgag   10080
cggatacata tttgaatgta tttagaaaaa taaacaaata ggggttccgc gcacatttcc   10140
ccgaaaagtg ccacctgacg tctaagaaac cattattatc atgacattaa cctataaaaa   10200
taggcgtatc acgaggccct ttcgtctcgc gcgtttcggt gatgacggtg aaaacctctg   10260
acacatgcag ctcccggaga cggtcacagc ttgtctgtaa gcggatgccg ggagcagaca   10320
agcccgtcag ggcgcgtcag cgggtgttgg cgggtgtcgg gctggctta actatgcggc   10380
atcagagcag attgtactga gagtgcacca tatgcggtgt gaaataccgc acagatgcgt   10440
aaggagaaaa taccgcatca ggcgccattc gccattcagg ctgcgcaact gttgggaagg   10500
gcgatcggtg cgggcctctt cgctattacg ccagctggcg aaaggggggat gtgctgcaag   10560
gcgattaagt tgggtaacgc cagggttttc ccagtcacga cgttgtaaaa cgacggccag   10620
```

| | |
|---|---:|
| tttggcctcc atggccgcgg ccgcgaattc atcttgaagt tcctattccg agttcctatt | 10680 |
| ctctagaaag tataggaact tcg | 10703 |

<210> SEQ ID NO 9
<211> LENGTH: 35
<212> TYPE: DNA
<213> ORGANISM: Artificial Sequence
<220> FEATURE:
<223> OTHER INFORMATION: ARTIFICIAL DNA PRIMER

<400> SEQUENCE: 9

| | |
|---|---:|
| gaaccttacg cggccatgcg tttcacgctc ctcac | 35 |

<210> SEQ ID NO 10
<211> LENGTH: 36
<212> TYPE: DNA
<213> ORGANISM: Artificial Sequence
<220> FEATURE:
<223> OTHER INFORMATION: ARTIFICIAL DNA PRIMER

<400> SEQUENCE: 10

| | |
|---|---:|
| gaacatcgcg cggccgcttc gggttggatg tgctcg | 36 |

<210> SEQ ID NO 11
<211> LENGTH: 6426
<212> TYPE: DNA
<213> ORGANISM: Aspergillus oryzae

<400> SEQUENCE: 11

| | |
|---|---:|
| atggagggggc cacgcggcgt ctatctcttc ggagaccaga caagtgattt cgacgccggc | 60 |
| ttacgtcgcc tcctacaagt aaagaataac acaattgttg catcgttctt ccagagatgc | 120 |
| tttcacgctt tgcgccaaga gatcgcgagg cttttcaccat ctgaacggaa gatcttcccc | 180 |
| cggtttacga gcatagtgga tctactggcg cgtcaccggg agtcagaccc taatccggct | 240 |
| ctggagagtg cgttgacctg tatctatcaa ttgggatgct ttataaacta ctacggagac | 300 |
| cttgaaaacg tgtacccatc tgcttcagac tgccatatag ttggcctgtg cgcgggtctt | 360 |
| cttagttctg cagctgtaag ctgttcgaac aatgttggag aattgctccc cgctgcggtt | 420 |
| gaagcggtgg tggtagctct ccgacttggt ctatgcgtcc ttaaagttcg agagctggtg | 480 |
| agctctgacc aagcgtcgtc aacaagctgg tcagtcttga tttcagggat tagcgagaaa | 540 |
| gatgcctcgc agcttatagg agaattcact gctgaacggg caattcctcc ttcatccaaa | 600 |
| ccgtatatca gtgcggtggg atataacagt ataaccatca gcgcaccgcc taaggtcctt | 660 |
| gatgatttaa ttgattctag gctgtctaag agccataagc cggtgagggc gcaaatccat | 720 |
| ggtccttacc atgcagcaca tctgtactat ggccgagatg tcgacaggat catcgaaagc | 780 |
| tgccataatg aggtcgtttc aaactacaca ccccgtatcc ccgtactatc aagtactacg | 840 |
| ggacagccga tagaggccaa acacatgaaa gatctactta aggccgccct tgaagagatt | 900 |
| ctactacgtc aactatgctg ggagaaagtg accgatgcct gctattccat attaaaaact | 960 |
| gctcgtcatc aaccatgcaa gttgttccca atttcaagca ctgcgacaca aagcttgttt | 1020 |
| acagctctta cgaaagccgg gataaccgac atcgaagtgg aaaatgggct cggagatgtt | 1080 |
| cccacgaacc cgaaggacaa ccttaacatc agcggcaggg cggactgctc caagatagct | 1140 |
| atcattggca tgtctggacg attcccagaa gctgatggca cagagagttt ctggaccctt | 1200 |
| ctgtataatg gcctcgatgt acaccggaag gtgcctgcag agcgttggga tgttgatgcc | 1260 |

```
cacgttgatc ctaccggaac aaaacggaac accagcaagg ttccatacgg atgctggata    1320
aacgaaccgg ggttatttga cccccgcttc ttcaatatgt cgccacgcga agccctccag    1380
gcagatcccg ctcaaagact tgcattgctc acggcctatg aagctcttga aatggccggc    1440
tttatccccg acagcacccc ttctacacag agggatcgag tcggcctctt ctatggaatg    1500
actagcgatg actatcggga gataaatagt ggtcaagata ttgatactta ctttatccct    1560
ggtgggaatc gtgctttcac acctggccgg ataaactact atttcaagtt cagtgggccc    1620
agcgtcagcg ttgatacagc ttgttcttca agtcttgcgg ctattcatat ggcttgcaat    1680
tcgatctgga gaaatgattg cgatgctgct attgctggag gtgtcaatat attgacaaac    1740
cctgataacc atgccggtct tgaccgtggc catttcctgt ccagaaccgg gaattgcaac    1800
acatttgacg atggtgctga tggctactgt agagcagatg gagtgggtac aatcattctc    1860
aagcggctgg aagacgctca ggcggacaac gatccaatcc tcggtgtgat caatggagcc    1920
tataccaatc attcggcaga agcagtctcg attacccgcc tcatgttggc gcacaagcg     1980 tttatcttta ataagctatt gaacgatgcc aatatcgacc ctaaggacgt cagctacgtt    2040
gaaatgcatg gaactggtac tcaagctggg gatgcgtggg aaatgcaatc ggtcttggat    2100
acgtttgctc ccgactaccg ccgtggacca ggacagtctc tccatcttgg ttccgccaaa    2160
gcaaatgttg ggcatggaga gtcagcatct ggtgtaactg cacttgtgaa agtgctgcta    2220
atgatgaaga agaataccat accccctcat tgtggtataa agactaagat caaccacaac    2280
ttccccacgg atctcgcgca acgaaatgtc cacattgcct ttcaacctac cccttggaac    2340
agaccggctt ccggaaagcg gcagtgcttc attaacaact tttcggcggc tggtggaaat    2400
accgctcttt tgatggaaga cgctccaatc gctgaggtta aggggcagga cactcgacct    2460
gttcacgttg tgtctgtatc ggcacgatcc cagagtgcgc tcaaaaacaa catcaactct    2520
ctcgtaaaat acatcgacga acaaggaagg tcattcaatg tgaacgaggc agactttatc    2580
ccaagcttgg catacaccac cacagcacgg cgtatccatc acccattccg tgtcacagct    2640
atcgggtcta gtttgcagga gctgcgtgac tcacttaaca acagctctcg tctggaaagc    2700 tttaccctg tccctgcgac ggcccctggc gtagggttcg tgttcgctgg ccaaggagct    2760
cagcacaccg gaatgggaag gcaactatac gaaaaatgct ctcaattccg ggcaacaatg    2820
cagcacttcg attgcattag tcaaaaccaa gggtttcctt cgatccttcc cttggttgac    2880
ggaagcgtgc ccgtggagga gctgggccct atcgtgacac agctcggcac cacatgtctt    2940
cagatggctt tggtcaacta ttggggttca ctaggtataa aacctgcgtt cgttcttggg    3000
catagtctcg gggagtttgc tgctttgaat accgcaggag tattatcgac ttccgatacc    3060
atctaccttt gtggccgtcg ggctaccctc cttacagaat actgccaggt tgggacacac    3120
gccatgctgg ctgtcaaggc ttcctacccc caggtcaagc agttactgaa agaaggtgtg    3180
gatgaagttg cctgtgtcaa ctcacccagt gagacagtcg tcagtggcct caccgctgat    3240
attgatgact ggctcaaaag gtgttccact gaaggttgga agtccactaa actaagggta    3300
ccgttcgctt ccattctgc ccaagttact ccaattcttg aacggtttca agaagaggcc    3360
cagggtgtca cgttccgtaa gccgtcgtta ccgtttgttt cctcactcct tggggaagtc    3420
atcaccgaat ctaattacga tgtcctggga gctcaatata tggtgaagca gtgccggaag    3480
tcggtgaact tccttggtgc tcttgaggcc accagatatg cgaaattgat gactgataag    3540
actgtctggc tggaagttgg tgcccatacc atttgctctg gtatgatcaa agcaacattc    3600
ggtccccagg ttaccactgt ggcatctctt cgccgagagg agaatgcatg gaaggtcctc    3660
```

```
tccaatagtc tatcggccct tcatttggct ggcattgata ttaattggaa agaatatcat    3720
caagacttca gctccagcca ccaggtgctc ccacttcctt cttacaagtg ggatctcaag    3780
aactactgga tacccTacac taacaatttc tgccttacga agggtgctcc ccaaactgca    3840
attcaagctg caccacaaac tacattcctg accactgctg cgcaaaaggt tgttgagagt    3900
cgcgacgacg gtacaacagc gactgtcgtg gtgcaaaatg acatcgctga tcctgagttg    3960
aaccgtgtta tccaaggtca caaggtcaat ggagccgcac tttgcccatc gtcactctac    4020
gcagatattg cccagacact tggagagtat cttattgaga aatacaaacc cgagttcaaa    4080
gatcttggtc tcgatgtgtg tgacatggtc gtaccgaagc cactcatcgc gaagggagga    4140
gagcagctct ttagagtctc tgctattgct aattgggctg agaagaaggc ttcagttcaa    4200
gtatacgccg ttaatgctga cggcaaaaag accgtggatc atgcgtattg tacggtgaag    4260
ttctttgata ccaatgcctc cgagctcgag tggaagagaa tctcgtacct ggtcaagaga    4320
agcatcgaca gtcttcacca gaatgcggag acagggagg ctcaccgtat ccagcgagga    4380
atggtctata aacttttcag cgcgttggtc gattatgatg aaaatttcaa gtcgattcgc    4440
gaggttatcc tggacagcga caataatgag gccaccgctc gtgtcaaatt ccaagcaccg    4500
ccaggaaatt tccaccgaaa cccattctgg attgacagtt tcggtcactt gtccggattc    4560
attatgaatg cgagcgacgc gaccgactct aagaaccaag tatttgttaa ccatggatgg    4620
gattcgatgc gttgcctgaa gaagttctcg cctgatgtca cttatcgcac ttatgtgagg    4680
atgcagccat ggcaaaacaa catttgggct ggagatgttt atatctttga gggcgacgat    4740
attattgctg tcttcggagg tgtgaagttc caagcactgg cacgcaagat acttgacact    4800
gttcttcccc ctgttggcgg ttcaaaggca ccaattacag cgaaatcacc acctccagct    4860
cgcactcaga aggccaacac cggcgccaag acccgtccta agcacctgt tccttccaag    4920
tcgttcacca aatcttctgg gccgagtgtt gtcgtacgcg cactcagcat tctggcctca    4980
gaagttggcc tggcagagtc tgaaatctca gacgacatgg tgtttgcgga ctacggtgta    5040
gactcactcc tctcccttac agttactggc aggtatcgtg aagagttgaa cctcgatttg    5100
gactcctctg tgtttaccga tcatccaact gtcaacgact tcaagcggct catcgcccaa    5160
gtgagtcctt cagagagcca tgatggttcc tccagtgaac aagagtcgaa tttctctttc    5220
aacggtggcg agtcctcaag cgcaagcaca cctgacataa cgtcaccgcc gaatgagaag    5280
gtagctcaag tcgagcaaaa cggcaccatg aaggaaatcc gtaacatcat ggcggaggag    5340
atcggtgtac ccgcagaaga gatcgaccct gacgagaact tggagagat gggtatggac    5400
tcgcttctct cccttactgt tcttggaaga atacgggaga cttTggacat ggacctgcca    5460
ggagagttct tcatcgaaaa ccagaccctc aatgatatag aggtggcttt ggacctaaaa    5520
cccaagacta cctctgctcc aattcctatg ccagagccag tgaaattccc tgaagctatc    5580
cacgacctcc agccaaagct tgctcaacat cccaaggcca catccatcct gttacaagga    5640
aaccccagga cagcaacaaa gacgttattc ttgtttcctg acggctctgg ctcagctaca    5700
tcttacgcta ccatccccgg actctctcct gacgtctgcg tttacgggtt gaattgccca    5760
tatatgaaga cacctgagaa gctcaaatgc agcctagatg aactcactgc gccctatgta    5820
gcagagattc gtcgtcggca acccaagggt ccttacagct tcggtggctg gtcagcagga    5880
gggatctgtg catatgatgc ggcacgccat ctaatgtttg aggaaggtga acaagtcgac    5940
cgcttgcttc tccttgatac ccccttcccc atcggcctcg agaagctgcc gcagagattg    6000
```

-continued

```
tacggcttct tcaactctat cggtctcttc ggtgaaggta aaacggcacc accctcctgg    6060
ctcctacccc acttcctagc ctttatcgac gctctcgacg catacaaggc cgcgcccctt    6120
ccattcaaag acgagaaatg ggccaagaaa ctgcccaaga cttatatcat ctgggccaag    6180
gacggtgttt gcggtaagcc gggagatccc cggcctgatc ccccgacaga cggttccaag    6240
gatcccaagg agatggtctg gcttcttaat gaccggaccg atctgggacc taacaagtgg    6300
gatacattgg ttggacctga gaatattggt ggaatcacag taatgaagaa tgctaatcat    6360
tttacgatga cgaagggcga aaaagcgaaa gagttgtcta catttatggc taacgccatg    6420
gcttaa                                                               6426
```

<210> SEQ ID NO 12
<211> LENGTH: 2141
<212> TYPE: PRT
<213> ORGANISM: Aspergillus oryzae

<400> SEQUENCE: 12

| Met | Glu | Gly | Pro | Arg | Gly | Val | Tyr | Leu | Phe | Gly | Asp | Gln | Thr | Ser | Asp |
|---|---|---|---|---|---|---|---|---|---|---|---|---|---|---|---|
| 1 | | | | 5 | | | | | 10 | | | | | 15 | |

| Phe | Asp | Ala | Gly | Leu | Arg | Arg | Leu | Leu | Gln | Val | Lys | Asn | Asn | Thr | Ile |
| | | | 20 | | | | | 25 | | | | | 30 | | |

| Val | Ala | Ser | Phe | Phe | Gln | Arg | Cys | Phe | His | Ala | Leu | Arg | Gln | Glu | Ile |
| | | 35 | | | | | 40 | | | | | 45 | | | |

| Ala | Arg | Leu | Ser | Pro | Ser | Glu | Arg | Lys | Ile | Phe | Pro | Arg | Phe | Thr | Ser |
| | 50 | | | | | 55 | | | | | 60 | | | | |

| Ile | Val | Asp | Leu | Leu | Ala | Arg | His | Arg | Glu | Ser | Asp | Pro | Asn | Pro | Ala |
| 65 | | | | | 70 | | | | | 75 | | | | | 80 |

| Leu | Glu | Ser | Ala | Leu | Thr | Cys | Ile | Tyr | Gln | Leu | Gly | Cys | Phe | Ile | Asn |
| | | | | 85 | | | | | 90 | | | | | 95 | |

| Tyr | Tyr | Gly | Asp | Leu | Gly | Asn | Val | Tyr | Pro | Ser | Ala | Ser | Asp | Cys | His |
| | | | 100 | | | | | 105 | | | | | 110 | | |

| Ile | Val | Gly | Leu | Cys | Ala | Gly | Leu | Leu | Ser | Ser | Ala | Val | Ser | Cys |
| | | 115 | | | | | 120 | | | | | 125 | | |

| Ser | Asn | Asn | Val | Gly | Glu | Leu | Leu | Pro | Ala | Ala | Val | Glu | Ala | Val | Val |
| | 130 | | | | | 135 | | | | | 140 | | | | |

| Val | Ala | Leu | Arg | Leu | Gly | Leu | Cys | Val | Leu | Lys | Val | Arg | Glu | Leu | Val |
| 145 | | | | | 150 | | | | | 155 | | | | | 160 |

| Ser | Ser | Asp | Gln | Ala | Ser | Ser | Thr | Ser | Trp | Ser | Val | Leu | Ile | Ser | Gly |
| | | | | 165 | | | | | 170 | | | | | 175 | |

| Ile | Ser | Glu | Lys | Asp | Ala | Ser | Gln | Leu | Ile | Gly | Glu | Phe | Thr | Ala | Glu |
| | | | 180 | | | | | 185 | | | | | 190 | | |

| Arg | Ala | Ile | Pro | Pro | Ser | Ser | Lys | Pro | Tyr | Ile | Ser | Ala | Val | Gly | Tyr |
| | | 195 | | | | | 200 | | | | | 205 | | | |

| Asn | Ser | Ile | Thr | Ile | Ser | Ala | Pro | Pro | Lys | Val | Leu | Asp | Asp | Leu | Ile |
| | 210 | | | | | 215 | | | | | 220 | | | | |

| Asp | Ser | Arg | Leu | Ser | Lys | Ser | His | Lys | Pro | Val | Arg | Ala | Gln | Ile | His |
| 225 | | | | | 230 | | | | | 235 | | | | | 240 |

| Gly | Pro | Tyr | His | Ala | Ala | His | Leu | Tyr | Tyr | Gly | Arg | Asp | Val | Asp | Arg |
| | | | | 245 | | | | | 250 | | | | | 255 | |

| Ile | Ile | Glu | Ser | Cys | His | Asn | Glu | Val | Val | Ser | Asn | Tyr | Thr | Pro | Arg |
| | | | 260 | | | | | 265 | | | | | 270 | | |

| Ile | Pro | Val | Leu | Ser | Ser | Thr | Thr | Gly | Gln | Pro | Ile | Glu | Ala | Lys | His |
| | | 275 | | | | | 280 | | | | | 285 | | | |

| Met | Lys | Asp | Leu | Leu | Lys | Ala | Ala | Leu | Glu | Glu | Ile | Leu | Leu | Arg | Gln |

```
                290                 295                 300
Leu Cys Trp Glu Lys Val Thr Asp Ala Cys Tyr Ser Ile Leu Lys Thr
305                 310                 315                 320

Ala Arg His Gln Pro Cys Lys Leu Phe Pro Ile Ser Ser Thr Ala Thr
                325                 330                 335

Gln Ser Leu Phe Thr Ala Leu Thr Lys Ala Gly Ile Thr Asp Ile Glu
                340                 345                 350

Val Glu Asn Gly Leu Gly Asp Val Pro Thr Asn Pro Lys Asp Asn Leu
                355                 360                 365

Asn Ile Ser Gly Arg Ala Asp Cys Ser Lys Ile Ala Ile Gly Met
                370                 375                 380

Ser Gly Arg Phe Pro Glu Ala Asp Gly Thr Glu Ser Phe Trp Asp Leu
385                 390                 395                 400

Leu Tyr Asn Gly Leu Asp Val His Arg Lys Val Pro Ala Glu Arg Trp
                405                 410                 415

Asp Val Asp Ala His Val Asp Pro Thr Gly Thr Lys Arg Asn Thr Ser
                420                 425                 430

Lys Val Pro Tyr Gly Cys Trp Ile Asn Glu Pro Gly Leu Phe Asp Pro
                435                 440                 445

Arg Phe Phe Asn Met Ser Pro Arg Glu Ala Leu Gln Ala Asp Pro Ala
                450                 455                 460

Gln Arg Leu Ala Leu Leu Thr Ala Tyr Glu Ala Leu Glu Met Ala Gly
465                 470                 475                 480

Phe Ile Pro Asp Ser Thr Pro Ser Thr Gln Arg Asp Arg Val Gly Leu
                485                 490                 495

Phe Tyr Gly Met Thr Ser Asp Tyr Arg Glu Ile Asn Ser Gly Gln
                500                 505                 510

Asp Ile Asp Thr Tyr Phe Ile Pro Gly Gly Asn Arg Ala Phe Thr Pro
                515                 520                 525

Gly Arg Ile Asn Tyr Tyr Phe Lys Phe Ser Gly Pro Ser Val Ser Val
                530                 535                 540

Asp Thr Ala Cys Ser Ser Leu Ala Ala Ile His Met Ala Cys Asn
545                 550                 555                 560

Ser Ile Trp Arg Asn Asp Cys Asp Ala Ala Ile Ala Gly Gly Val Asn
                565                 570                 575

Ile Leu Thr Asn Pro Asp Asn His Ala Gly Leu Asp Arg Gly His Phe
                580                 585                 590

Leu Ser Arg Thr Gly Asn Cys Asn Thr Phe Asp Asp Gly Ala Asp Gly
                595                 600                 605

Tyr Cys Arg Ala Asp Gly Val Gly Thr Ile Ile Leu Lys Arg Leu Glu
610                 615                 620

Asp Ala Gln Ala Asp Asn Asp Pro Ile Leu Gly Val Ile Asn Gly Ala
625                 630                 635                 640

Tyr Thr Asn His Ser Ala Glu Ala Val Ser Ile Thr Arg Pro His Val
                645                 650                 655

Gly Ala Gln Ala Phe Ile Phe Asn Lys Leu Leu Asn Asp Ala Asn Ile
                660                 665                 670

Asp Pro Lys Asp Val Ser Tyr Val Glu Met His Gly Thr Gly Thr Gln
                675                 680                 685

Ala Gly Asp Ala Val Glu Met Gln Ser Val Leu Asp Thr Phe Ala Pro
                690                 695                 700

Asp Tyr Arg Arg Gly Pro Gly Gln Ser Leu His Leu Gly Ser Ala Lys
705                 710                 715                 720
```

```
Ala Asn Val Gly His Gly Glu Ser Ala Ser Gly Val Thr Ala Leu Val
            725                 730                 735

Lys Val Leu Leu Met Met Lys Lys Asn Thr Ile Pro Pro His Cys Gly
            740                 745                 750

Ile Lys Thr Lys Ile Asn His Asn Phe Pro Thr Asp Leu Ala Gln Arg
            755                 760                 765

Asn Val His Ile Ala Phe Gln Pro Thr Pro Trp Asn Arg Pro Ala Ser
            770                 775                 780

Gly Lys Arg Gln Cys Phe Ile Asn Asn Phe Ser Ala Ala Gly Gly Asn
785                 790                 795                 800

Thr Ala Leu Leu Met Glu Asp Ala Pro Ile Ala Glu Val Lys Gly Gln
            805                 810                 815

Asp Thr Arg Pro Val His Val Val Ser Val Ser Ala Arg Ser Gln Ser
            820                 825                 830

Ala Leu Lys Asn Asn Ile Asn Ser Leu Val Lys Tyr Ile Asp Glu Gln
            835                 840                 845

Gly Arg Ser Phe Asn Val Asn Glu Ala Asp Phe Ile Pro Ser Leu Ala
            850                 855                 860

Tyr Thr Thr Thr Ala Arg Arg Ile His His Pro Phe Arg Val Thr Ala
865                 870                 875                 880

Ile Gly Ser Ser Leu Gln Glu Leu Arg Asp Ser Leu Asn Asn Ser Ser
            885                 890                 895

Arg Leu Glu Ser Phe Thr Pro Val Pro Ala Thr Ala Pro Gly Val Gly
            900                 905                 910

Phe Val Phe Ala Gly Gln Gly Ala Gln His Thr Gly Met Gly Arg Gln
            915                 920                 925

Leu Tyr Glu Lys Cys Ser Gln Phe Arg Ala Thr Met Gln His Phe Asp
            930                 935                 940

Cys Ile Ser Gln Asn Gln Gly Phe Pro Ser Ile Leu Pro Leu Val Asp
945                 950                 955                 960

Gly Ser Val Pro Val Glu Glu Leu Gly Pro Ile Val Thr Gln Leu Gly
            965                 970                 975

Thr Thr Cys Leu Gln Met Ala Leu Val Asn Tyr Trp Gly Ser Leu Gly
            980                 985                 990

Ile Lys Pro Ala Phe Val Leu Gly His Ser Leu Gly Glu Phe Ala Ala
            995                 1000                1005

Leu Asn Thr Ala Gly Val Leu Ser Thr Ser Asp Thr Ile Tyr Leu
            1010            1015            1020

Cys Gly Arg Arg Ala Thr Leu Leu Thr Glu Tyr Cys Gln Val Gly
            1025            1030            1035

Thr His Ala Met Leu Ala Val Lys Ala Ser Tyr Pro Gln Val Lys
            1040            1045            1050

Gln Leu Leu Lys Glu Gly Val Asp Glu Val Ala Cys Val Asn Ser
            1055            1060            1065

Pro Ser Glu Thr Val Val Ser Gly Leu Thr Ala Asp Ile Asp Asp
            1070            1075            1080

Leu Ala Gln Arg Cys Ser Thr Glu Gly Trp Lys Ser Thr Lys Leu
            1085            1090            1095

Arg Val Pro Phe Ala Phe His Ser Ala Gln Val Thr Pro Ile Leu
            1100            1105            1110

Glu Arg Phe Gln Glu Glu Ala Gln Gly Val Thr Phe Arg Lys Pro
            1115            1120            1125
```

```
Ser Leu Pro Phe Val Ser Ser Leu Leu Gly Glu Val Ile Thr Glu
1130             1135             1140

Ser Asn Tyr Asp Val Leu Gly Ala Gln Tyr Met Val Lys Gln Cys
1145             1150             1155

Arg Lys Ser Val Asn Phe Leu Gly Ala Leu Glu Ala Thr Arg Tyr
1160             1165             1170

Ala Lys Leu Met Thr Asp Lys Thr Val Trp Leu Glu Val Gly Ala
1175             1180             1185

His Thr Ile Cys Ser Gly Met Ile Lys Ala Thr Phe Gly Pro Gln
1190             1195             1200

Val Thr Thr Val Ala Ser Leu Arg Arg Glu Glu Asn Ala Trp Lys
1205             1210             1215

Val Leu Ser Asn Ser Leu Ser Ala Leu His Leu Ala Gly Ile Asp
1220             1225             1230

Ile Asn Trp Lys Glu Tyr His Gln Asp Phe Ser Ser Ser His Gln
1235             1240             1245

Val Leu Pro Leu Pro Ser Tyr Lys Trp Asp Leu Lys Asn Tyr Trp
1250             1255             1260

Ile Pro Tyr Thr Asn Asn Phe Cys Leu Thr Lys Gly Ala Pro Gln
1265             1270             1275

Thr Ala Ile Gln Ala Ala Pro Gln Thr Thr Phe Leu Thr Thr Ala
1280             1285             1290

Ala Gln Lys Val Val Glu Ser Arg Asp Asp Gly Thr Thr Ala Thr
1295             1300             1305

Val Val Val Gln Asn Asp Ile Ala Asp Pro Glu Leu Asn Arg Val
1310             1315             1320

Ile Gln Gly His Lys Val Asn Gly Ala Ala Leu Cys Pro Ser Ser
1325             1330             1335

Leu Tyr Ala Asp Ile Ala Gln Thr Leu Gly Glu Tyr Leu Ile Glu
1340             1345             1350

Lys Tyr Lys Pro Glu Phe Lys Asp Leu Gly Leu Asp Val Cys Asp
1355             1360             1365

Met Val Val Pro Lys Pro Leu Ile Ala Lys Gly Gly Glu Gln Leu
1370             1375             1380

Phe Arg Val Ser Ala Ile Ala Asn Trp Ala Glu Lys Lys Ala Ser
1385             1390             1395

Val Gln Val Tyr Ala Val Asn Ala Asp Gly Lys Lys Thr Val Asp
1400             1405             1410

His Ala Tyr Cys Thr Val Lys Phe Phe Asp Thr Asn Ala Ser Glu
1415             1420             1425

Leu Glu Trp Lys Arg Ile Ser Tyr Leu Val Lys Arg Ser Ile Asp
1430             1435             1440

Ser Leu His Gln Asn Ala Glu Thr Gly Glu Ala His Arg Ile Gln
1445             1450             1455

Arg Gly Met Val Tyr Lys Leu Phe Ser Ala Leu Val Asp Tyr Asp
1460             1465             1470

Glu Asn Phe Lys Ser Ile Arg Glu Val Ile Leu Asp Ser Asp Asn
1475             1480             1485

Asn Glu Ala Thr Ala Arg Val Lys Phe Gln Ala Pro Pro Gly Asn
1490             1495             1500

Phe His Arg Asn Pro Phe Trp Ile Asp Ser Phe Gly His Leu Ser
1505             1510             1515

Gly Phe Ile Met Asn Ala Ser Asp Ala Thr Asp Ser Lys Asn Gln
```

```
            1520                1525                1530
Val Phe Val Asn His Gly Trp Asp Ser Met Arg Cys Leu Lys Lys
            1535                1540                1545
Phe Ser Pro Asp Val Thr Tyr Arg Thr Tyr Val Arg Met Gln Pro
            1550                1555                1560
Trp Gln Asn Asn Ile Trp Ala Gly Asp Val Tyr Ile Phe Glu Gly
            1565                1570                1575
Asp Asp Ile Ile Ala Val Phe Gly Gly Val Lys Phe Gln Ala Leu
            1580                1585                1590
Ala Arg Lys Ile Leu Asp Thr Val Leu Pro Pro Val Gly Gly Ser
            1595                1600                1605
Lys Ala Pro Ile Thr Ala Lys Ser Pro Pro Ala Arg Thr Gln
            1610                1615                1620
Lys Ala Asn Thr Gly Ala Lys Thr Arg Pro Lys Ala Pro Val Pro
            1625                1630                1635
Ser Lys Ser Phe Thr Lys Ser Ser Gly Pro Ser Val Val Arg
            1640                1645                1650
Ala Leu Ser Ile Leu Ala Ser Glu Val Gly Leu Ala Glu Ser Glu
            1655                1660                1665
Ile Ser Asp Asp Met Val Phe Ala Asp Tyr Gly Val Asp Ser Leu
            1670                1675                1680
Leu Ser Leu Thr Val Thr Gly Arg Tyr Arg Glu Glu Leu Asn Leu
            1685                1690                1695
Asp Leu Asp Ser Ser Val Phe Thr Asp His Pro Thr Val Asn Asp
            1700                1705                1710
Phe Lys Arg Leu Ile Ala Gln Val Ser Pro Ser Glu Ser His Asp
            1715                1720                1725
Gly Ser Ser Ser Glu Gln Glu Ser Asn Phe Ser Phe Asn Gly Gly
            1730                1735                1740
Glu Ser Ser Ala Ser Thr Pro Asp Ile Thr Ser Pro Pro Asn
            1745                1750                1755
Glu Lys Val Ala Gln Val Glu Gln Asn Gly Thr Met Lys Glu Ile
            1760                1765                1770
Arg Asn Ile Met Ala Glu Glu Ile Gly Val Pro Ala Glu Glu Ile
            1775                1780                1785
Asp Pro Asp Glu Asn Leu Gly Glu Met Gly Met Asp Ser Leu Leu
            1790                1795                1800
Ser Leu Thr Val Leu Gly Arg Ile Arg Glu Thr Leu Asp Met Asp
            1805                1810                1815
Leu Pro Gly Glu Phe Phe Ile Glu Asn Gln Thr Leu Asn Asp Ile
            1820                1825                1830
Glu Val Ala Leu Asp Leu Lys Pro Lys Thr Thr Ser Ala Pro Ile
            1835                1840                1845
Pro Met Pro Glu Pro Val Lys Phe Pro Glu Ala Ile His Asp Leu
            1850                1855                1860
Gln Pro Lys Leu Ala Gln His Pro Lys Ala Thr Ser Ile Leu Leu
            1865                1870                1875
Gln Gly Asn Pro Arg Thr Ala Thr Lys Thr Leu Phe Leu Phe Pro
            1880                1885                1890
Asp Gly Ser Gly Ser Ala Thr Ser Tyr Ala Thr Ile Pro Gly Leu
            1895                1900                1905
Ser Pro Asp Val Cys Val Tyr Gly Leu Asn Cys Pro Tyr Met Lys
            1910                1915                1920
```

```
Thr Pro Glu Lys Leu Lys Cys Ser Leu Asp Glu Leu Thr Ala Pro
    1925                1930                1935

Tyr Val Ala Glu Ile Arg Arg Arg Gln Pro Lys Gly Pro Tyr Ser
    1940                1945                1950

Phe Gly Gly Trp Ser Ala Gly Gly Ile Cys Ala Tyr Asp Ala Ala
    1955                1960                1965

Arg His Leu Met Phe Glu Glu Gly Glu Gln Val Asp Arg Leu Leu
    1970                1975                1980

Leu Leu Asp Thr Pro Phe Pro Ile Gly Leu Glu Lys Leu Pro Gln
    1985                1990                1995

Arg Leu Tyr Gly Phe Phe Asn Ser Ile Gly Leu Phe Gly Glu Gly
    2000                2005                2010

Lys Thr Ala Pro Pro Ser Trp Leu Leu Pro His Phe Leu Ala Phe
    2015                2020                2025

Ile Asp Ala Leu Asp Ala Tyr Lys Ala Ala Pro Leu Pro Phe Lys
    2030                2035                2040

Asp Glu Lys Trp Ala Lys Lys Leu Pro Lys Thr Tyr Ile Ile Trp
    2045                2050                2055

Ala Lys Asp Gly Val Cys Gly Lys Pro Gly Asp Pro Arg Pro Asp
    2060                2065                2070

Pro Pro Thr Asp Gly Ser Lys Asp Pro Lys Glu Met Val Trp Leu
    2075                2080                2085

Leu Asn Asp Arg Thr Asp Leu Gly Pro Asn Lys Trp Asp Thr Leu
    2090                2095                2100

Val Gly Pro Glu Asn Ile Gly Gly Ile Thr Val Met Glu Asp Ala
    2105                2110                2115

Asn His Phe Thr Met Thr Lys Gly Glu Lys Ala Lys Glu Leu Ser
    2120                2125                2130

Thr Phe Met Ala Asn Ala Met Ala
    2135                2140

<210> SEQ ID NO 13
<211> LENGTH: 1566
<212> TYPE: DNA
<213> ORGANISM: Polyporus pinsitus

<400> SEQUENCE: 13
atgatgtcga ggtttcactc tcttctcgct ttcgtcgttg cttcccttac ggctgtggcc      60
cacgctggta tcggtcccgt cgccgaccta accatcacca acgcagcggt cagcccccgac    120 gggttttctc gccaggccgt cgtcgtgaac ggcggcaccc ctggccctct catcaccggt     180
aacatggggg atcgcttcca gctcaatgtc atcgacaacc ttaccaacca cgatgctg      240 aagagcacga gtattcactg gcacggtttc ttccagaagg gtaccaactg ggccgacggt     300
cccgccttca tcaaccagtg cccgatctca tctggtcact cgttcctgta cgacttccag    360
gttcctgacc aggctggtac cttctggtat cacagtcact gtctacgca gtactgtgat      420 ggtttgaggg gtccgttcgt tgtttacgac ccgaatgacc cggccgccga cctgtacgac     480
gtcgacaacg acgacactgt cattacccctt gtggattggt accacgtcgc cgcgaagctg   540
ggccccgcat tccctctcgg cgccgacgcc accctcatca cggtaaggg acgctcccc     600 agcacgacca ccgcggacct ctcagttatc agcgtcaccc cgggtaaacg ctaccgtttc    660
cgcctggtgt ccctgtcgtg cgaccccaac tacacgttca gcatcgatgg tcacaacatg   720
acgatcatcg agaccgactc aatcaacacg gcgcccctcg tcgtcgactc cattcagatc    780
```

```
ttcgccgccc agcgttactc cttcgtgctc gaggccaacc aggccgtcga caactactgg    840
attcgcgcca acccgaactt cggtaacgtc gggttcaccg gcggcattaa ctcggctatc    900
ctccgctacg atggtgccgc tgccgtggag cccaccacca cgcaaaccac gtcgactgcg    960
ccgctcaacg aggtcaacct gcacccgctg gttaccaccg ctgtgcctgg ctcgcccgtc   1020
gctggtggtg tcgacctggc catcaacatg gcgttcaact tcaacggcac caacttcttc   1080
atcaacggcg cgtctttcac gccccccgac cgtgcctgtcc tgctccagat catcagcggc   1140
gcgcagaacg cgcaggacct cctgccctcc ggtagcgtct actcgcttcc ctcgaacgcc   1200
gacatcgaga tctccttccc cgccaccgcc gccgccccgcg gtgcgcccca ccccttccac   1260
ttgcacgggc acgcgttcgc ggtcgtccgc agcgccggca gcacggttta caactacgac   1320
aaccccatct tccgcgacgt cgtcagcacg gggacgcctg cggccggtga caacgtcacc   1380
atccgcttcc gcaccgacaa ccccggcccg tggttcctcc actgccacat cgacttccac   1440
ctcgaggccg gcttcgccgt cgtgttcgcg gaggacatcc ccgacgtcgc gtcggcgaac   1500
cccgtccccc aggcgtggtc cgacctctgc ccgacctacg acgcgctcga cccgagcgac   1560
cagtaa                                                              1566
```

<210> SEQ ID NO 14
<211> LENGTH: 521
<212> TYPE: PRT
<213> ORGANISM: Polyporus pinsitus

<400> SEQUENCE: 14

```
Met Met Ser Arg Phe His Ser Leu Leu Ala Phe Val Val Ala Ser Leu
1               5                   10                  15

Thr Ala Val Ala His Ala Gly Ile Gly Pro Val Ala Asp Leu Thr Ile
            20                  25                  30

Thr Asn Ala Ala Val Ser Pro Asp Gly Phe Ser Arg Gln Ala Val Val
        35                  40                  45

Val Asn Gly Gly Thr Pro Gly Pro Leu Ile Thr Gly Asn Met Gly Asp
    50                  55                  60

Arg Phe Gln Leu Asn Val Ile Asp Asn Leu Thr Asn His Thr Met Leu
65                  70                  75                  80

Lys Ser Thr Ser Ile His Trp His Gly Phe Phe Gln Lys Gly Thr Asn
                85                  90                  95

Trp Ala Asp Gly Pro Ala Phe Ile Asn Gln Cys Pro Ile Ser Ser Gly
            100                 105                 110

His Ser Phe Leu Tyr Asp Phe Gln Val Pro Asp Gln Ala Gly Thr Phe
        115                 120                 125

Trp Tyr His Ser His Leu Ser Thr Gln Tyr Cys Asp Gly Leu Arg Gly
    130                 135                 140

Pro Phe Val Val Tyr Asp Pro Asn Asp Pro Ala Ala Asp Leu Tyr Asp
145                 150                 155                 160

Val Asp Asn Asp Asp Thr Val Ile Thr Leu Val Asp Trp Tyr His Val
                165                 170                 175

Ala Ala Lys Leu Gly Pro Ala Phe Pro Leu Gly Ala Asp Ala Thr Leu
            180                 185                 190

Ile Asn Gly Lys Gly Arg Ser Pro Ser Thr Thr Ala Asp Leu Ser
        195                 200                 205

Val Ile Ser Val Thr Pro Gly Lys Arg Tyr Arg Phe Arg Leu Val Ser
    210                 215                 220
```

```
Leu Ser Cys Asp Pro Asn Tyr Thr Phe Ser Ile Asp Gly His Asn Met
225                 230                 235                 240

Thr Ile Ile Glu Thr Asp Ser Ile Asn Thr Ala Pro Leu Val Val Asp
            245                 250                 255

Ser Ile Gln Ile Phe Ala Ala Gln Arg Tyr Ser Phe Val Leu Glu Ala
        260                 265                 270

Asn Gln Ala Val Asp Asn Tyr Trp Ile Arg Ala Asn Pro Asn Phe Gly
    275                 280                 285

Asn Val Gly Phe Thr Gly Gly Ile Asn Ser Ala Ile Leu Arg Tyr Asp
290                 295                 300

Gly Ala Ala Val Glu Pro Thr Thr Thr Gln Thr Thr Ser Thr Ala
305                 310                 315                 320

Pro Leu Asn Glu Val Asn Leu His Pro Leu Val Thr Thr Ala Val Pro
                325                 330                 335

Gly Ser Pro Val Ala Gly Gly Val Asp Leu Ala Ile Asn Met Ala Phe
            340                 345                 350

Asn Phe Asn Gly Thr Asn Phe Phe Ile Asn Gly Ala Ser Phe Thr Pro
        355                 360                 365

Pro Thr Val Pro Val Leu Leu Gln Ile Ile Ser Gly Ala Gln Asn Ala
    370                 375                 380

Gln Asp Leu Leu Pro Ser Gly Ser Val Tyr Ser Leu Pro Ser Asn Ala
385                 390                 395                 400

Asp Ile Glu Ile Ser Phe Pro Ala Thr Ala Ala Pro Gly Ala Pro
                405                 410                 415

His Pro Phe His Leu His Gly His Ala Phe Ala Val Val Arg Ser Ala
                420                 425                 430

Gly Ser Thr Val Tyr Asn Tyr Asp Asn Pro Ile Phe Arg Asp Val Val
            435                 440                 445

Ser Thr Gly Thr Pro Ala Ala Gly Asp Asn Val Thr Ile Arg Phe Arg
        450                 455                 460

Thr Asp Asn Pro Gly Pro Trp Phe Leu His Cys His Ile Asp Phe His
465                 470                 475                 480

Leu Glu Ala Gly Phe Ala Val Val Phe Ala Glu Asp Ile Pro Asp Val
                485                 490                 495

Ala Ser Ala Asn Pro Val Pro Gln Ala Trp Ser Asp Leu Cys Pro Thr
                500                 505                 510

Tyr Asp Ala Leu Asp Pro Ser Asp Gln
            515                 520

<210> SEQ ID NO 15
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 15
cctgcgttcg ttctgcggcc atgatgtcga ggtttcactc tc                              42

<210> SEQ ID NO 16
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 16
```
tccccgaaca tcgcgcggcc tggaagcgat cccccatgtt accgg            45

<210> SEQ ID NO 17
<211> LENGTH: 55
<212> TYPE: DNA
<213> ORGANISM: Artificial Sequence
<220> FEATURE:
<223> OTHER INFORMATION: Artificial DNA Primer

<400> SEQUENCE: 17
cctgcgttcg ttctgcggcc cgcattccct ctcggcgccg acgccaccct catca    55

<210> SEQ ID NO 18
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 18
tccccgaaca tcgcgcggcc tgatggccag gtcgacacca c                 41

<210> SEQ ID NO 19
<211> LENGTH: 54
<212> TYPE: DNA
<213> ORGANISM: Artificial Sequence
<220> FEATURE:
<223> OTHER INFORMATION: Artificial DNA Primer

<400> SEQUENCE: 19
cctgcgttcg ttctgcggcc gcaccaactt cttcatcaac ggcgcgtctt tcac    54

<210> SEQ ID NO 20
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 20
tccccgaaca tcgcgcggcc ttactggtcg ctcgggtcga                   40

<210> SEQ ID NO 21
<211> LENGTH: 593
<212> TYPE: DNA
<213> ORGANISM: Aspergillus niger

<400> SEQUENCE: 21
atggagaccg atcccggatt catcgctgct gtggaagaag ccaagcaagg cgctgctgag    60
ggtggtgtgc ccattggagc ttgtttggtc tccaaggatg gcaagattct aggccgcggc   120
cacaatatgc gcgtccagaa gggtagtccc gtgttgcatg ttcgttgatc ccatcccttg   180
ccttctgagg gtcgtctggg gttctaattc taatctctac cgtcataggc tgagatgtcc   240
gcgctcgaga actccggtcg tctgcccgct tcggcctacg aaggcgctac tatgtacacg   300
accctgtcgc catgcgacat gtgcaccggt gcctgcatcc tctacaaggt taagcgcgtt   360
gttgtgggcg agaacaagag cttcatgggt ggcgaggact atcttaagag ccgtgggaag   420
gaggttgtgg tttttggataa tgcagagtgt aagcagctga tggagaagtt catgaaggag   480
aagccggagc tttggtaggt ttcccatgca tctcactgga ctggtctagt cttttgttgg   540
aatgtacgct gactgtacga tgtctttgca ggaatgagga catttccgtc tga         593

```
<210> SEQ ID NO 22
<211> LENGTH: 148
<212> TYPE: PRT
<213> ORGANISM: Aspergillus niger

<400> SEQUENCE: 22

Met Glu Thr Asp Pro Gly Phe Ile Ala Val Glu Glu Ala Lys Gln
 1               5                  10                  15

Gly Ala Ala Glu Gly Gly Val Pro Ile Gly Ala Cys Leu Val Ser Lys
                20                  25                  30

Asp Gly Lys Ile Leu Gly Arg Gly His Asn Met Arg Val Gln Lys Gly
            35                  40                  45

Ser Pro Val Leu His Ala Glu Met Ser Ala Leu Glu Asn Ser Gly Arg
        50                  55                  60

Leu Pro Ala Ser Ala Tyr Glu Gly Ala Thr Met Tyr Thr Thr Leu Ser
65                  70                  75                  80

Pro Cys Asp Met Cys Thr Gly Ala Cys Ile Leu Tyr Lys Val Lys Arg
                85                  90                  95

Val Val Val Gly Glu Asn Lys Ser Phe Met Gly Gly Glu Asp Tyr Leu
               100                 105                 110

Lys Ser Arg Gly Lys Glu Val Val Leu Asp Asn Ala Glu Cys Lys
               115                 120                 125

Gln Leu Met Glu Lys Phe Met Lys Glu Lys Pro Glu Leu Trp Asn Glu
        130                 135                 140

Asp Ile Ser Val
145

<210> SEQ ID NO 23
<211> LENGTH: 28
<212> TYPE: DNA
<213> ORGANISM: Artificial Sequence
<220> FEATURE:
<223> OTHER INFORMATION: Artificial DNA Primer

<400> SEQUENCE: 23
catggccatg ggctgagatg tccgcgct                                          28

<210> SEQ ID NO 24
<211> LENGTH: 35
<212> TYPE: DNA
<213> ORGANISM: Artificial Sequence
<220> FEATURE:
<223> OTHER INFORMATION: Artificial DNA Primer

<400> SEQUENCE: 24
ataagaatgc ggccgccaaa gctccggctt ctcct                                  35

<210> SEQ ID NO 25
<211> LENGTH: 35
<212> TYPE: DNA
<213> ORGANISM: Artificial Sequence
<220> FEATURE:
<223> OTHER INFORMATION: Artificial DNA Primer

<400> SEQUENCE: 25
ggagctttgg cggccatgcg tttcacgctc ctcac                                  35

<210> SEQ ID NO 26
<211> LENGTH: 35
<212> TYPE: DNA
<213> ORGANISM: Artificial Sequence
<220> FEATURE:
```

<223> OTHER INFORMATION: Artificial DNA Primer

<400> SEQUENCE: 26
gaacatcgcg cggccgcttc gggtggatgt gctcg                35